(12) United States Patent
Ossovskaya et al.

(10) Patent No.: US 7,538,252 B2
(45) Date of Patent: May 26, 2009

(54) DRUG DESIGN FOR TUBULIN INHIBITORS, COMPOSITIONS, AND METHODS OF TREATMENT THEREOF

(75) Inventors: Valeria Ossovskaya, San Francisco, CA (US); John Burnier, Pacifica, CA (US); Barry Sherman, Hillsborough, CA (US); Max Totrov, San Diego, CA (US)

(73) Assignee: BiPar Sciences, Inc., Brisbane, CA (US)

( * ) Notice: Subject to any disclaimer, the term of this patent is extended or adjusted under 35 U.S.C. 154(b) by 0 days.

(21) Appl. No.: 11/850,620

(22) Filed: Sep. 5, 2007

(65) Prior Publication Data
US 2008/0076737 A1  Mar. 27, 2008

Related U.S. Application Data

(60) Provisional application No. 60/842,480, filed on Sep. 5, 2006.

(51) Int. Cl.
*C07C 213/00* (2006.01)
*C07C 49/00* (2006.01)
*C07C 41/00* (2006.01)

(52) U.S. Cl. .................. 564/430; 568/335; 568/336; 568/635

(58) Field of Classification Search .................. None
See application file for complete search history.

(56) References Cited

U.S. PATENT DOCUMENTS

| | | |
|---|---|---|
| 5,908,861 A | 6/1999 | Kun |
| 5,922,775 A | 7/1999 | Kun et al. |
| 6,303,629 B1 | 10/2001 | Kun |
| 6,326,402 B1 | 12/2001 | Kun et al. |
| 2007/0015814 A1 | 1/2007 | Kun et al. |
| 2007/0015837 A1 | 1/2007 | Kun et al. |
| 2007/0292883 A1 | 12/2007 | Ossovskaya et al. |
| 2008/0076778 A1 | 3/2008 | Ossovskaya et al. |
| 2008/0103104 A1 | 5/2008 | Moore et al. |
| 2008/0103208 A1 | 5/2008 | Ossovskaya et al. |
| 2008/0176946 A1 | 7/2008 | Ossovskaya et al. |
| 2008/0262062 A1 | 10/2008 | Ossovskaya et al. |
| 2008/0319054 A1 | 12/2008 | Kun et al. |

OTHER PUBLICATIONS

Abstract, Jorgensen et al., Journal of Organic Chemistry (1964), 29(11), 3396-8; CAS online citation 62:22370 [retrieved Dec. 15, 2008] from STN; Columbus, OH, USA.*

(Continued)

*Primary Examiner*—Karl J Puttlitz
(74) *Attorney, Agent, or Firm*—Albert P. Halluin; Wilson Sonsini Goodrich & Rosati

(57) ABSTRACT

The present invention relates to a computer-assisted method of a designing of a tubulin inhibitor comprising: a) determining an interaction between a tubulin protein and a chemical known to bind the tubulin protein by evaluating a binding of the tubulin protein to the chemical known to bind the tubulin protein; b) based on the interaction, designing a candidate tubulin inhibitor; c) determining an interaction between the tubulin protein and the candidate tubulin inhibitor by evaluating a binding of the tubulin protein to the candidate tubulin inhibitor; and d) concluding that the candidate tubulin inhibitor inhibits the tubulin protein wherein the conclusion is based on the interaction of step c). The invention also provides compositions and methods of treatment of diseases with the candidate tubulin inhibitors.

5 Claims, 7 Drawing Sheets

OTHER PUBLICATIONS

Abstract, Kirsten et al., International Journal of Oncology (1998), 13(1), 49-55; CAS online citation 129:197657 [retrieved Dec. 15, 2008] from STN; Columbus, OH, USA.*

Kodavanti, et al. Differential effects of polybrominated diphenyl ethers and polychlorinated biphenyls on [3H]arachidonic acid release in rat cerebellar granule neurons. Toxicol Sci. 2002; 68(2):451-7.

Geney, et al. Use of the tubulin bound paclitaxel conformation for structure-based rational drug design. Chem Biol. 2005; 12(3):339-48.

Finical, et al. New Anticancer Drugs from Cultured and Collected Marine Organisms. Pharmaceutical Biology. 2003;41:6-14.

Giannakakou, et al. A common pharmacophore for epothilone and taxanes: Molecular basis for drug resistance conferred by tubulin mutations in human cancer cells. PNAS. 2003;97(6):2904-2909.

Gonindard, et al. Synthetic hispidin, a PKC inhibitor, is more cytotoxic toward cancer cells than normal cells in vitro. Cell Biology and Toxicology. 1997;13:141-153.

Lee, et al. Comparative molecular field analysis (CoMFA) study of epothilones—tubulin depolymerization inhibitors: Pharmacophore development using 3D QSAR methods. Journal of Computer-Aided Molecular Design. 2001;15:41-55.

Adkins, et al. Eds. Organic Syntheses: An Annual Publication of Satisfactory Methods for the preparation of Organic Chemicals. John Wiley & Sons. New York, NY. 1942 22:52.

Amemiya, Y. X-Ray Storage-Phosphor Imaging-Plate Detectors : High-Sensitivity X-Ray Area Detector. Methods in Enzymology. 1997;276: 233-243.

Auerbach, et al. A simple procedure for the long-term cultivation of chicken embryos. Dev. Biol. 1974; 41:391-394.

Belmont, et al. Identification of a protein that interacts with tubulin dimers and increases the catastrophe rate of microtubules. Cell. 1996; 84: 623-631.

Beringer, et al. Diaryliodonium Salts IX. The Synthesis of Substituted Diphenyliodonium Salts. Journal of the American Chemical Society. 1959; 81:342-351.

Bernstein, et al. 125I interstitial implants in the RIF-1 murine flank tumor: an animal model for brachytherapy. Radiation Res. 1982; 91:624-637.

Blundell, et al. 18th Sir Hans Krebs lecture. Knowledge-based protein modelling and design. Eur J. Biochem. 1988; 172: 513-520.

Brown, et al. Response to the RIF-1 tumor in vitro and in C3H/Km mice to X-radiation (cell survival, regrowth delay, and tumor control), chemotherapeutic agents, and activated macrophages. J. Nat'l Cancer Inst. 1980; 64: 605-611.

Burton, et al. Traction forces of cytokinesis measured with optically modified elastic substrate. Nature. 1997; 385:450-454.

Chan, et al. New N- and O-arylations with phenylboronic acids and cupric acetate Tetrahedton Lett. 1998; 39: 2933-2936.

Downing, et al. Crystallographic structure of tubulin: implications for dynamics and drug binging. Cell Structure and Function. 1999; 24:269-271.

Drukman, et al. Microtubule alterations and resistance to tubulin-binding agents (review). International Journal of Oncology. 2002; 21:621-628.

Dugaiczyk. Cloning and Sequencing of a Deoxyribonucleic Acid Glyceraldehyde-3-phosphate Dehydrogenase Messenger Ribonucleic Acid Isolated from Chicken Muscle. Biochem. 1983; 22: 1605-1613.

Evans, et al. Synthesis of diaryl ethers through the copper-promoted arylation of phenols with arylboronic acids. An expedient synthesis of thyroxine Tetrahedron Lett. 1998; 39:2937-2940.

Evans, et al. Total synthesis of teicoplanin aglycon. J. Am. Chem. Soc. 2001; 123: 12411-12413.

Fabbri, et al. Sequential events of apoptosis involving docetaxel, a microtubule-interfering agent: a cytometric study. BMC Cell Biology. 2006; 7:6.

Gaskin, et al. Turbidimetric studies of the in vitro assembly and disassembly of porcine neurotubules. J. Mol. Biol. 1974; 89:737-758.

Gowda, et al. Zinc-catalyzed Ammonium Formate Reductions: Rapid and Selective Reduction of Aliphatic Nitro Compounds. Indian J. Chem. 2001; 40B: 75-77.

Greer. Model structure for the inflammatory protein C5a. Science. 1985; 228:1055-1060.

Hadfield, et al. Tubulin and microtubules as targets for anticancer drugs. Progress in Cell Cycle Research. 2003; 5:309-325.

Hantson, et al. 5th International Conference on Isotopes. Brussels, Belgium. 2005; 279-283.

Hyman, et al. Protein that prevents mercaptan-mediated protein oxidation. Meth Enzymol. 1990; 196: 478-485.

Jones, et al. Improved methods for building protein models in electron density maps and the location of errors in these models. Acta Crystallogr A. 1991; 47: 100-119.

Kahn, et al. Gas Proportional Detectors. Methods in Enzymology. 1997; 276: 268-286.

Kirschner, et al. Microtubules from mammalian brain: some properties of their depolymerization products and a proposed mechanism of assembly and disassembly. Proc. Natl. Acad. Sci. USA. 1974; 71: 1159-1163.

Levitt. A new software routine that automates the fitting of protein X-ray crystallographic electron-density maps. Acta Crystallogr D. 2001; 57:1013-1019.

Maragoudakis, et al. Antiangiogenic action of heparin plus cortisone is associated with decreased collagenous protein synthesis in the chick chorioallantoic membrane system. J. Pharm Exp Ther. 1989; 251: 679-682.

McPherson. Current approaches to macromolecular crystallization. Eur. J. Biochem. 1990; 189:1-23.

McPherson. The preparation and analysis of protein crystals. John Wiley. New York. 1982.

Mendeleyev, et al. Structrual Specificity and tumoricidal action of methyl-3, 5-diiodo-4-(4'-methoxyphenoxy) benzogate (DIME). Int. J. Oncol. 1997; 10:689-695.

Muathen, H. Selective Nitration of Aromatic Compounds with Bismuth Subnitrate and Thionyl Chloride. Molecules. 2003; 8:593-598.

Nogales, et al. Structure of the alpha beta tubulin dimer by electron crystallography. Nature 1998; 391:199-202.

Perich, et al. Di-*tert*-butyl *N,N*-Diethylphosphoramidite. A New Phosphitylating Agent for the Efficient Phosphorylation of Alcohols. Synthesis. 1988; 142-144.

Perrakis, et al. Automated protein model building combined with iterative structure refinement. Nature Structural Biology. 1999; 6(5): 458-463.

Saimoto, et al. A mild procedure for hydrolysis of alkoxymethyl aryl ethers to give hydroxyarenes. A ational synthesis of ascofuranone Tetrahedron Lett. 1986; 27:1607-1610.

Tiwari, et al. A ph and temperature-dependent cycling method that doubles the yield of microtubule protein. Anal Biochem. 1993; 215:96-103.

Twentyman, et al. A new mouse tumor model system (RIF-1) for comparison of end-point studies. J. Nat'l Cancer Inst. 1980; 64: 595-604.

Waleh, et al. Selective down-regulation of integrin receptors in spheroids of squamous cell carcinoma. Cancer Res. 1994; 54:838-843.

Weber, P. Physical principles of protein crystallization. Adv. Protein Chem. 1991; 41:1-36.

Westbrook, et al. Charge-coupled device-based area detectors. Method in Enzymology. 1997; 276:244-268.

Wilson, et al. Genomic 5-methylcytosine determination by 32P-postlabeling analysis. Anal. Biochem. 1986; 152: 275-284.

Woods, et al. The interaction with tubulin of a series of stilbenes based on combretastatin A-4. British J. Cancer. 1995; 71: 705-711.

Yoo, et al. Mild and efficient Deoxygenation of Amine-N-Oxides with FeCl3-6H2O-Indium System under Ultrasonication. Bulletin of the Korean Chemical Society. 2004; 25(11):1633-1634.

* cited by examiner

GF7 – antibody detecting cells that are in mitosis

DRUG DESIGN FOR TUBULIN INHIBITORS, COMPOSITIONS, AND METHODS OF TREATMENT THEREOF

CROSS-REFERENCE

This application claims the benefit of U.S. Provisional Application No. 60/842,480, filed Sep. 5, 2006, which is incorporated herein by reference in its entirety.

BACKGROUND OF THE INVENTION

Tubulin proteins are essential building blocks of the microtubules of cells, which in turn form a major part of the cellular cytoskeleton and are involved in important cellular functions including intracellular transport, maintenance of cell shape, chromosome segregation during mitosis, and cell motility. Polymers of alpha and beta tubulin subunit heterodimers form hollow cylindrical filament structures which comprise the microtubules. The dynamic between microtubular polymerization and depolymerization is essential to mitosis.

There exist multiple isoforms of the alpha and beta tubulin proteins, with distinct patterns of expression amongst different types of cells such as brain and hematopoietic cells (Drukman et al. 2002, International Journal of Oncology, 21:621-28.). Additionally, some forms of tubulin exist ubiquitously.

Because of the role microtubules play in mitosis, they are attractive targets for chemotherapeutic intervention for cancer. Drugs affecting microtubule function have primarily targeted the alpha and beta tubulin heterodimers, and have been shown to have various binding sites on the heterodimer (Hadfield et al., 2003, Progress in Cell Cycle Research, 5:309-25). Such sites include colchicine, vinca alkaloid, paclitaxel, and other binding sites.

Drugs targeting tubulin form two main families: microtubule-destabilizers and microtubule-stabilizers. Destabilizing agents include the vinca alkaloids, such as vincristine, vinblastine, and vinorelbine. Their mechanism of action is thought to be through tubulin self-association, causing formation of structures other than the normal hollow cylinders of normal microtubules. Stabilizing agents include taxanes like paclitaxel and docetaxel. Their mechanism of action causes the microtubule to stabilize and prevents it from depolymerizing, disrupting the polymerization/depolymerization equilibrium essential for mitosis.

Despite the existence of tubulin-targeting drugs, cancer cells also have exhibited an ability to overcome their effects, becoming resistant to such chemotherapeutic agents. Examples of resistance mechanisms to tubulin-targeting drugs include increased expression and activity of the drug resistant P-glycoprotein ("P-gp") pump, altered expression of tubulin subtypes and isoforms, mutations in tubulin proteins including in drug binding sites, and post-translational modifications of tubulin proteins such as acetylation. These resistance mechanisms reveal that there is a need for novel chemotherapeutic agents that target tubulin, yet are less susceptible to chemotherapeutic drug resistance.

The identification of tubulin inhibitors can be attempted using methods such as screening of large numbers of random libraries of natural and/or synthetic compounds. However, this method is inefficient in that it typically results in a small number of positive "hits" and is constrained by logistical factors accompanying large screening processes.

Another method of such identification is structure-based drug design ("SBDD"). SBDD comprises a number of integrated components including structural information (eg. spectroscopic data like X-ray or magnetic resonance information, relating to enzyme structure and/or conformation, protein-ligand interactions, etc.), computer modeling, medicinal chemistry, and biological testing (both in vivo and in vitro). These components, each alone or in combination, are useful for accelerating the drug discovery process, for gaining insight into disease and disease processes, and for providing a more efficient method for identifying drug candidates.

Accordingly, the present invention provides compositions and methods related to a design of candidate tubulin inhibitors and methods of treatment thereof.

SUMMARY OF THE INVENTION

One aspect of the present invention relates to a computer-assisted method of a designing of a tubulin inhibitor by a) determining an interaction between a tubulin protein and a chemical known to bind the tubulin protein by evaluating a binding of the tubulin protein to the chemical known to bind the tubulin protein; b) based on the interaction, designing a candidate tubulin inhibitor; c) determining an interaction between the tubulin protein and the candidate tubulin inhibitor by evaluating a binding of the tubulin protein to the candidate tubulin inhibitor; and d) ascertaining that the candidate tubulin inhibitor inhibits the tubulin protein wherein the conclusion is based on the interaction of step c). In some embodiments, the tubulin protein is a three-dimensional structure comprising a binding domain of the tubulin protein. In some embodiments, the binding domain of the tubulin protein is for example, colchicine binding domain, vinblastine binding domain, and paclitaxel binding domain. In some embodiments, the tubulin protein is derived from a crystal of the tubulin protein. In some embodiments, the designing is performed in conjunction with a computer modeling. In some embodiments, the binding domain of the tubulin protein is an intradimer surface. In some other embodiments, the binding domain of the tubulin protein is an interdimer surface. In still some embodiments, the binding domain of the tubulin protein is a surface facing inside of a microtubule near an interprotofilament interface at a distance from any longitudinal interface. In some embodiments, the surface is a paclitaxel binding site.

In some embodiments of the aforementioned aspect of the present invention, the designing involves replacing a substituent on the chemical known to bind the tubulin protein with another substituent wherein the other substituent improves the binding of the candidate tubulin inhibitor with the tubulin protein. In some embodiments, the interaction is for example, steric interaction, van der Waals interaction, electrostatic interaction, solvation interaction, charge interaction, covalent bonding interaction, non-covalent bonding interaction, entropically favorable interaction, enthalpically favorable interaction, or a combination thereof. In some embodiments, the candidate tubulin inhibitor is an analogue of the chemical known to bind the tubulin protein. In some embodiments, the chemical known to bind the tubulin protein is a ketone that is a thyroxine analogue. In still some embodiments, the method further comprises of a step of chemically synthesizing the candidate tubulin inhibitor. In some embodiments, the method further comprises of evaluating a tubulin inhibitory activity of the candidate tubulin inhibitor and selecting the candidate tubulin inhibitor based on the evaluation. In some embodiments, the evaluation of the tubulin inhibiting activity involves an assay technique.

In some embodiments of the aforementioned computer-assisted method of a designing of a tubulin inhibitor, the candidate tubulin inhibitor is a compound of formula I, its pharmaceutically acceptable salts, or prodrugs thereof:

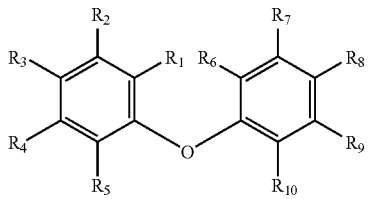

Formula I wherein: $R_1$ and $R_5$ are halogens; $R_2$, $R_3$, and $R_4$ are independently selected from the group consisting of hydrogen, hydroxyl, halogen, ester, optionally substituted alkoxy, optionally substituted amine, phosphate, optionally substituted alkyl, and optionally substituted acetyl; and $R_6$, $R_7$, $R_8$, $R_9$, and $R_{10}$ are independently selected from the group consisting of hydrogen, hydroxyl, halogen, optionally substituted alkoxy, optionally substituted amine, phosphate, optionally substituted alkyl, optionally substituted alkenyl, optionally substituted alkynyl, nitroso, carboxyl, optionally substituted cycloalkyl, and optionally substituted heterocyclic.

In some embodiments of the aforementioned aspect, the candidate tubulin inhibitor is a compound of formula II or its pharmaceutically acceptable salts or prodrugs:

Formula II

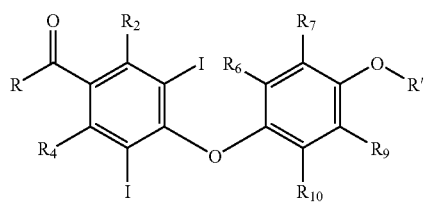

wherein: R, R', $R_2$, $R_4$, $R_6$, $R_7$, $R_9$, and $R_{10}$ are independently selected from the group consisting of hydrogen, hydroxyl, halogen, optionally substituted alkoxy, optionally substituted amine, phosphate, optionally substituted alkyl, and optionally substituted acetyl.

In some embodiments, the candidate tubulin inhibitor is a compound of formula III or its pharmaceutically acceptable salts or prodrugs:

Formula III

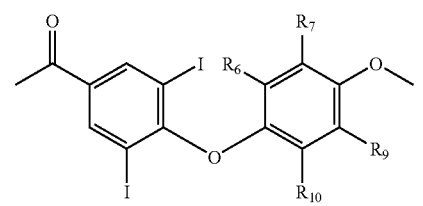

wherein: $R_6$, $R_7$, $R_9$, and $R_{10}$ are independently selected from the group consisting of hydrogen, hydroxyl, optionally substituted amine, phosphate, and optionally substituted alkyl.

In some embodiments, the candidate tubulin inhibitor is 1-(4-(3-hydroxy-4-methoxyphenoxy)-3,5-diiodophenyl) ethanone, represented by formula IIIA or its pharmaceutically acceptable salts or prodrugs:

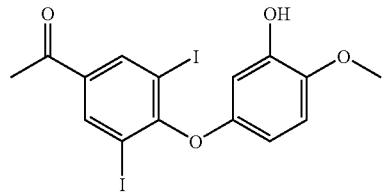

Formula IIIA

In some embodiments, the candidate tubulin inhibitor is 1-(4-(3-amino-4-methoxyphenoxy)-3,5-diiodophenyl)ethanone, represented by formula IIIB or its pharmaceutically acceptable salts or prodrugs:

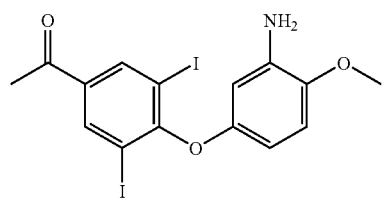

Formula IIIB

In some embodiments, the candidate tubulin inhibitor is a compound of formula IIIC or its pharmaceutically acceptable salts or prodrugs:

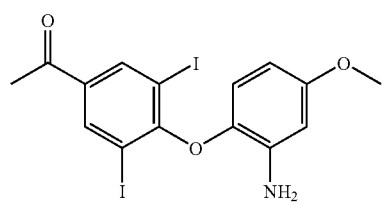

Formula IIIC

In some embodiments, the candidate tubulin inhibitor is mono (5-methoxy-3-(4-acetyl-2,6-iodophenoxy)phenyl) phosphoric acid ester, represented by formula IIID or its pharmaceutically acceptable salts or prodrugs:

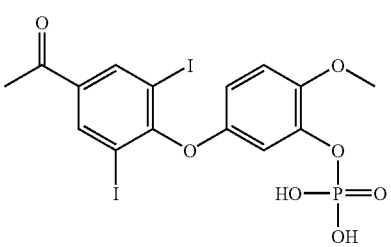

Formula IIID

In some embodiments, the optionally substituted alkyl is substituted with an optionally substituted heterocyclic. In some embodiments, the optionally substituted heterocyclic is for example, azeridine, azetidine, pyrrole, dihydropyrrole, pyrrolidene, pyrazole, pyrazoline, pyrazolidine, imidazole, benzimidazole, triazole, tetrazole, oxazole, isoxazole, benzoxazole, oxadiazole, oxazoline, oxazolidine, thiazole, isothiazole, pyridine, dihydropyridine, tetrahydropyridine, quinazoline, pyrazine, pyrimidine, pyridazine, quinoline, isoquinoline, triazine, tetrazine, and piperazine.

In some embodiments, the candidate tubulin inhibitor is the compound 1-(4-(2-(N-piperazinylprop-3-yl))-4-methoxyphenoxy)-3,5-diiodophenyl)ethanone, represented by formula IIIE or its pharmaceutically acceptable salts or prodrugs:

Formula IIIE

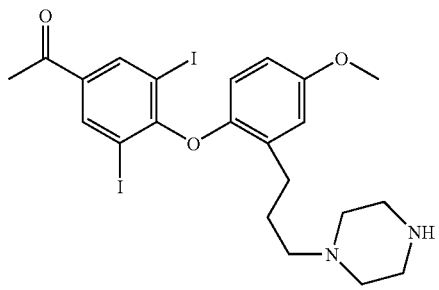

Another aspect of the invention relates to a computer system containing a set of information to perform a design of a tubulin inhibitor having a user interface comprising a display unit, the set of information comprises a) logic for inputting an information regarding a binding of a tubulin protein to a chemical known to bind tubulin protein; b) logic for designing a candidate tubulin inhibitor based on the binding of the tubulin protein to the chemical known to bind tubulin protein; c) logic for determining an information regarding a binding of the tubulin protein to the candidate tubulin inhibitor; and d) logic for making a conclusion regarding a tubulin inhibitory properties of the candidate tubulin inhibitor based on the determination of step c).

Yet another aspect of the invention relates to a computer-readable storage medium containing a set of information for a general purpose computer having a user interface comprising a display unit, the set of information comprises a) logic for inputting an information regarding a binding of a tubulin protein to a chemical known to bind tubulin protein; b) logic for designing a candidate tubulin inhibitor based on the binding of the tubulin protein to the chemical known to bind tubulin protein; c) logic for determining an information regarding a binding of the tubulin protein to the candidate tubulin inhibitor; and d) logic for making a conclusion regarding a tubulin inhibitory properties of the candidate tubulin inhibitor based on the determination of step c). In some embodiments, the chemical is a ketone which is a thyroxine analogue. In some embodiments, the chemical is a ketone which is a thyroxine analogue.

Yet another aspect of the invention relates to an electronic signal or carrier wave that is propagated over the internet between computers comprising a set of information for a general purpose computer having a user interface comprising a display unit, the set of information comprising a computer-readable storage medium containing a set of information for a general purpose computer having a user interface comprising a display unit, the set of information comprises a) logic for inputting an information regarding a binding of a tubulin protein to a chemical known to bind tubulin protein; b) logic for designing a candidate tubulin inhibitor based on the binding of the tubulin protein to the chemical known to bind tubulin protein; c) logic for determining an information regarding a binding of the tubulin protein to the candidate tubulin inhibitor; and d) logic for making a conclusion regarding a tubulin inhibitory properties of the candidate tubulin inhibitor based on the determination of step c).

Another aspect of the invention relates to a method of treating a disease by administering to a patient in need thereof an effective amount of at least one compound of formula I, its pharmaceutically acceptable salts, or prodrugs thereof:

Formula I

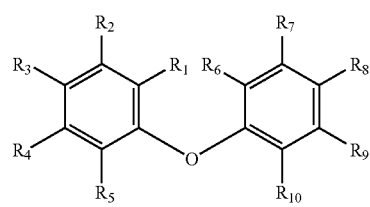

wherein: $R_1$ and $R_5$ are halogens; $R_2$, $R_3$, and $R_4$ are independently selected from the group consisting of hydrogen, hydroxyl, halogen, ester, optionally substituted alkoxy, optionally substituted amine, phosphate, optionally substituted alkyl, and optionally substituted acetyl; and $R_6$, $R_7$, $R_8$, $R_9$, and $R_{10}$ are independently selected from the group consisting of hydrogen, hydroxyl, halogen, optionally substituted alkoxy, optionally substituted amine, phosphate, optionally substituted alkyl, optionally substituted alkenyl, optionally substituted alkynyl, nitroso, carboxyl, optionally substituted cycloalkyl, and optionally substituted heterocyclic.

In some embodiments of aforementioned method of treating a disease, the compound is of formula II or its pharmaceutically acceptable salts or prodrugs:

Formula II

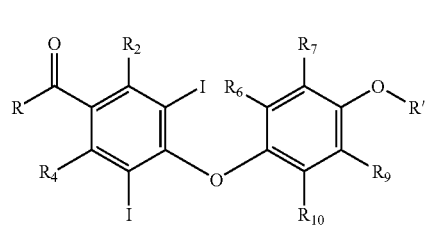

wherein: R, R', $R_2$, $R_4$, $R_6$, $R_7$, $R_9$, and $R_{10}$ are independently selected from the group consisting of hydrogen, hydroxyl, halogen, optionally substituted alkoxy, optionally substituted amine, phosphate, optionally substituted alkyl, and optionally substituted acetyl. In some embodiments, the compound is of formula III or its pharmaceutically acceptable salts or prodrugs:

Formula III

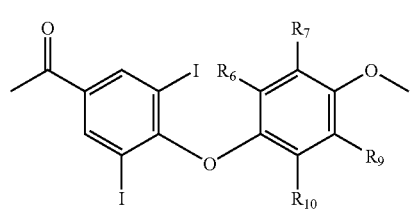

wherein: $R_6$, $R_7$, $R_9$, and $R_{10}$ are independently selected from the group consisting of hydrogen, hydroxyl, optionally substituted amine, phosphate, and optionally substituted alkyl. In some embodiments, the compound is 1-(4-(3-hydroxy-4-methoxyphenoxy)-3,5-diiodophenyl)ethanone, represented by formula IIIA or its pharmaceutically acceptable salts or prodrugs:

Formula IIIA

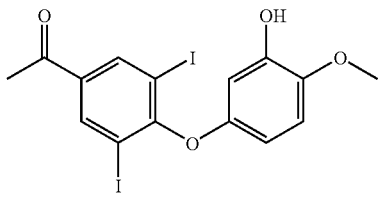

In some embodiments, the compound is 1-(4-(3-amino-4-methoxyphenoxy)-3,5-diiodophenyl)ethanone, represented by formula IIIB or its pharmaceutically acceptable salts or prodrugs:

Formula IIIB

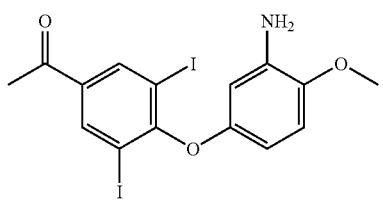

In some embodiments, the compound is 1-(4-(2-amino-4-methoxyphenoxy)-3,5-diiodophenyl)ethanone, represented by formula IIIC or its pharmaceutically acceptable salts or prodrugs:

Formula IIIC

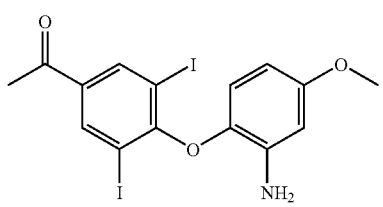

In some embodiments, the compound is mono (5-methoxy-3-(4-acetyl-2,6-iodophenoxy)phenyl) phosphoric acid ester, represented by formula IIID or its pharmaceutically acceptable salts or prodrugs:

Formula IIID

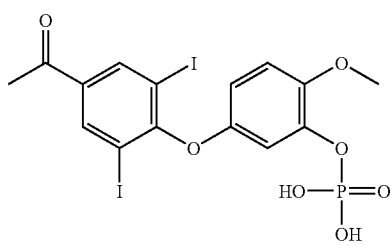

In some embodiments, the optionally substituted alkyl is substituted with an optionally substituted heterocyclic. In some embodiments, the optionally substituted heterocyclic is for example, azeridine, azetidine, pyrrole, dihydropyrrole, pyrrolidene, pyrazole, pyrazoline, pyrazolidine, imidazole, benzimidazole, triazole, tetrazole, oxazole, isoxazole, benzoxazole, oxadiazole, oxazoline, oxazolidine, thiazole, isothiazole, pyridine, dihydropyridine, tetrahydropyridine, quinazoline, pyrazine, pyrimidine, pyridazine, quinoline, isoquinoline, triazine, tetrazine, and piperazine. In some embodiments, the candidate tubulin inhibitor is 1-(4-(2-(N-piperazinylprop-3-yl))-4-methoxyphenoxy)-3,5-diiodophenyl)ethanone, represented by formula IIIE or its pharmaceutically acceptable salts or prodrugs:

Formula IIIE

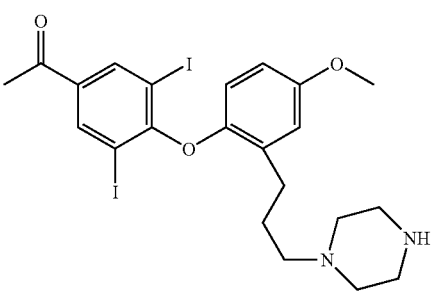

In some embodiments, the treating comprises inhibiting tubulin protein function. In some embodiments, the disease is for example, cancer, inflammation, metabolic disease, gout, CVS disease, CNS disease, disorder of the hematolymphoid system, disorder of endocrine and neuroendocrine, disorder of urinary tract, disorder of respiratory system, disorder of female genital system, and disorder of male genital system.

Another aspect of the present invention relates to a compound of formula I or its pharmaceutically acceptable salts or prodrugs:

Formula I

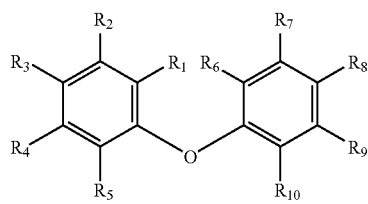

wherein: $R_1$ and $R_5$ are halogens; $R_2$, $R_3$, and $R_4$ are independently selected from the group consisting of hydrogen, hydroxyl, halogen, ester, optionally substituted alkoxy, optionally substituted amine, phosphate, optionally substituted alkyl, and optionally substituted acetyl; and $R_6$, $R_7$, $R_8$, $R_9$, and $R_{10}$ are independently selected from the group consisting of hydrogen, hydroxyl, halogen, optionally substituted alkoxy, optionally substituted amine, phosphate, optionally substituted alkyl, optionally substituted alkenyl, optionally substituted alkynyl, nitroso, carboxyl, optionally substituted cycloalkyl, and optionally substituted heterocyclic. Preferably, the compound is a tubulin inhibitor.

In some embodiments, the compound is of formula II or its pharmaceutically acceptable salts or prodrugs:

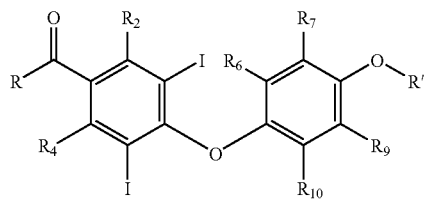

Formula II wherein: R, R', $R_2$, $R_4$, $R_6$, $R_7$, $R_9$, and $R_{10}$ are independently selected from the group consisting of hydrogen, hydroxyl, halogen, optionally substituted alkoxy, optionally substituted amine, phosphate, optionally substituted alkyl, and optionally substituted acetyl. Preferably, the compound is a tubulin inhibitor.

In some embodiments, the compound is of formula III or its pharmaceutically acceptable salts or prodrugs:

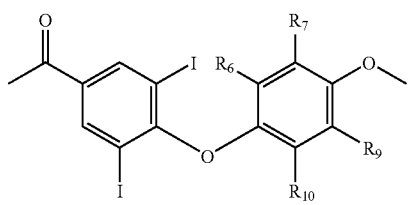

Formula III wherein: $R_6$, $R_7$, $R_9$, and $R_{10}$ are independently selected from the group consisting of hydrogen, hydroxyl, optionally substituted amine, phosphate, and optionally substituted alkyl. Preferably, the compound is a tubulin inhibitor.

In some embodiments, the compound is 1-(4-(3-hydroxy-4-methoxyphenoxy)-3,5-diiodophenyl)ethanone, represented by formula IIIA or its pharmaceutically acceptable salts or prodrugs:

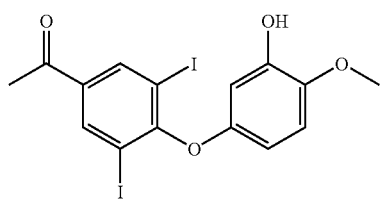

IIIA

In some embodiments, the compound is 1-(4-(3-amino-4-methoxyphenoxy)-3,5-diiodophenyl)ethanone 1-(4-(3-amino-4-methoxyphenoxy)-3,5-diiodophenyl)ethanone, represented by formula IIIB or its pharmaceutically acceptable salts or prodrugs:

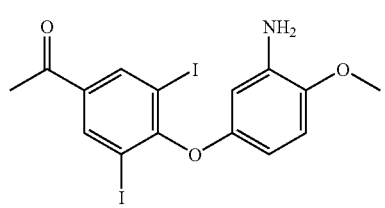

IIIB

In some embodiments, the compound is 1-(4-(2-amino-4-methoxyphenoxy)-3,5-diiodophenyl)ethanone, represented by formula IIIC or its pharmaceutically acceptable salts or prodrugs:

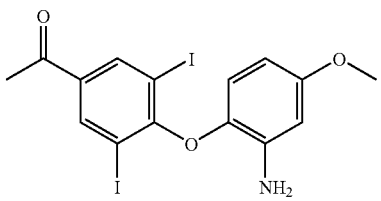

IIIC

In some embodiments, the compound is mono (5-methoxy-3-(4-acetyl-2,6-iodophenoxy)phenyl) phosphoric acid ester, represented by formula IIID or its pharmaceutically acceptable salts or prodrugs:

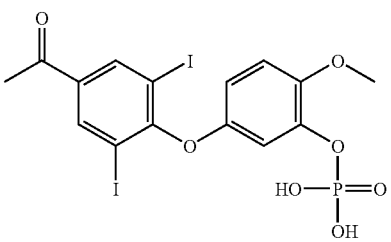

IIID

In some embodiments of the aforementioned aspect of the invention, the optionally substituted alkyl is substituted with an optionally substituted heterocyclic. In some embodiments, the optionally substituted heterocyclic is for example, azeridine, azetidine, pyrrole, dihydropyrrole, pyrrolidene, pyrazole, pyrazoline, pyrazolidine, imidazole, benzimidazole, triazole, tetrazole, oxazole, isoxazole, benzoxazole, oxadiazole, oxazoline, oxazolidine, thiazole, isothiazole, pyridine, dihydropyridine, tetrahydropyridine, quinazoline, pyrazine, pyrimidine, pyridazine, quinoline, isoquinoline, triazine, tetrazine, and piperazine. In some embodiments, the compound is 1-(4-(2-(N-piperazinylprop-3-yl))-4-methoxyphenoxy)-3,5-diiodophenyl)ethanone, represented by formula IIIE or its pharmaceutically acceptable salts or prodrugs:

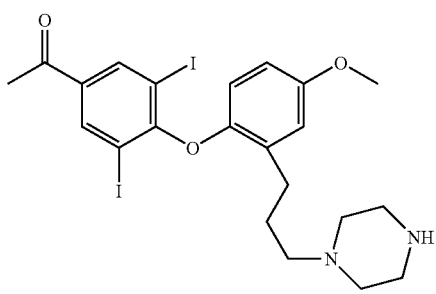

IIIE

Some embodiments of the aforementioned aspect of the present invention relate to a pharmaceutical composition comprising an effective amount of at least one compound of the present invention and a pharmaceutically acceptable carrier.

Some embodiments provide a process of manufacturing a compound of formula IIIB or its pharmaceutically acceptable salts or prodrugs:

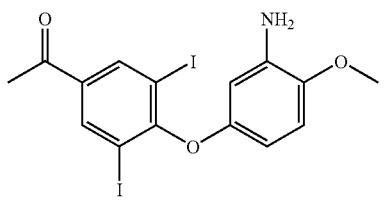

IIIB

The process comprises: (a) nitrating 1-(3,5-diiodo-4-(4-methoxyphenoxy)phenyl)ethanone to form as an intermediate 1-(3,5-diiodo-4-(4-methoxy-3-nitrophenoxy)phenyl)ethanone; and (b) reducing the intermediate of step (a) to form the compound of formula IIIB. In some embodiments, the nitrating is carried out in the presence of nitric acid and concentrated sulfuric acid in an organic solvent. In some embodiments, the organic solvent is methylene chloride. In some embodiments, the reducing is carried out in the presence of tin(II)chloride.

Some embodiments of the invention provide a process of manufacturing a compound of formula IIIA or its pharmaceutically acceptable salts or prodrugs:

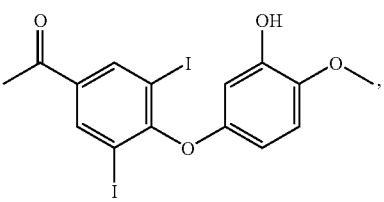

IIIA

The process comprises: (a) reacting a compound of formula IIIB or its pharmaceutically acceptable salts or prodrugs:

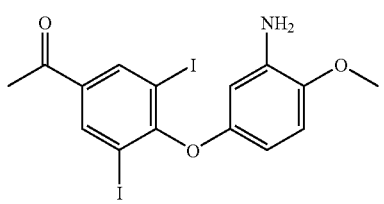

IIIB with a metal nitrate in the presence of a strong acid to form a diazonium intermediate; and (b) refluxing the diazonium intermediate in the presence of a strong acid to form the compound of formula IIIA. In some embodiments, the metal nitrate is sodium nitrate. In some embodiments, the strong acid of step (a) is sulfuric acid. In some embodiments, the strong acid of step (b) is sulfuric acid. In some embodiments, the strong acid of step (a) and step (b) is sulfuric acid.

Other aspects, characteristics and advantages will become clear upon consideration of the instant disclosure, including the appended drawings and original claims.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
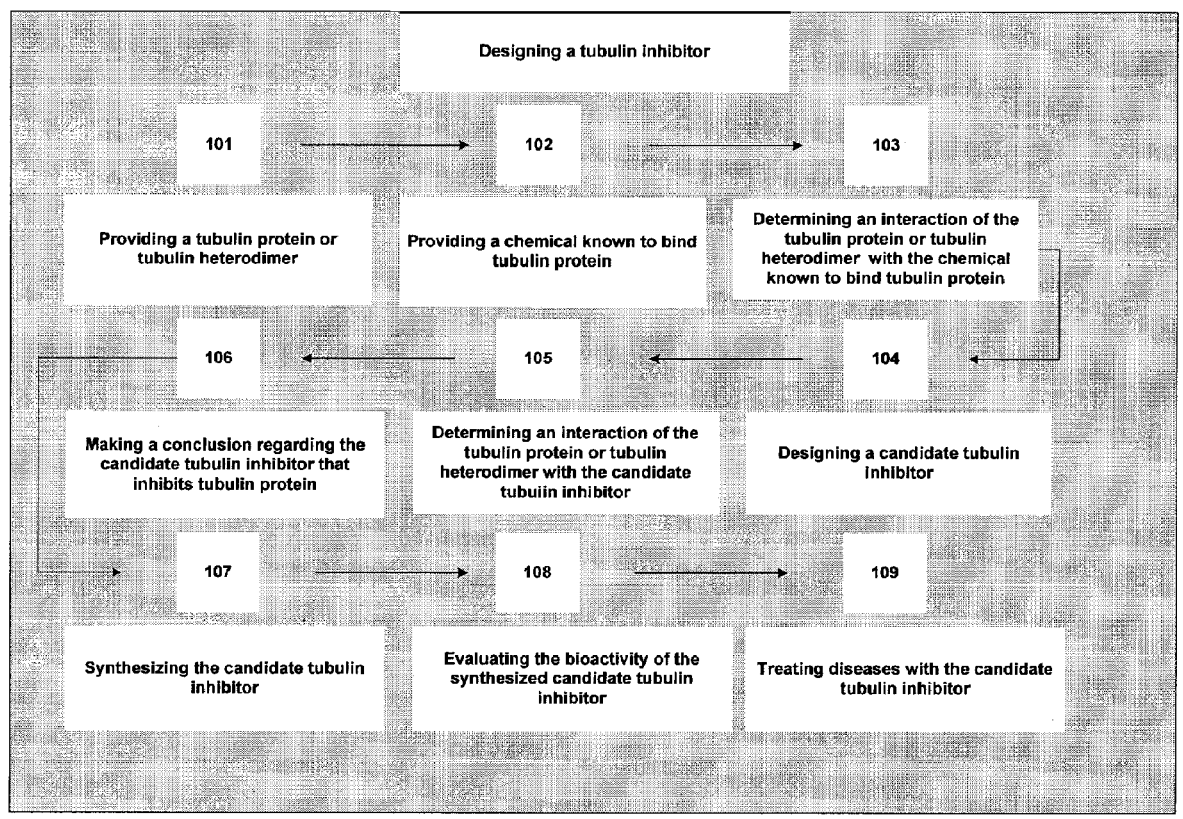
FIG. 1 is a flow chart showing the steps of the methods as disclosed herein.

Definitions:

The term, "aryl" refers to optionally substituted mono- or bicyclic aromatic rings containing only carbon atoms. The term can also include phenyl group fused to a monocyclic cycloalkyl or monocyclic cycloheteroalkyl group in which the point of attachment is on an aromatic portion. Examples of aryl groups include, e.g., phenyl, naphthyl, indanyl, indenyl, tetrahydronaphthyl, 2,3-dihydrobenzofuranyl, dihydrobenzopyranyl, 1,4-benzodioxanyl, and the like.

The term, "heterocyclic" refers to an optionally substituted mono- or bicyclic aromatic ring containing at least one heteroatom (an atom other than carbon), such as N, O and S, with each ring containing about 5 to about 6 atoms. Examples of heterocyclic groups include, e.g., pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

The term, "computer system" as used herein, means the hardware means, software means and data storage means used to perform method of the present invention. Preferably, the computer system is used to analyze atomic coordinate data. The minimum hardware means of the computer-based systems of the present invention comprises a central processing unit (CPU), input means, output means and data storage means. Desirably a monitor is provided to visualize the structure data. The computer can be a stand-alone, or connected to a network and/or shared server. The data storage means can be RAM or means for accessing computer readable media of the invention.

The term, "computer readable media" as used herein, means any media which can be read and accessed by a computer, for example, the media is suitable for use in the above-mentioned computer system. The media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

The term "inhibit" of its grammatical equivalent, such as "inhibitory," is not intended to require complete reduction in biological activity, preferably, tubulin activity. Such reduction is preferably by at least about 50%, at least about 75%, at least about 90%, and more preferably by at least about 95% of the activity of the molecule in the absence of the inhibitory effect, e.g., in the absence of a tubulin inhibitor as disclosed in the invention. Most preferably, the term refers to an observable or measurable reduction in activity. In treatment scenarios, preferably the inhibition is sufficient to produce a therapeutic and/or prophylactic benefit in the condition being treated.

The term "model" or its grammatical equivalents, such as, "modeling" as used herein, means the quantitative and qualitative analysis of molecular structure and/or function based on atomic structural information and interaction models. The term "modeling" includes for example, conventional numeric-based molecular dynamic and energy minimization models, interactive computer graphic models, modified molecular mechanics models, distance geometry and other structure-based constraint models.

The term "pharmaceutically acceptable salt" as used herein, means those salts which retain the biological effectiveness and properties of the compounds of the present invention, and which are not biologically or otherwise undesirable.

The term "substituted" includes single or multiple degrees of substitution by a named substituent.

The term "candidate tubulin inhibitor" as used herein, means any compound which is potentially capable of associating with any of the alpha, beta, or gamma tubulin proteins, and/or inhibiting tubulin protein activity and/or the ability of tubulin protein to interact with another molecule or to form microtubule polymers. The candidate compound may be designed or obtained from a library of compounds which may comprise peptides, as well as other compounds, such as small organic molecules and particularly new lead compounds. By way of example, the candidate compound may be a natural substance, a biological macromolecule, or an extract made from biological materials such as bacteria, fungi, or animal (particularly mammalian) cells or tissues, an organic or an inorganic molecule, a synthetic test compound, a semi-synthetic test compound, a carbohydrate, a monosaccharide, an oligosaccharide or polysaccharide, a glycolipid, a glycopeptide, a saponin, a heterocyclic compound, a structural or functional mimetic, a peptide, a peptidomimetic, a derivatized test compound, a peptide cleaved from a whole protein, or a peptides synthesized synthetically (such as, by way of example, either using a peptide synthesizer or by recombinant techniques or combinations thereof), a recombinant test compound, a natural or a non-natural test compound, a fusion protein or equivalent thereof and mutants, derivatives or combinations thereof.

The term "treating" or its grammatical equivalents as used herein, means achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "anti-vascular" refers to an agent or method that reduces the amount of blood vessels supplying a tumor that exist before or immediately before the administration of the agent or the implementation of the method.

The term "tubulin heterodimer" refers to an alpha tubulin protein and beta tubulin protein subunit complex, comprising the building blocs for microtubule polymerization.

The term "thyroid hormone analogue" or "thyroid hormone/analogue" include both naturally-occurring thyroid hormones such as thyroxine, and chemicals similar in structure to the naturally-occurring thyroid hormones. The chemicals that are similar in structure to the naturally-occurring thyroid hormones may have similar or different biological and pharmacological properties as compared to the naturally-occurring thyroid hormones.

The term "tubulin protein" includes single tubulin gene products, variants, or splice variants thereof, and also includes tubulin protein heterodimers such as, but not limited to, heterodimers of the alpha and beta tubulin protein gene products.

The term "tubulin inhibitor" includes any agent that inhibits the biological activity of a tubulin protein, and includes analogues of thyroxine.

Methods for a Design of a Tubulin Inhibitor

One aspect of the present invention relates to methods for design of a tubulin inhibitor. In some preferred embodiments, the designing comprises using computer modeling techniques. In particular, the present invention relates to a computer-assisted method of a design of a tubulin inhibitor comprising: a) determining an interaction between a tubulin protein and a chemical known to bind the tubulin protein by evaluating a binding of the tubulin protein to the chemical known to bind the tubulin protein; b) based on the interaction, designing a candidate tubulin inhibitor; c) determining an interaction between the tubulin protein and the candidate tubulin inhibitor by evaluating a binding of the tubulin protein to the candidate tubulin inhibitor; and d) concluding that the candidate tubulin inhibitor inhibits the tubulin protein wherein the conclusion is based on the interaction of step c).

In some preferred embodiments, a three-dimensional structure comprising a tubulin protein and a three-dimensional structure of the chemical is used for determining an interaction between the tubulin protein and the chemical. In some preferred embodiments, a three dimensional structure of a binding domain of a tubulin protein is modeled using a crystal of alpha and beta tubulin protein heterodimers through x-ray crystallographic techniques. Preferably, the tubulin protein is the alpha-tubulin/beta tubulin heterodimer. A three dimensional structure of a known tubulin inhibitor or thyroid hormone analogue is modeled based on techniques known in the art. The three dimensional structure of a known tubulin inhibitor or thyroid hormone is allowed to interact with the three dimensional structure of a binding domain of the tubulin protein. Various tubulin inhibitors and thyroid hormone analogues are known in the art and are within the scope of the present invention. Some of the examples of the known tubulin inhibitors and thyroid hormone analogues include, but are not limited to, vinblastine, vincristine, vinorelbine, paclitaxel, docetaxel, colchicine, and thyroxine. In some preferred embodiments of the present invention, the known tubulin inhibitor is colchicine. In another preferred embodiment of the present invention, the thyroid hormone analogue is thyroxine.

An interaction between the tubulin protein or tubulin protein heterodimer and the known tubulin inhibitor or thyroid hormone analogue is determined based on an evaluation of a three dimensional structure of domains of a tubulin protein bound to the known tubulin inhibitor or thyroid hormone analogue. The evaluation can comprise evaluation of one or more of steric interactions, van der Waals interactions, electrostatic interactions, solvation interactions, charge interactions, covalent bonding interactions, non-covalent bonding interactions, entropically favorable interactions, enthalpically favorable interactions, or a combination thereof. The techniques for the evaluation of the interaction between the protein and the drug are well known in the art and are well within the scope of the present invention.

Figure 3:
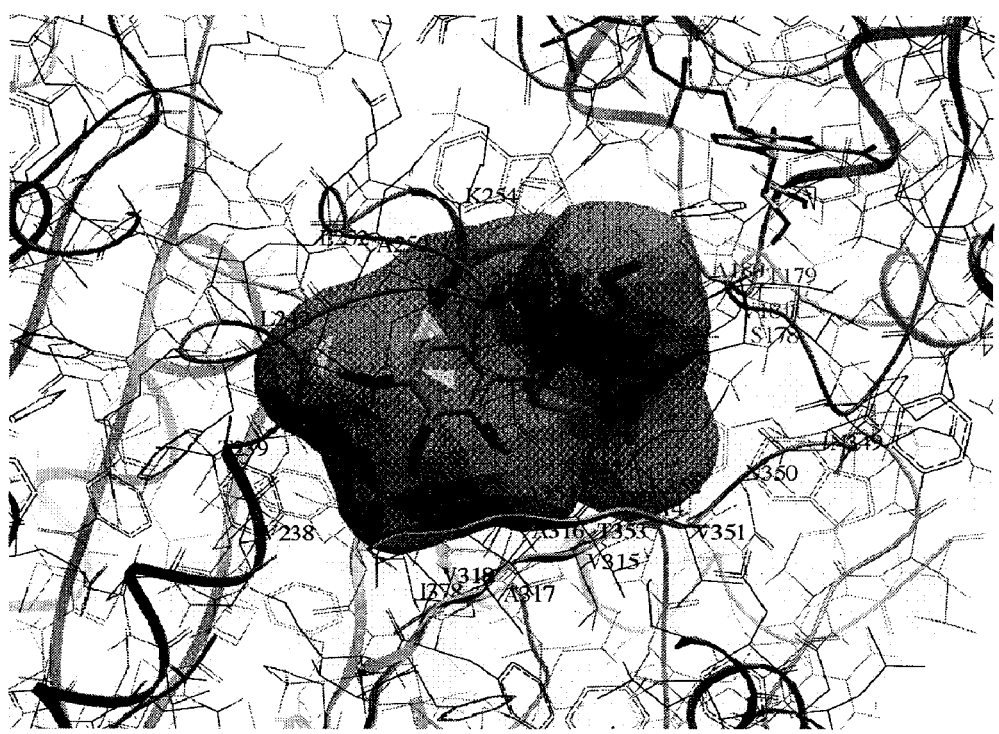
FIG. 3 illustrates a tubulin X-ray structural data analysis.

FIG. 3 illustrates a tubulin X-ray structural data analysis. Small-molecule inhibitor binding pocket in tubulin is shown (green blob). A colchicine molecule bound to the tubulin is shown in stick representation. Surrounding amino-acid residues are labeled, dark blue for beta-tubulin and magenta for alpha-tubulin.

Based on the evaluation of the binding of a known tubulin inhibitor with the tubulin protein, a candidate tubulin inhibitor can be designed. Preferably, the candidate tubulin inhibitor is designed using computer modeling. In some preferred embodiments, the candidate tubulin inhibitor is an analogue of the known tubulin inhibitor. In still further preferred embodiments, the candidate tubulin inhibitor is an analogue of the colchicine. In still further preferred embodiments, the candidate tubulin inhibitor is an analogue of the thyroid hormone thyroxine. A candidate tubulin inhibitor can be designed in such a way that it fits equally or more efficiently in the binding domain of the tubulin protein as compared to the known tubulin inhibitor or thyroid hormone analogue.

Figure 4A:
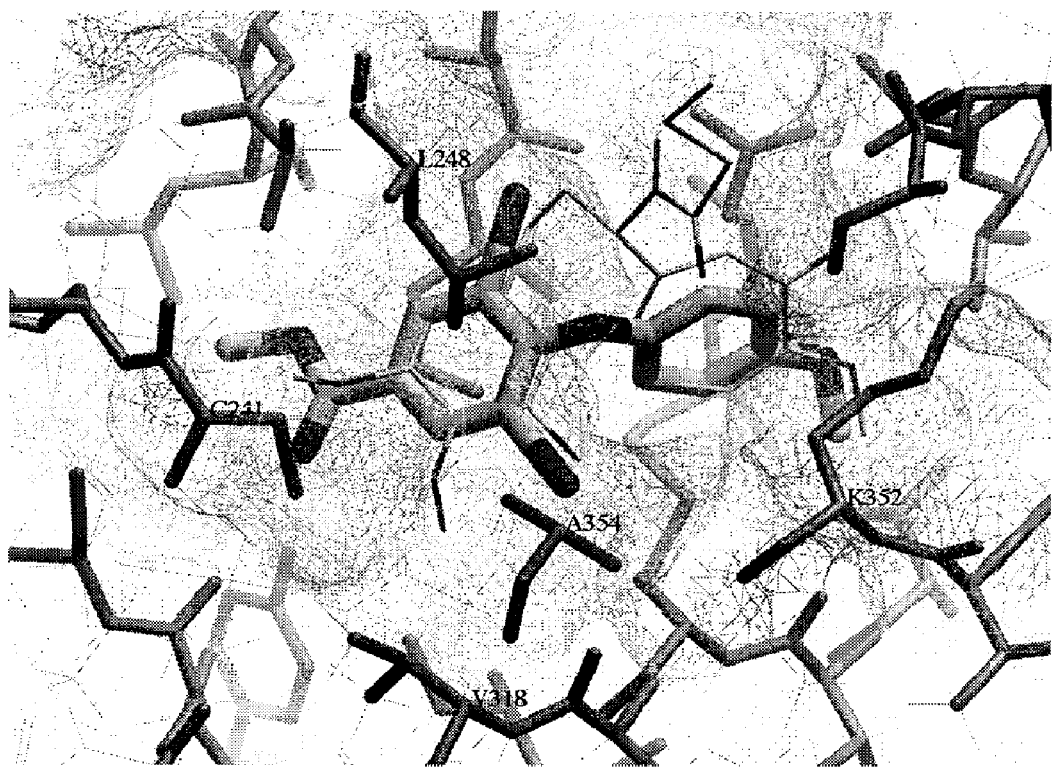
FIG. 4A illustrates a binding pose of methyl 3,5-diiodo-4-(4'-methoxyphenoxy)-benzoate (as thick sticks) in tubulin. A bound conformation of colchicine from experimentally determined structure is superimposed (thin sticks).
Figure 4B:
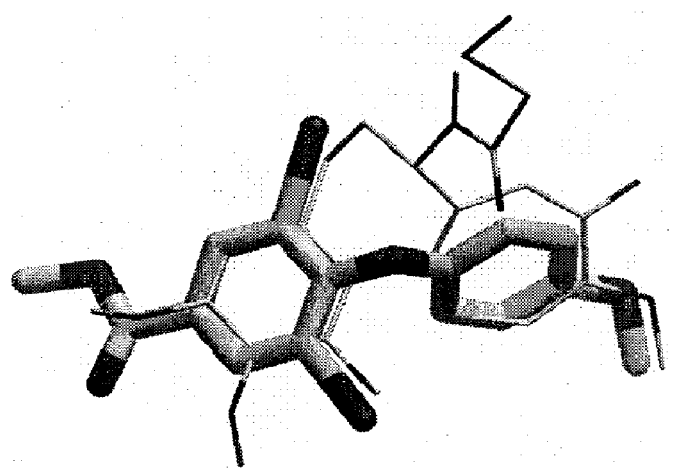
FIG. 4B depicts the methyl 3,5-diiodo-4-(4'-methoxyphenoxy)-benzoate as thick sticks and colchicine as thin sticks.

FIG. 4A illustrates a binding pose of methyl 3,5-diiodo-4-(4'-methoxyphenoxy)-benzoate (as thick sticks) in tubulin. A bound conformation of colchicine from experimentally determined structure is superimposed (thin sticks). FIG. 4B depicts the methyl 3,5-diiodo-4-(4'-methoxyphenoxy)-benzoate as thick sticks and colchicine as thin sticks. The compound structures are converted to 3D and docked into tubulin binding pocket using Molsoft's ICM-Dock.

Figure 5:
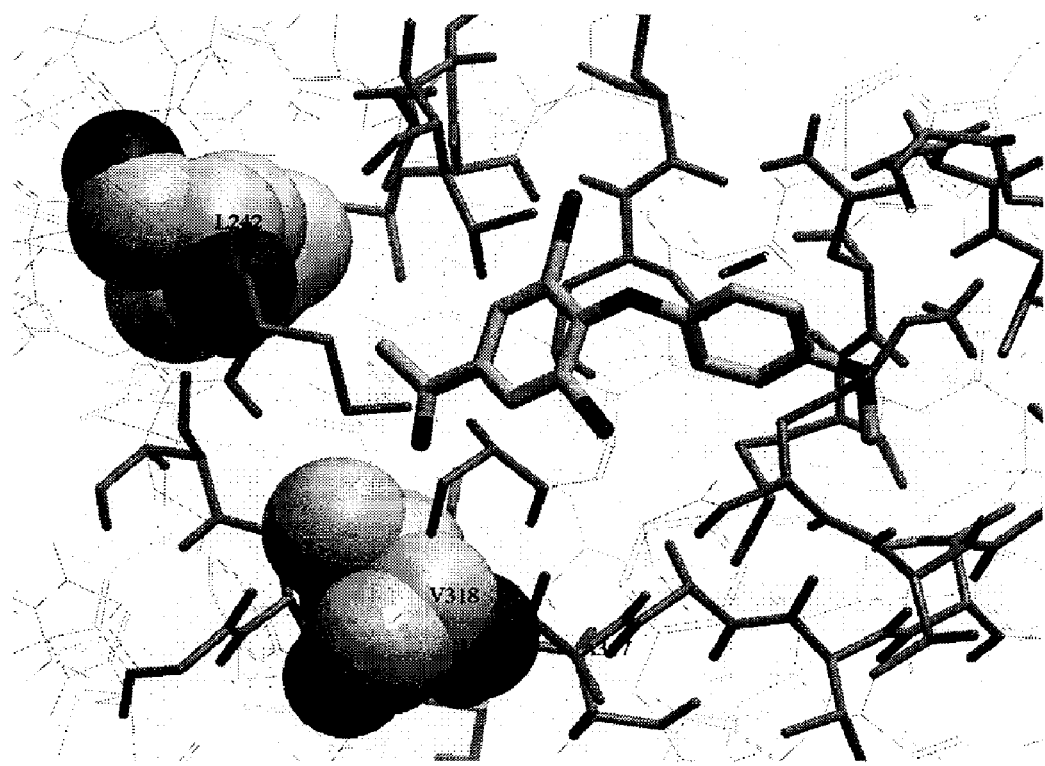
FIG. 5 illustrates a binding of the tubulin inhibitor with at least two residues that differ between isotypes.

FIG. 5 illustrates at least two residues that differ between isotypes (in particular isotype III). The two isotypes are in contact with the inhibitors. Differential affinity of tubulin inhibitors to isotypes may be important for efficacy. For example, isotype 3 may be at least partially responsible for taxol resistance.

After the designing of the candidate tubulin inhibitor, an interaction between the tubulin protein or tubulin protein heterodimer and the candidate tubulin inhibitor can be determined based on an evaluation of the three dimensional structure of the domains of the tubulin protein or tubulin protein heterodimer bound to the candidate tubulin inhibitor. The evaluation can comprise evaluation of one or more of steric interactions, van der Waals interactions, electrostatic interactions, solvation interactions, charge interactions, covalent bonding interactions, non-covalent bonding interactions, entropically favorable interactions, enthalpically favorable interactions, or a combination thereof. Based on the evaluation a conclusion can be made regarding the candidate tubulin inhibitor that inhibits tubulin protein function.

Alternatively, the tubulin protein or tubulin heterodimer complex can be co-crystallized with a candidate tubulin inhibitor in order to provide a crystal suitable for determining the structure of the complex. A crystal of the tubulin protein or tubulin heterodimer complex can be soaked in a solution containing the candidate tubulin inhibitor in order to form co-crystals by diffusion of the candidate tubulin inhibitor into the crystal of the tubulin protein. In some embodiments, the structure of the tubulin protein or tubulin heterodimer complex obtained in the presence and absence of the candidate tubulin inhibitor can be compared to determine structural information about the tubulin protein, identification of possible binding regions of the tubulin protein and/or determine the interaction between the candidate tubulin inhibitor and the tubulin protein or tubulin heterodimer complex.

The present invention further relates to methods for synthesizing the candidate tubulin inhibitors by conventional synthetic chemistry techniques. These techniques are known in the art and are within the scope of the present invention. The present invention further relates to assessing the bioactivity, such as tubulin inhibiting activity, of the synthesized tubulin inhibitor compounds. The assay techniques for assessing the bioactivity of the candidate tubulin inhibitor are well known in the art and are within the scope of the present invention. Another aspect of the present invention relates to providing methods of treatment of a disease using the tubulin inhibitors. Preferably, the disease is a condition that is related to tubulin function.

The steps to some of the preferable methods of the present invention are depicted in FIG. 1. Without limiting the scope of the present invention, the steps can be performed independent of each other or one after the other. One or more steps can be skipped in the methods of the present invention. A tubulin protein or tubulin heterodimer is provided at step 101. The tubulin protein or tubulin heterodimer may be provided as a three dimensional structure of a binding domain of a tubulin protein or tubulin heterodimer. The three dimensional structure of the tubulin protein or tubulin heterodimer may be modeled from a crystal of tubulin protein or tubulin protein heterodimer using x-ray crystallography. A chemical known to bind the tubulin protein or tubulin heterodimer is provided at step 102. A three dimensional structure of the chemical may be provided. The three dimensional structure of the chemical known to bind the tubulin protein or tubulin heterodimer may be provided by a computer modeling technique. An interaction between the tubulin protein or tubulin heterodimer and the chemical known to bind the tubulin protein or tubulin heterodimer can be determined based on the evaluation of the three dimensional structure of the binding domain of the tubulin protein or tubulin protein heterodimer bound to the chemical known to bind the tubulin protein or tubulin heterodimer at step 103. Based on the evaluation, a candidate tubulin inhibitor can be designed at step 104. The candidate tubulin inhibitor can be designed by computer modeling. An interaction between the tubulin protein or tubulin heterodimer and the candidate tubulin inhibitor can be determined based on the evaluation of the three dimensional structure of the binding domain of the tubulin protein or tubulin protein heterodimer bound to the candidate tubulin inhibitor at step 105. Based on this evaluation, a conclusion can be made regarding a candidate tubulin inhibitor that inhibits tubulin protein function at step 106. Further, the candidate tubulin inhibitor that inhibits tubulin protein can be chemically synthesized at step 107. The chemically synthesized candidate tubulin inhibitor can be assayed for its bioactivity, preferably, activity in inhibiting tubulin function at step 108. The candidate tubulin inhibitor that inhibits tubulin protein or tubulin protein heterodimer can be used for treating diseases at step 109. It shall be understood that the invention includes other methods not explicitly set forth herein.

Tubulin and Microtubules

Tubulin is a protein that comprises cellular microtubules. Two distinct tubulin proteins, the alpha and beta protein subunits form heterodimers that form polymers that in turn form the hollow cylinders that make up the microtubular structure. Both the alpha and beta protein subunits bind guanosine triphosphate ("GTP"), but only the beta protein subunit hydrolyzes GTP to guanosine diphosphate ("GDP"). The molecular weight of the alpha and beta protein subunits is approximately 55 kilodaltons ("kDa") each.

Microtubules are comprised of polymers of alpha/beta tubulin heterodimers, and form one of the components of the cell's cytoskeleton. They have a hollow cylindrical shape and their functions include, but are not limited to, cell motility, maintenance of cell shape, intracellular transport, and chromosomal segregation during mitosis. Microtubules grow through polymerization and nucleate in a microtubule organizing center. In these centers, an additional type of tubulin protein, the gamma-tubulin, interacts with several other proteins and forms a ring structure called the "gamma-tubulin ring complex," which helps to provide scaffolding for polymerization.

During polymerization, the microtubule grows by adding more alpha/beta heterodimers onto the "cap" or end of the microtubule. The cap of the microtubule contains at least one alpha/beta heterodimer bound to GTP. Because GDP-bound alpha/beta heterodimers at the cap tend to depolymerize from the microtubule, the GTP-bound cap provides protection against depolymerization, even though alpha/beta lower down the polymer are GDP-bound. Eventually, the GTP in the cap is hydrolyzed, creating depolymerization of the microtubule and accounting for the equilibrium between microtubule formation and depolymerization in cells.

Binding Domains of Tubulin

There are three drug families that target tubulin's function, and therefore at least three binding sites have been described (for a review, see Downing et al., 1999, Cell Structure and Function, 24:269-71). These include, but are not limited to, the colchicine binding site, the vinca alkaloid binding site, and the paclitaxel binding site. At least two binding sites have been characterized as sites that induce destabilization of microtubular polymers: the colchicine and vinca alkaloid binding sites. The paclitaxel binding site has been connected to increased microtubular polymer stability, and both stability and depolymerization have been shown to cause cell death.

The colchicine binding site is approximately in the dimer's middle, near the interface of the alpha and beta tubulin proteins. It also appears to be on the side of the heterodimer that faces the microtubular luminal surface. The vinca alkaloid binding site is located near the longitudinal inter-dimer surface, and is near the GTP/GDP nucleotide binding site. The paclitaxel binding site is on the beta protein subunit of the dimer, and appears to be involved in dimer interfacing with other polymer strand dimers. Therefore, it is thought to be involved with polymer strand lateral interaction, possibly strengthening it, since it has a polymerization-stabilizing function.

Crystal Structure of Tubulin

Alpha and beta heterodimers of tubulin comprise the structural subunit of microtubules, and this subunit's crystal structure has been reported, with crystals induced using zinc (see Nogales et al, 1998, Nature, 391:199-202). One embodiment of the invention utilizes the techniques described therein to crystallize tubulin protein or tubulin heterodimers with which to determine the atomic coordinates. In one embodiment of the invention, the structures of alpha and beta tubulin proteins are very similar as each protein has a core of two beta-sheets surrounded by alpha-helices. In another embodiment, each monomer has at least three functional domains including, but not limited to, the amino-terminal domain (which contains the GTP/GDP nucleotide binding region, the vinca alkaloid binding-domains, and the colchicine binding domain), the intermediate domain (which contains the paclitaxel-binding domain), and the carboxy-terminal domain (which is thought to contain the binding regions for motor proteins).

Examples of methods for determining structure information of tubulin protein, tubulin protein heterodimer, or either bound with a inhibitor include: 1) mass spectrometry to determine one or more properties of a protein, including primary sequence, post translation modification, protein-small molecule interaction, or protein-protein interaction ability; 2) NMR, including ID NMR, multidimensional NMR, and multinuclear NMR, such as $^{15}N/^{1}H$ HSQC spectra, to determine one or more properties of a protein including three dimensional structure, conformational states, aggregation level, state of protein folding or unfolding, or the dynamic properties of the protein; and 3) x-ray crystallography to determine one or more properties of a protein, including three dimensional structure, diffraction of its crystal form or its space group. The present invention preferably uses x-ray crystallography to determine the structural characteristics of the of tubulin protein or tubulin heterodimer. In particular, x-ray diffraction of a crystallized form of the of tubulin protein or tubulin heterodimer can be used to determine the three dimensional structure of the of tubulin protein or tubulin heterodimer.

Crystals of tubulin protein or tubulin heterodimer can be produced or grown by a number of techniques including batch crystallization, vapor diffusion (either by sitting drop or hanging drop), soaking, and by microdialysis. Seeding of the crystals in some instances can be required to obtain x-ray quality crystals. Standard micro and/or macro seeding of crystals can be used. Preferably, the crystal diffracts x-rays for the determination of the atomic coordinates of the of tubulin protein or tubulin heterodimer to a resolution greater than 5.0 Angstroms, alternatively greater than 3.0 Angstroms, or alternatively greater than 2.0

Crystals can be grown from a solution containing a purified tubulin protein or tubulin heterodimer, or a fragment thereof (e.g., a stable domain), by a variety of conventional processes (McPherson, 1982 John Wiley, New York; McPherson, 1990, *Eur. J. Biochem.* 189: 1-23; Webber. 1991, *Adv. Protein Chem.* 41:1-36). In some embodiments, native crystals of the tubulin protein or tubulin heterodimer can be grown by adding precipitants to the concentrated solution of the tubulin protein or tubulin heterodimer. The precipitants can be added at a concentration just below that necessary to precipitate the tubulin protein or tubulin heterodimer. Water can be removed by controlled evaporation to produce precipitating conditions, which are maintained until crystal growth ceases. The formation of crystals can depend on various factors including pH, temperature, tubulin protein or tubulin heterodimer concentration, the nature of the solvent and precipitant, as well as the presence of added ions or ligands to the tubulin protein or tubulin heterodimer. In addition, the sequence of the tubulin protein or tubulin heterodimer being crystallized can have an effect on the success of obtaining crystals. Many routine crystallization experiments can be needed to screen all these factors for the few combinations that might give crystal suitable for x-ray diffraction analysis. Crystallization robots can automate and speed up the work of reproducibly setting up large number of crystallization experiments. Once the conditions for growing the crystal are optimized, variations of the condition can be systematically screened in order to find the set of conditions which allow the growth of sufficiently large, single, well ordered crystals. In some embodiments, the tubulin protein or tubulin heterodimer can be co-crystallized with a compound that stabilizes the tubulin protein or tubulin heterodimer.

Before the data collection, the tubulin protein or tubulin heterodimer crystal can be frozen to protect it from radiation damage. A number of different cryo-protectants can be used to assist in freezing the crystal, such as methyl pentanediol (MPD), isopropanol, ethylene glycol, glycerol, formate, citrate, mineral oil, or a low-molecular-weight polyethylene glycol (PEG). As an alternative to freezing the crystal, the crystal can also be used for diffraction experiments performed at temperatures above the freezing point of the solution. In these instances, the crystal can be protected from drying out by placing it in a narrow capillary of a suitable material (generally glass or quartz) with some of the crystal growth solution included in order to maintain vapor pressure.

X-ray diffraction results can be recorded by a number of ways know to one of skill in the art. Examples of area electronic detectors include charge coupled device detectors, multi-wire area detectors and phosphoimager detectors (Amemiya, Y, 1997. *Methods in Enzymology*, Vol. 276. Academic Press, San Diego, pp. 233-243; Westbrook, E. M., Naday, 1. 1997. *Methods in Enzymology*, Vol. 276. Academic Press, San Diego, pp. 244-268; 1997. Kahn, R. & Fourme, R. *Methods in Enzymology*, Vol. 276. Academic Press, San Diego, pp. 268-286). Collection of X-ray diffraction patterns are well known by those skilled in the art and are within the scope of the present invention.

Modeling of the three dimensional structure of the tubulin protein or tubulin heterodimer can be accomplished by either the crystallographer using a computer graphics program such as TURBO or O (Jones, T A. et al., *Acta Crystallogr*. A47, 100-119, 1991) or, under suitable circumstances, by using a fully automated model building program, such as WARP (Anastassis et al. *Nature Structural Biology*, May 1999 Volume 6 Number 5 pp 458-463) or MAID (Levitt, D. G., *Acta Crystallogr*. D 2001 V57: 1013-9). This structure can be used to calculate model-derived diffraction amplitudes and phases.

The three dimensional structure of the crystal of the tubulin protein or tubulin heterodimer can be modeled using molecular replacement. The term "molecular replacement" refers to a method that involves generating a preliminary model of a molecule or complex whose structure coordinates are unknown, by orienting and positioning a molecule whose structure coordinates are known within the unit cell of the unknown crystal, so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, more accurate structure of the unknown crystal.

Homology modeling (also known as comparative modeling or knowledge-based modeling) methods can also be used to develop a three dimensional structure of the tubulin protein or tubulin heterodimer. The method utilizes a computer model of a known protein, a computer representation of the amino acid sequence of the polypeptide (e.g., tubulin protein or tubulin heterodimer) with an unknown structure, and standard computer representations of the structures of amino acids. This method is well known to those skilled in the art (Greer, 1985, *Science* 228, 1055; Bundell et al 1988, *Eur. J. Biochem.* 172, 513).

A three dimensional structure of the tubulin protein or tubulin heterodimer can be described by the set of atoms that best predict the observed diffraction data. Files can be created for the structure that defines each atom by its chemical identity, spatial coordinates in three dimensions, root mean squared deviation from the mean observed position and fractional occupancy of the observed position. Hydrogen bonds and other atomic interactions, both within the protein and to bound ligands, can be identified. A model can represent the secondary, tertiary and/or quaternary structure of the tubulin protein or tubulin heterodimer. The model itself can be in two or three dimensions.

It is known in the art that a set of structure coordinates for a protein, complex or a portion thereof, is a relative set of points that define a shape in three dimensions. Thus, it is possible that an entirely different set of coordinates could define a similar or identical shape. Moreover, slight variations in the individual coordinates can have little effect on overall shape. Such variations in coordinates can be generated because of mathematical manipulations of the structure coordinates. For example, structure coordinates could be manipulated by crystallographic permutations of the structure coordinates, fractionalization of the structure coordinates, integer additions or subtractions to sets of the structure coordinates, inversion of the structure coordinates or any combination of the above.

The three-dimensional structure of a tubulin protein or tubulin heterodimer, a known tubulin inhibitor or thyroid hormone/analogue, a candidate tubulin inhibitor, or a tubulin protein/tubulin heterodimer bound to a known tubulin inhibitor or thyroid hormone/analogue or a candidate tubulin inhibitor (tubulin protein-tubulin inhibitor complex), can be determined by conventional means as described above or as known in the art. The structure factors from the three-dimensional structure coordinates of tubulin protein or tubulin heterodimer can be utilized to aid the structure determination of the tubulin protein-tubulin inhibitor complex. Structure factors include mathematical expressions derived from three-dimensional structure coordinates of the tubulin protein or tubulin heterodimer. These mathematical expressions include, for example, amplitude and phase information. The three-dimensional structure of the tubulin protein or tubulin heterodimer, a known tubulin inhibitor or thyroid hormone/ analogue, a candidate tubulin inhibitor or a tubulin protein or tubulin heterodimer-tubulin inhibitor complex can be determined using molecular replacement analysis. This analysis utilizes a known three-dimensional structure as a search model to determine the structure of a closely related tubulin protein or tubulin heterodimer, a known tubulin inhibitor or thyroid hormone/analogue, a candidate tubulin inhibitor or a tubulin protein or tubulin heterodimer-tubulin inhibitor complex.

In some embodiments, the tubulin protein or tubulin heterodimer can be soluble, purified and/or isolated tubulin protein or tubulin heterodimer which can optionally comprise a tag or label to facilitate expression, purification and/or structural or functional characterization. In some embodiments, a tubulin protein or tubulin heterodimer which is used in accordance with the methods of the invention is labeled with an isotopic label to facilitate its detection and or structural characterization using nuclear magnetic resonance or another applicable technique. Exemplary isotopic labels include radioisotopic labels such as, for example, potassium-40 ($^{40}K$), carbon-14 ($^{14}C$), tritium ($^{3}H$), sulfur-35 ($^{35}S$), phosphorus-32 ($^{32}P$), technetium-99m ($^{99}mTc$), thallium-201 ($^{201}Tl$), gallium-67 ($^{67}Ga$), indium-111 ($^{111}In$), iodine-123 ($^{123}I$), iodine-131 ($^{131}I$), yttrium-90 ($^{90}Y$), samarium-153 ($^{153}Sm$), rhenium-186 ($^{186}Re$), rhenium-188 ($^{188}Re$), dysprosium-165 ($^{165}Dy$) and holmium-166 ($^{166}Ho$). The isotopic label can also be an atom with non zero nuclear spin, including, for example, hydrogen-1 ($^{1}H$), hydrogen-2 ($^{2}H$), hydrogen-3 ($^{3}H$), phosphorous-31 ($^{31}p$), sodium-23 ($^{23}Na$), nitrogen-14 ($^{14}N$), nitrogen-15 ($^{15}N$), carbon-13 ($^{13}C$) and fluorine-19 ($^{19}F$).

In certain embodiments, the tubulin protein or tubulin heterodimer is uniformly labeled with an isotopic label, for example, wherein about 50%, 70%, 80%, 90%, 95%, or 98% of the possible labels in the tubulin protein or tubulin heterodimer are labeled, e.g., wherein about 50%, 70%, 80%, 90%, 95%, or 98% of the nitrogen atoms in the tubulin protein or tubulin heterodimer are $^{15}N$, and/or wherein about 50%, 70%, 80%, 90%, 95%, or 98% of the carbon atoms in the tubulin protein or tubulin heterodimer are $^{13}C$, and/or wherein about 50%, 70%, 80%, 90%, 95%, or 98% of the hydrogen atoms in the tubulin protein or tubulin heterodimer are $^{2}H$. In other embodiments, the isotopic label is located in one or more specific locations within the tubulin protein or tubulin heterodimer. The invention also encompasses the embodiment wherein a single tubulin protein or tubulin heterodimer comprises two or more different isotopic labels, for example, the tubulin protein or tubulin heterodimer comprises both $^{15}N$ and $^{13}C$ labeling.

In yet another embodiment, the tubulin protein or tubulin heterodimer which can be used in accordance with the methods of the invention is labeled to facilitate structural characterization using x-ray crystallography or another applicable technique. Exemplary labels include heavy atom labels such as, for example, cobalt, selenium, krypton, bromine, strontium, molybdenum, ruthenium, rhodium, palladium, silver, cadmium, tin, iodine, xenon, barium, lanthanum, cerium, praseodynium, neodymium, samarium, europium, gadolinium, terbium, dysprosium, holmium, erbium, thulium, ytterbium, lutetium, tantalum, tungsten, rhenium, osmium, iridium, platinum, gold, mercury, thallium, lead, thorium and uranium.

Designing a Tubulin Inhibitor

Designing as disclosed in the present invention involves designing a chemical substance, particularly a candidate tubulin inhibitor that interacts in some way with receptor or binding domains of the tubulin protein or tubulin heterodimer. Typically, for a drug to effectively interact with the binding domains of the tubulin protein or tubulin heterodimer, it can be necessary that the three-dimensional shape ("conformation") of tubulin protein or tubulin heterodimer assumes a compatible conformation that allows the drug and the binding domain of the tubulin protein or tubulin heterodimer to fit and bind together in a way that produces a desired result. Preferably, the desired result is an efficient binding of the drug with the tubulin protein or tubulin heterodimer resulting in an inhibition of the tubulin activity. In such instance, the complex shape or conformation of the binding domain of the tubulin protein or tubulin heterodimer can be compared to a "lock", and the corresponding requisite shape or conformation of the drug as a "key" that unlocks (i.e., produces the desired result within) the binding domain of the tubulin protein or tubulin heterodimer. This "lock-and-key" analogy emphasizes that only a properly conformed key (drug patterned thereafter) is able to fit within the lock (the binding domain of the tubulin protein or tubulin heterodimer) in order to "unlock" it (produce a desired result). Further, even if the key fits in the lock, it must have the proper composition in order for it to perform its function. That is, the drug contains the elements in the spatial arrangement and position in order to properly bind with the binding domain of the tubulin protein or tubulin heterodimer. The design as disclosed herein can include knowing or predicting the conformation of the binding domain of the tubulin protein or tubulin heterodimer, and also controlling and/or predicting the conformation of the drug, i.e., a candidate tubulin inhibitor that is to interact with the binding domain of the tubulin protein or tubulin heterodimer.

Determination of the binding domain of the tubulin protein or tubulin heterodimer, and in particular the recognition of the role of domains helps in identifying binding of tubulin inhibitors or thyroid hormone analogues in the binding domains of the tubulin protein or tubulin heterodimer. A known tubulin inhibitor or thyroid hormone analogue is used to evaluate its binding with the binding domain of the tubulin protein or tubulin heterodimer. Based on this evaluation, computational techniques for drug design are used to design candidate tubulin inhibitors based on the structure of a known tubulin inhibitor or thyroid hormone analogue. For example, automated ligand-receptor docking programs which require accurate information on the atomic coordinates of target receptors are used to design candidate tubulin inhibitors. The candidate tubulin inhibitors can be designed de novo or can be analogs of known tubulin inhibitors or thyroid hormone analogues. Preferably, the candidate tubulin inhibitor is designed based on a known tubulin inhibitor or thyroid hormone analogue. More preferably, the candidate tubulin inhibitor is an analogue of thyroxine. Alternatively, the candidate tubulin inhibitors can be synthesized and formed into a complex with tubulin protein or tubulin protein heterodimer, and the complex can then be analyzed by x-ray crystallography to identify the actual position of the bound tubulin inhibitor. The structure and/or functional groups of the candidate tubulin inhibitor can then be adjusted, if necessary, in view of the results of the x-ray analysis, and the synthesis and analysis sequence repeated until an optimized tubulin inhibitor is obtained.

The designing of the candidate tubulin inhibitor can involve computer-based in silico screening of compound databases (such as the Cambridge structural database) with the aim of identifying compounds which interact with the binding cavity or sites of the target tubulin protein or tubulin heterodimer. Screening selection criteria can be based on pharmacokinetic properties such as metabolic stability and toxicity. Determination of the mechanism of the tubulin inhibition allows the architecture and the chemical nature of tubulin binding sites to be better defined, which in turn allows the geometric and functional constraints of a substituent on the candidate tubulin inhibitor to be derived more accurately. The substituent can be a type of virtual 3-D pharmacophore, which can be used as selection criteria or filter for database screening.

In some preferred embodiments of the present invention, the candidate tubulin inhibitor is an analogue of thyroxine. Based on the interaction of the thyroxine with the binding domain of the tubulin protein or tubulin heterodimer, a candidate tubulin inhibitor can be designed.

In some embodiments, the compound is of formula I, its pharmaceutically acceptable salts or prodrugs thereof:

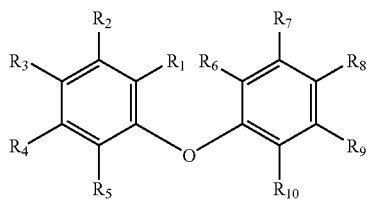

Formula I wherein: $R_1$ and $R_5$ are halogens; $R_2$, $R_3$, and $R_4$ are independently selected from the group consisting of hydrogen, hydroxyl, halogen, ester, optionally substituted alkoxy, optionally substituted amine, phosphate, optionally substituted alkyl, and optionally substituted acetyl; $R_6$, $R_7$, $R_8$, $R_9$, and $R_{10}$ are independently selected from the group consisting of hydrogen, hydroxyl, halogen, optionally substituted alkoxy, optionally substituted amine, phosphate, optionally substituted alkyl, optionally substituted alkenyl, optionally substituted alkynyl, nitroso, carboxyl, optionally substituted cycloalkyl, and optionally substituted heterocyclic. The optionally substituted heterocyclic can be for example, azeridine, azetidine, pyrrole, dihydropyrrole, pyrrolidene, pyrazole, pyrazoline, pyrazolidine, imidazole, benzimidazole, triazole, tetrazole, oxazole, isoxazole, benzoxazole, oxadiazole, oxazoline, oxazolidine, thiazole, isothiazole, pyridine, dihydropyridine, tetrahydropyridine, quinazoline, pyrazine, pyrimidine, pyridazine, quinoline, isoquinoline, triazine, tetrazine, and piperazine. Preferably, the compounds as provided herein are tubulin inhibitors.

In some embodiments of the present invention, the compound is of formula II, its pharmaceutically acceptable salts or prodrugs thereof:

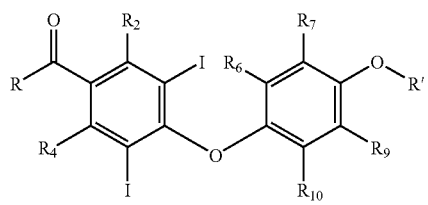

Formula II wherein: R, R', $R_2$, $R_4$, $R_6$, $R_7$, $R_9$, and $R_{10}$ are independently selected from the group consisting of hydrogen, hydroxyl, halogen, optionally substituted alkoxy, optionally substituted amine, phosphate, optionally substituted alkyl, and optionally substituted acetyl. Preferably, the compound is a tubulin inhibitor.

In some embodiments of the present invention, the compound is of formula III, its pharmaceutically acceptable salts or prodrugs thereof:

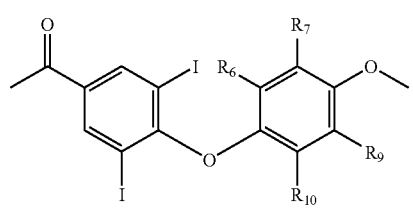

Formula III wherein $R_6$, $R_7$, $R_9$, and $R_{10}$ are independently selected from the group consisting of hydrogen, hydroxyl, optionally substituted amine, phosphate, and optionally substituted alkyl. Preferably, the compound is a tubulin inhibitor.

In some preferred embodiments, the compound is 1-(4-(3-hydroxy-4-methoxyphenoxy)-3,5-diiodophenyl)ethanone, represented by formula IIIA, its pharmaceutically acceptable salts or prodrugs thereof:

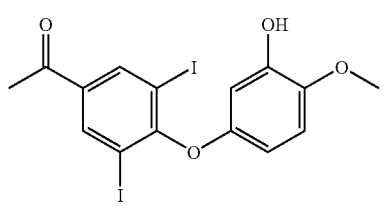

Formula IIIA

In some preferred embodiments, the compound is 1-(4-(3-amino-4-methoxyphenoxy)-3,5-diiodophenyl)ethanone, represented by formula IIIB, its pharmaceutically acceptable salts or prodrugs thereof:

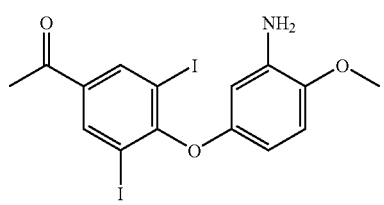

Formula IIIB

In some preferred embodiments, the compound is 1-(4-(2-amino-4-methoxyphenoxy)-3,5-diiodophenyl)ethanone, represented by formula IIIC, its pharmaceutically acceptable salts or prodrugs thereof:

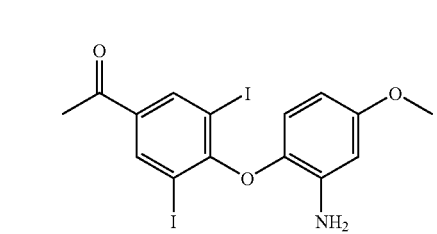

Formula IIIC

In some preferred embodiments, the compound is mono (5-methoxy-3-(4-acetyl-2,6-iodophenoxy)phenyl) phosphoric acid ester, represented by formula IIID, its pharmaceutically acceptable salts or prodrugs thereof:

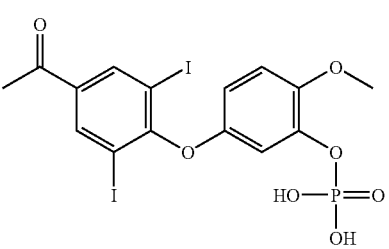

Formula IIID

In some preferred embodiments, the compound is 1-(4-(2-(N-piperazinylprop-3-yl))-4-methoxyphenoxy)-3,5-diiodophenyl)ethanone, represented by formula IIIE, its pharmaceutically acceptable salts or prodrugs thereof:

Formula IIIE

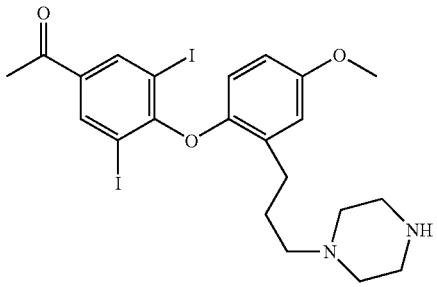

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, turmeric acid, succinic acid, lactic acid, mandelic acid, malic acid, citric acid, tartaric acid or maleic acid. In addition, if the compound(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

The candidate tubulin inhibitors described herein can contain one or more asymmetric centers and thus occur as racemates and racemic mixtures, single enantiomers, individual diastereomers and diastereomeric mixtures. All such isomeric forms of these compounds are expressly included in the present invention. The tubulin inhibitors described herein can also be represented in multiple tautomeric forms, all of which are included herein. The tubulin inhibitors can also occur in cis- or trans- or E- or Z-double bond isomeric forms. All such isomeric forms of such inhibitors are expressly included in the present invention. All crystal forms of the tubulin inhibitors described herein are expressly included in the present invention. The tubulin inhibitors can also be present as their pharmaceutically acceptable salts, derivatives or prodrugs.

The known or a candidate tubulin inhibitor molecule or thyroid analogue can be examined through the use of computer modeling using a docking program such as GRID, DOCK, or AUTODOCK (see Wolfgang B. Fischer, *Anal. Bioanal. Chem.* 2003, 375, 23-25). This procedure can include computer fitting of a three dimensional structure of a known or a candidate tubulin inhibitor molecule to a binding domain of the tubulin protein or tubulin heterodimer to ascertain how well the shape and the chemical structure of the known or the candidate tubulin inhibitor molecule will complement the binding domain of the tubulin protein or tubulin heterodimer. Computer programs can also be employed to estimate the attraction, repulsion, and steric hindrance of the known or the candidate tubulin inhibitor to the binding domain of the tubulin protein or tubulin heterodimer. Typically, the tighter the fit (e.g., the lower the steric hindrance, and/or the greater the attractive force) the more potent the tubulin inhibitor will be since these properties are consistent with a tighter binding constant. Furthermore, the more specificity in the design of a candidate tubulin inhibitor the more likely it can be that the candidate tubulin inhibitor will not interfere with other properties of the tubulin protein or tubulin heterodimer or other proteins. This can minimize potential side-effects due to unwanted interactions with other proteins.

Numerous computer programs are available and suitable for a drug design and the processes of computer modeling, model building, and computationally identifying, selecting and evaluating candidate tubulin inhibitors in the methods described herein. These include, for example, GRID (available form Oxford University, UK), MCSS (available from Molecular Simulations Inc., Burlington, Mass.), AUTODOCK (available from Oxford Molecular Group), FLEX X (available from Tripos, St. Louis. Mo.), DOCK (available from University of California, San Francisco), CAVEAT (available from University of California, Berkeley), HOOK (available from Molecular Simulations Inc., Burlington, Mass.), and 3D database systems such as MACCS-3D (available from MDL Information Systems, San Leandro, Calif.), UNITY (available from Tripos, St. Louis. Mo.), and CATALYST (available from Molecular Simulations Inc., Burlington, Mass.). The computer program that can be used in the present invention is ICM (available from Molsoft LLC, La Jolla, Calif.).

Potential tubulin inhibitors can also be computationally designed "de novo" using such software packages as LUDI (available from Biosym Technologies, San Diego, Calif.), LEGEND (available from Molecular Simulations Inc., Burlington, Mass.), and LEAPFROG (Tripos Associates, St. Louis, Mo.). Compound deformation energy and electrostatic repulsion, can be evaluated using programs such as GAUSSIAN 92, AMBER, QUANTA/CHARMM, AND INSIGHT II/DISCOVER. These computer evaluation and modeling techniques can be performed on any suitable hardware including for example, workstations available from Silicon Graphics, Sun Microsystems, and the like. The computer workstation that can be used in the present invention is Apple Power Mac G5. The techniques, methods, hardware and software as disclosed herein are representative and are not intended to be limiting to the scope of the present invention. Other modeling techniques known in the art can also be employed in accordance with this invention.

Another aspect of the invention relates to a computer system containing a set of information to perform a design of a tubulin inhibitor having a user interface comprising a display unit, the set of information comprising:

a) logic for inputting an information regarding a binding of a tubulin protein to a chemical known to bind tubulin protein;

b) logic for designing a candidate tubulin inhibitor based on the binding of the tubulin protein to the chemical known to bind tubulin protein;

c) logic for determining an information regarding a binding of the tubulin protein to the candidate tubulin inhibitor; and d) logic for making a conclusion regarding a tubulin inhibitory properties of the candidate tubulin inhibitor based on the determination of step c).

Figure 2:
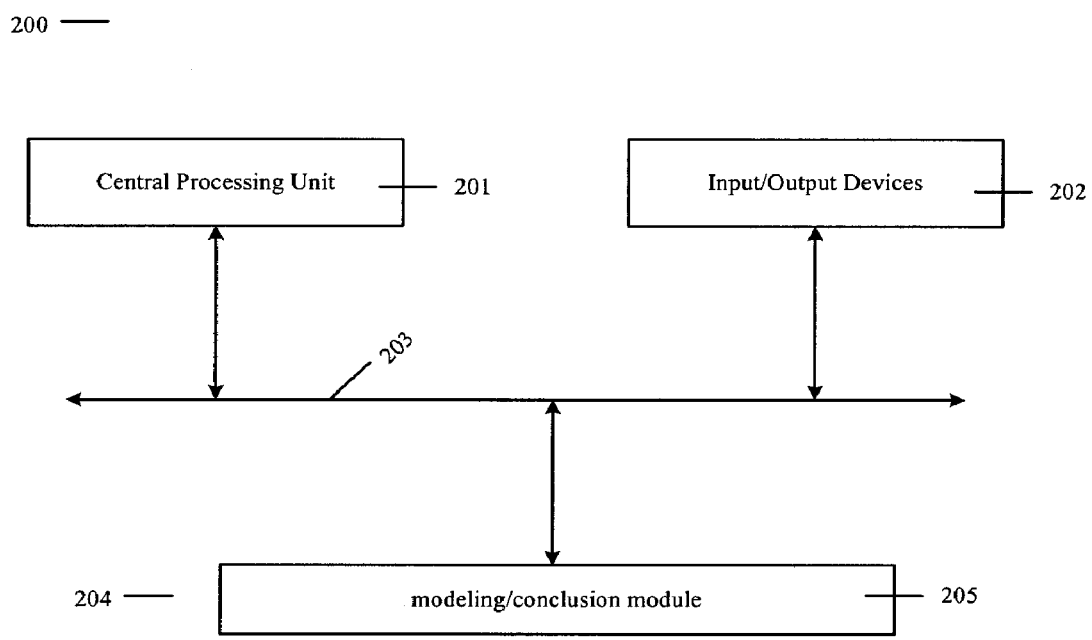
FIG. 2 illustrates a computer for implementing selected operations associated with the methods disclosed herein.

In some preferred embodiments, the steps of the methods of the present invention are performed using a computer as depicted in FIG. 2. FIG. 2 illustrates a computer for implementing selected operations associated with the methods of the present invention. The computer 200 includes a central processing unit 201 connected to a set of input/output devices 202 via a system bus 203. The input/output devices 202 can include a keyboard, mouse, scanner, data port, video monitor, liquid crystal display, printer, and the like. A memory 204 in the form of primary and/or secondary memory is also connected to the system bus 203. These components of FIG. 2 characterize a standard computer. This standard computer is programmed in accordance with the invention. In particular, the computer 200 can be programmed to perform various operations of the methods of the present invention.

The memory 204 of the computer 200 can store a modeling/determining module 205. In other words, the modeling/determining module 205 can perform the operations associated with steps of FIG. 1. The modeling/determining module includes modeling a three dimensional structure of tubulin protein or tubulin heterodimer from a crystal of the tubulin protein or tubulin heterodimer, modeling a three dimensional structure of a binding domain of a tubulin protein or tubulin heterodimer, modeling a three dimensional structure of a known tubulin inhibitor or thyroid hormone analogue, modeling and determining a binding of the three dimensional structure of the binding domain of a tubulin protein or tubulin heterodimer with the tubulin inhibitor or thyroid hormone analogue, modeling a three dimensional structure of a candidate tubulin inhibitor, modeling and determining a binding of the three dimensional structure of the binding domain of the tubulin protein or tubulin heterodimer with the candidate tubulin inhibitor, and evaluating the binding of the known tubulin inhibitor or thyroid hormone analogue or the candidate tubulin inhibitor with the tubulin protein or tubulin heterodimer. The modeling module can also include a conclusion module which includes a conclusion regarding the candidate tubulin inhibitor that inhibits tubulin activity.

The candidate tubulin inhibitor as disclosed herein can be prepared by employing standard synthetic techniques known in the art. The candidate tubulin inhibitors can be analyzed for their bioactivity. Preferably, the bioactivity relates to inhibition of tubulin activity. The compounds which display tubulin inhibiting activity can be candidate tubulin inhibitors, while the compounds which do not display tubulin inhibiting activity help define portions of the molecule which are particularly involved in imparting tubulin inhibiting activity to the candidate tubulin inhibitor. Where analogue compounds are not bioactive, additional analogue compounds can be designed, subjected to the methods of the present invention, and then tested for bioactivity. Additional candidate tubulin inhibitors can be devised by either repeating the above-described process, or seeking to render other portions of the target structure chemically modified.

In some embodiments of the present invention, pertinent physical and chemical properties (i.e., sites of hydrogen bonding, surface area, atomic and molecular volume, charge density, directionality of the charges, etc.) of candidate tubulin inhibitors can be used to develop a collection of parameters required for the desired bioactivity. A database of known compounds (e.g., the Cambridge crystal structure database) can then be searched for structures which contain the steric parameters required for the desired bioactivity. Compounds which are found to contain the desired steric parameters can be retrieved, and further analyzed to determine which of the retrieved compounds also have the desired electronic properties, relative to the candidate tubulin inhibitor. Compounds that are found to contain both the desired steric and electronic properties can be additional candidates as tubulin inhibitors.

Known compounds which also possess the collection of parameters required for the desired bioactivity can then be tested to see if they also possess the desired bioactivity. Alternatively, known compounds which also possess the collection of parameters required for the desired bioactivity can be modified to remove excess functionality which is not required for the particular bioactivity being tested. Such a modified compound can be a simple, readily prepared tubulin inhibitor.

The tubulin inhibitors described herein are also useful for inhibiting the biological activity of any protein comprising greater than 90%, alternatively greater than 85%, or alternatively greater than 70% sequence homology with a tubulin protein sequence. The tubulin inhibitors described herein are also useful for inhibiting the biological activity of any protein comprising a subsequence, or variant thereof, of any protein that comprises greater than 90%, alternatively greater than 85%, or alternatively greater than 70% sequence homology with a tubulin subsequence. Such subsequence preferably comprises greater than 90%, alternatively greater than 85%, or alternatively greater than 70% sequence homology with the sequence of an active site or subdomain of a tubulin protein.

Synthesis Schemes for Candidate Tubulin Inhibitors

The candidate tubulin inhibitor s as disclosed herein can be prepared by employing standard synthetic techniques known in the art and such techniques are within the scope of the present invention. Without limiting the scope of the present invention some of the synthesis schemes for the candidate Tubulin inhibitor s are provided as below.

An example of a synthesis scheme for candidate tubulin inhibitor of a compound of formula IIIA from pyrocatechol (CAS 120-80-9) is as provided below (Evans D. A. et al., *J. Am. Chem. Soc.* 2001, 123, 12411-12413; Evans D. A. et al., *Tetrahedron Lett.* 1998, 39, 2933-2936; Saimoto H. et al., *Tetrahedron Lett.*, 1986, 27, 1607; Covello M. et. al., *Chem. Abstr.* 1962, 56, 5929i).

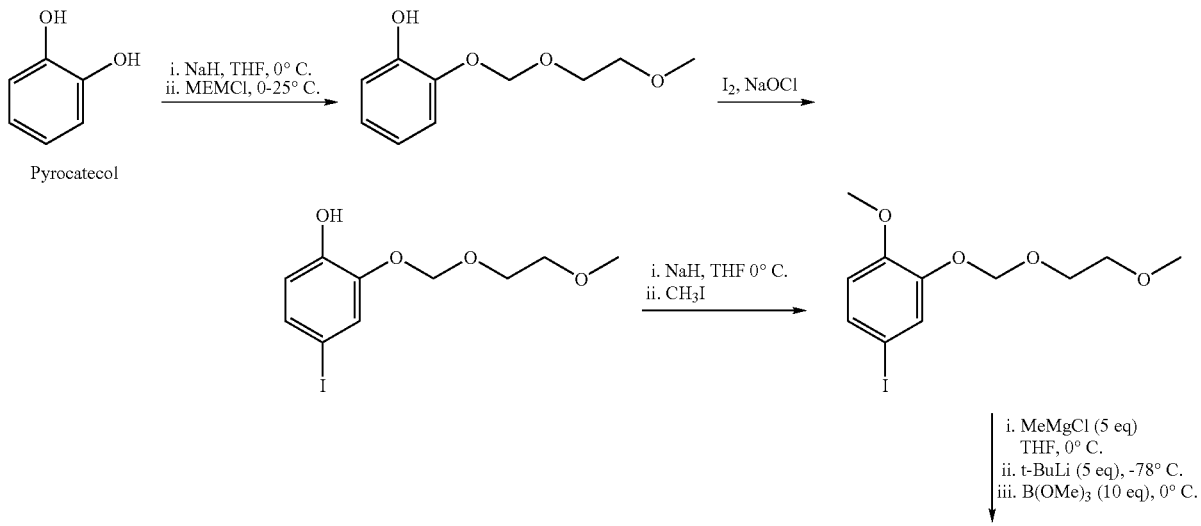

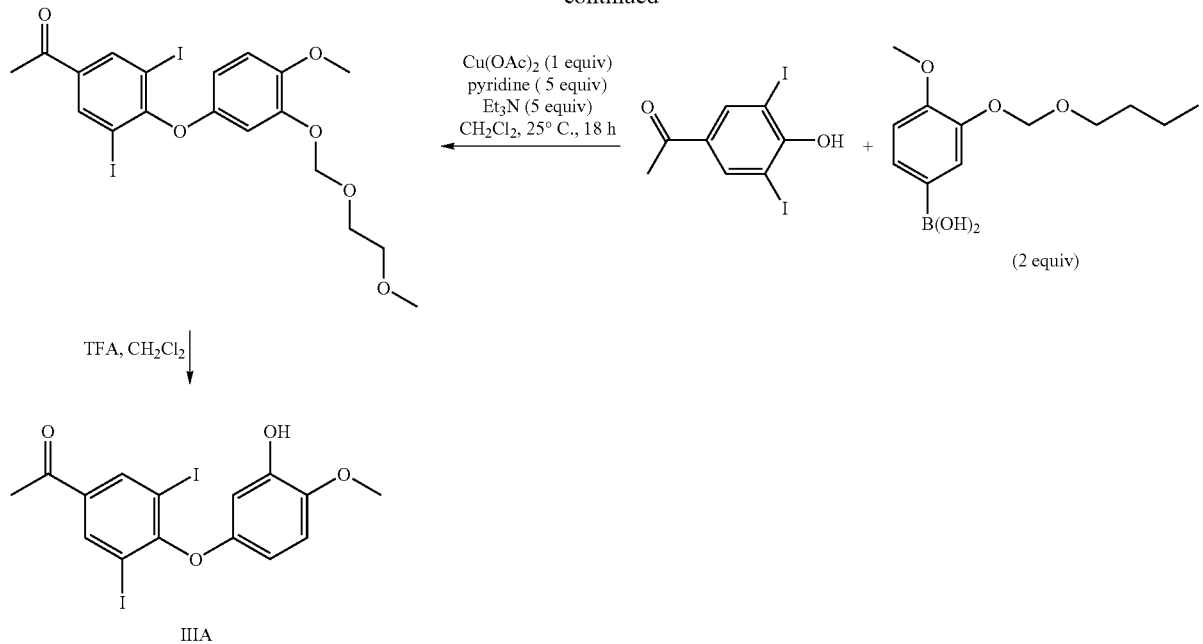

An alternate synthesis of a compound of formula IIIA starts with a compound of formula IIIB, which is first converted to a diazonium salt in the presence of a metal nitrate, such as sodium nitrate. This nitronium ion is then transformed into the hydroxy by reflux in the presence of a strong acid, such as sulfuric acid.

First, the compound of formula IIIB is obtained as described herein and is suspended in 6 N sulfuric cid. The reaction mixture is cooled to Ti=0-5° C. Sodium nitrate is dissolved in water and is added dropwise under the surface of the starting material suspension. As the suspension is very thick, further water is added and stirring is continued for 2.5 hour at Ti=0-5° C. Further sodium nitrate is added and stirring is continued for 3 hours. A few crystals of urea are added to decompose any excess sodium nitrate. Test with iodine-starch paper.

The diazonium suspension is added to pre-heated 6N sulfuric acid within 1 hour. Heating is continued for 24 hours. The suspension is cooled to room temperature and filtered off and washed with water. The solid is dried in vacuo at 40° C. The crude product may be purified by chromatography on silica gel.

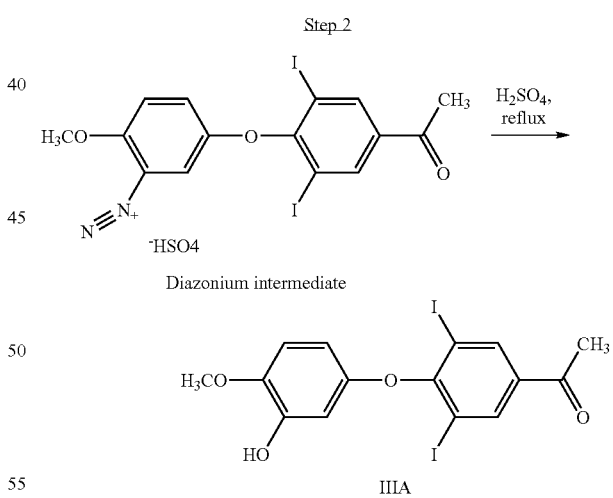

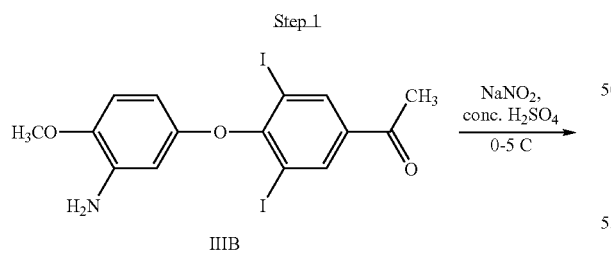

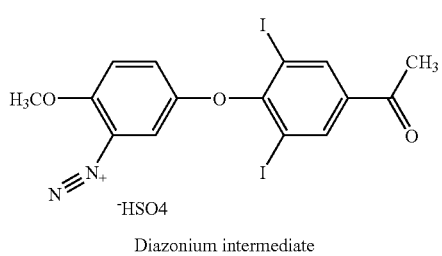

An example of a synthesis scheme for candidate tubulin inhibitor of a compound of formula IIIB from 4-bromoanisole (CAS 104-92-7) is as provided below (Evans D. A. et al., *J. Am. Chem. Soc.* 2001, 123, 12411-12413; Evans D. A. et al., *Tetrahedron Lett.* 1998, 39, 2933-2936; Muathen H. A., *Molecules,* 2003, 8, 593-598; Saimoto H. et al., *Tetrahedron Lett.,* 1986, 27, 1607; Hantson A. L. et al., 5th International Conference on Isotopes, Brussels, Belgium, Apr. 25-29, 2005, 279-283; Covello M. et. al., *Chem. Abstr.* 1962, 56, 5929i).

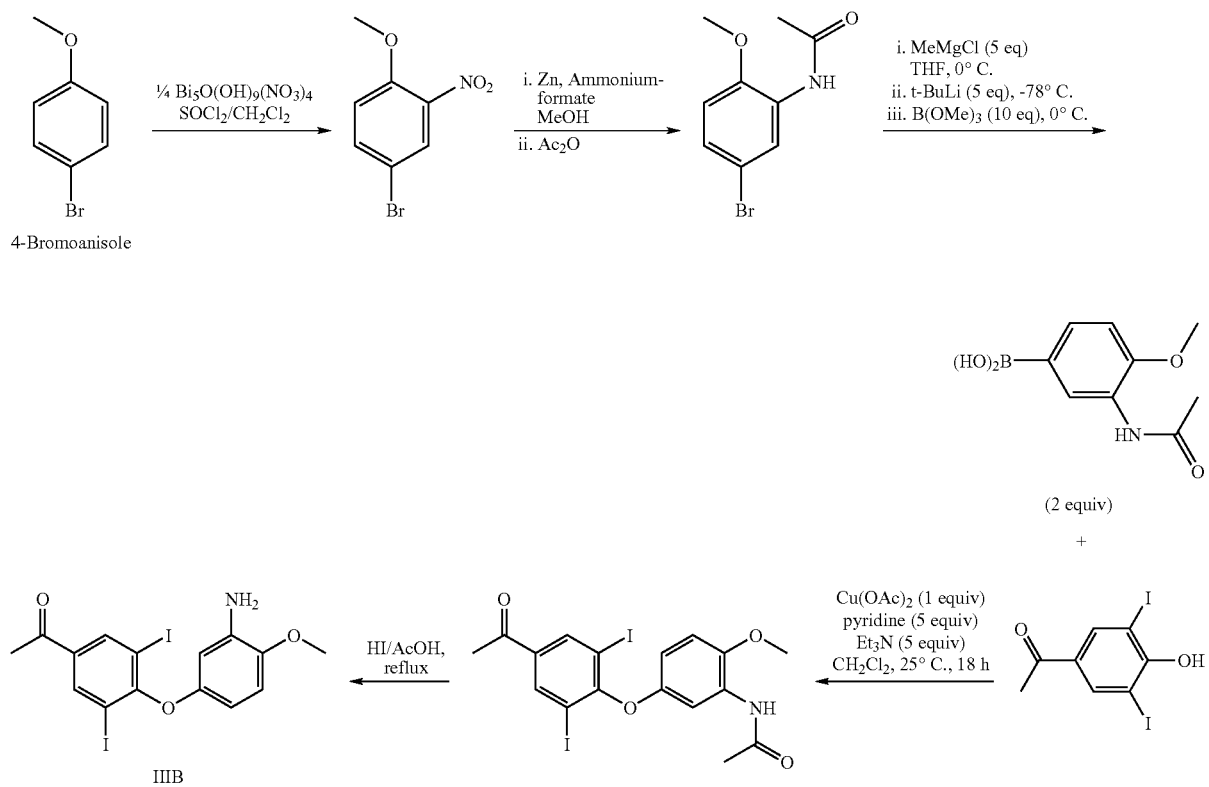

An alternate synthetic scheme for a compound of formula IIIB is begins with 1-(3,5-diiodo-4-(4-methoxyphenoxy)phenyl)ethanone (DIPE) as starting material. First, DIPE is nitrated to form a 3-nitro adduct. The nitration may be carried out in a suitable reagent, such as nitric acid, e.g. in the presence of a strong acid such as sulfuric acid. Once the 3-nitro adduct (nitro intermediate) has been formed, it can then be reduced to form the 3-amino adduct, which is the compound of formula IIIB.

The reduction of the nitro intermediate must be carried out with a reducing reagent that will selectively reduce the aryl nitro moiety but not the aryl carbonyl moiety. It has been found that tin(II)chloride ($SnCl_2$) in 37% HCl is such a reagent; however other reagent systems that reduce the nitro moiety and spare the aryl carbonyl moiety may be employed. In some embodiments it may be critical to choose a reagent such as $SnCl_2$/HCl that gives a nearly quantitative (>95% or >97.5%, >99% purity) conversion of 3-nitro to 3-amino moiety.

In step 1, DIPE is first dissolved in methylene chloride. A solution of nitric acid and sulfuric acid is cooled to Ti–0–5° C. The acid mixture is added to the starting material solution at Ti<5° C. A solution of the nitro-intermediate is obtained. The reaction mixture is then diluted with methylene chloride until solids dissolve completely. The organic phase is washed with water, 10% aqueous sodium bicarbonate solution and then water. The organic phase is dried over sodium sulfate and concentrated in vacuo.

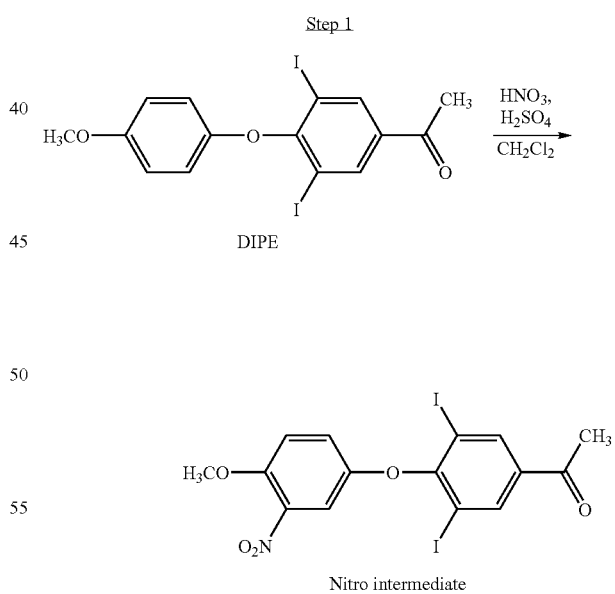

In step 2, a solution of ethanol and 37% HCl is cooled to Ti<10° C., to which is added anhydrous tin(II)chloride. This produces a clear, colorless solution. The nitro intermediate is then added immediately. The ice bath is removed and the suspension is warmed to room temperature within 30 min. The suspension is then warmed to Ti=30-35° C. This reaction mixture is then stirred at room temperature overnight. The reaction mixture is then filtered and the filtrate washed with ethanol and dried in vacuo at 38° C. The crude product may then be re-crystallized from TBME.

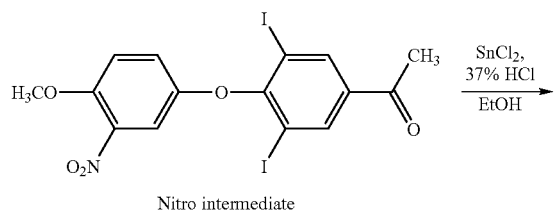

Nitro intermediate

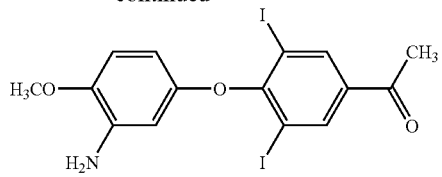

IIIB

An example of a synthesis scheme for candidate tubulin inhibitor of a compound of formula IIIC from 1-iodo-4-methoxy-2-nitrobenzene (CAS 50590-07-3) is as provided below (Beringer et al. *JACS*, 1959, 81, 343; *Organic Syntheses*, 1995, Coll. Vol. 3, p. 355; 1942, Vol. 22, p. 52; Hantson A. L. et al., 5$^{th}$ International Conference on Isotopes, Brussels, Belgium, Apr. 25-29, 2005, 279-283; Gowda D. et al., *Ind. J. Chem. Sect. B,* 2001, 40, 75-77; Covello M. et. al., *Chem. Abstr.* 1962, 56, 5929i).

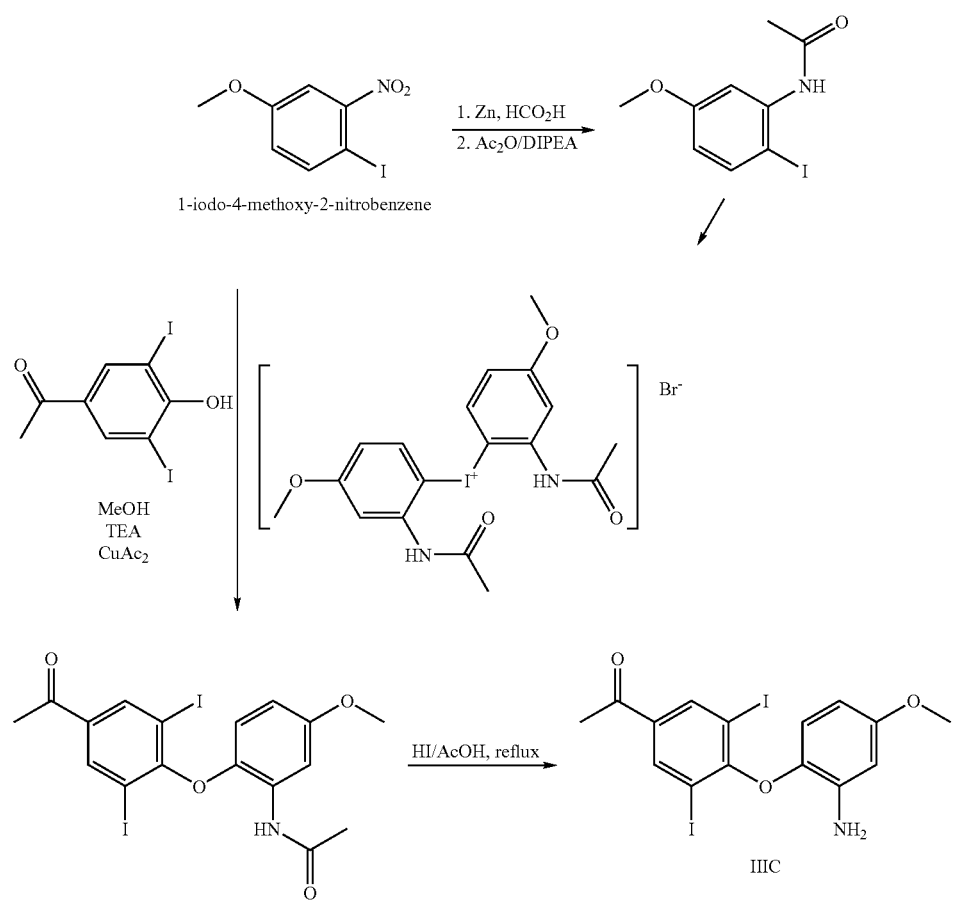

An example of a synthesis scheme for candidate tubulin inhibitor of a compound of formula IIID from pyrocatechol (CAS 120-80-9) is as provided below (Evans D. A. et al., *J. Am. Chem. Soc.* 2001, 123, 12411-12413; Evans D. A. et al., *Tetrahedron Lett.* 1998, 39, 2933-2936; Perich J. W et al., *Synthesis* 1988, 142-144; Covello M. et. al., *Chem. Abstr.* 1962, 56, 5929i).

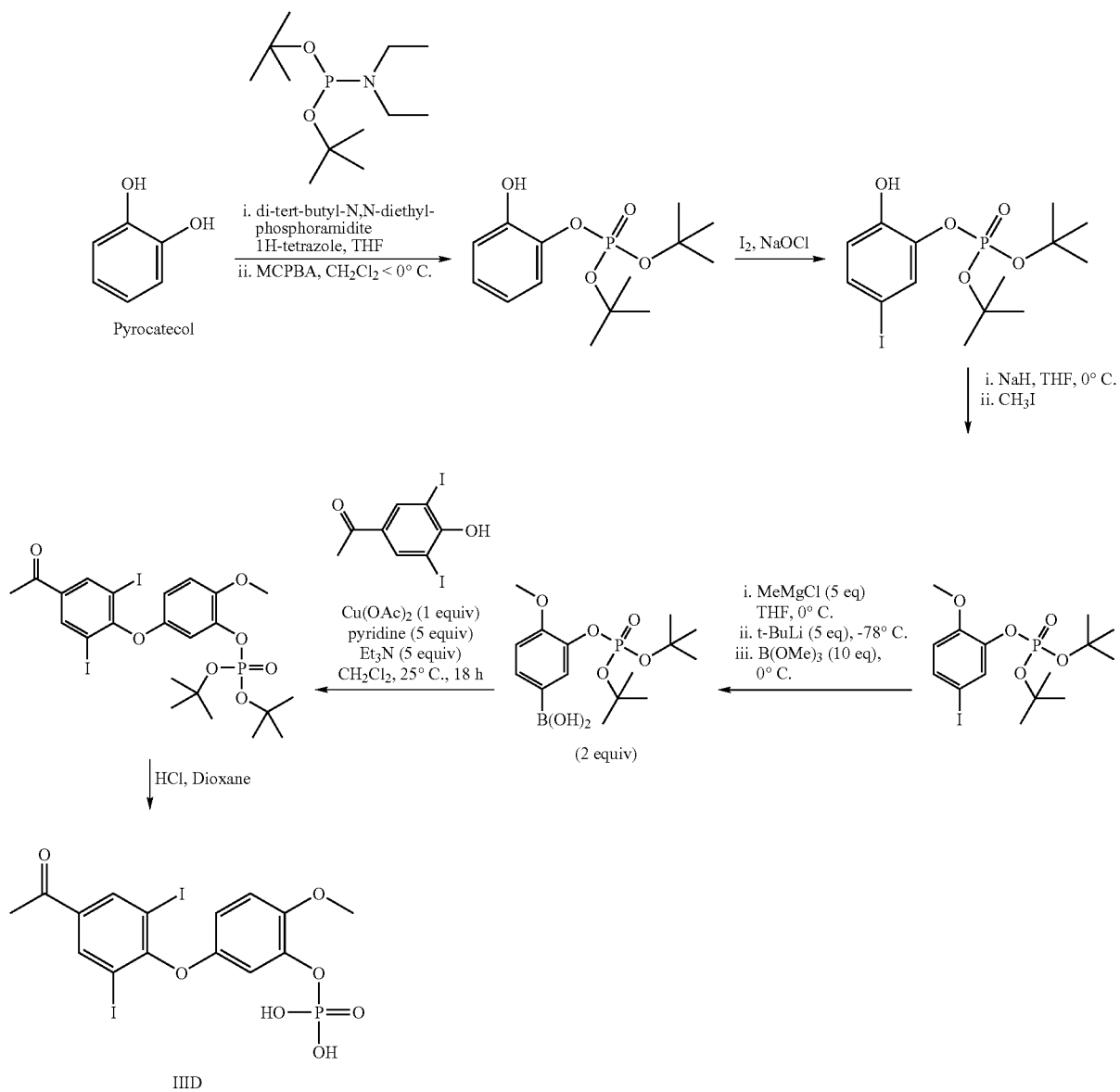

An example of a synthesis scheme for candidate tubulin inhibitor of a compound of formula IIIE from 3-(3-methoxyphenyl)proprionic acid (CAS 10516-71-9) is as provided below (Beringer et al., *JACS*, 1959, 81, 343; *Organic Syntheses*, 1995, Coll. Vol. 3, p. 355; 1942, Vol. 22, p. 52; Wing-Wah Sy, *Tetrahedron Lett.* 1993, 39, 6223-6224; Hantson A. L. et al., 5th International Conference on Isotopes, Brussels, Belgium, Apr. 25-29, 2005, 279-283; Covello M. et. al., *Chem. Abstr.* 1962, 56, 5929i; B. W. Yoo et. al., *Bull. Korean Chem. Soc.* 2004, Vol. 25, No. 11, 1633-1634).

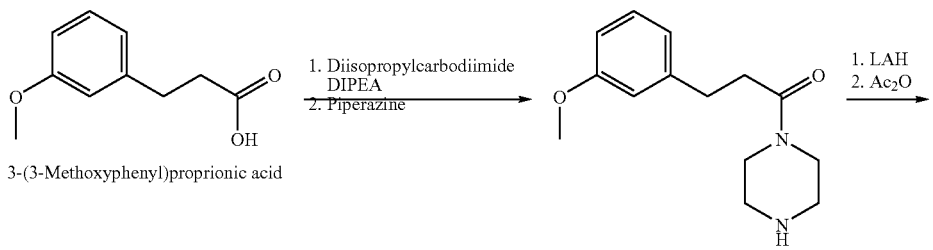

-continued

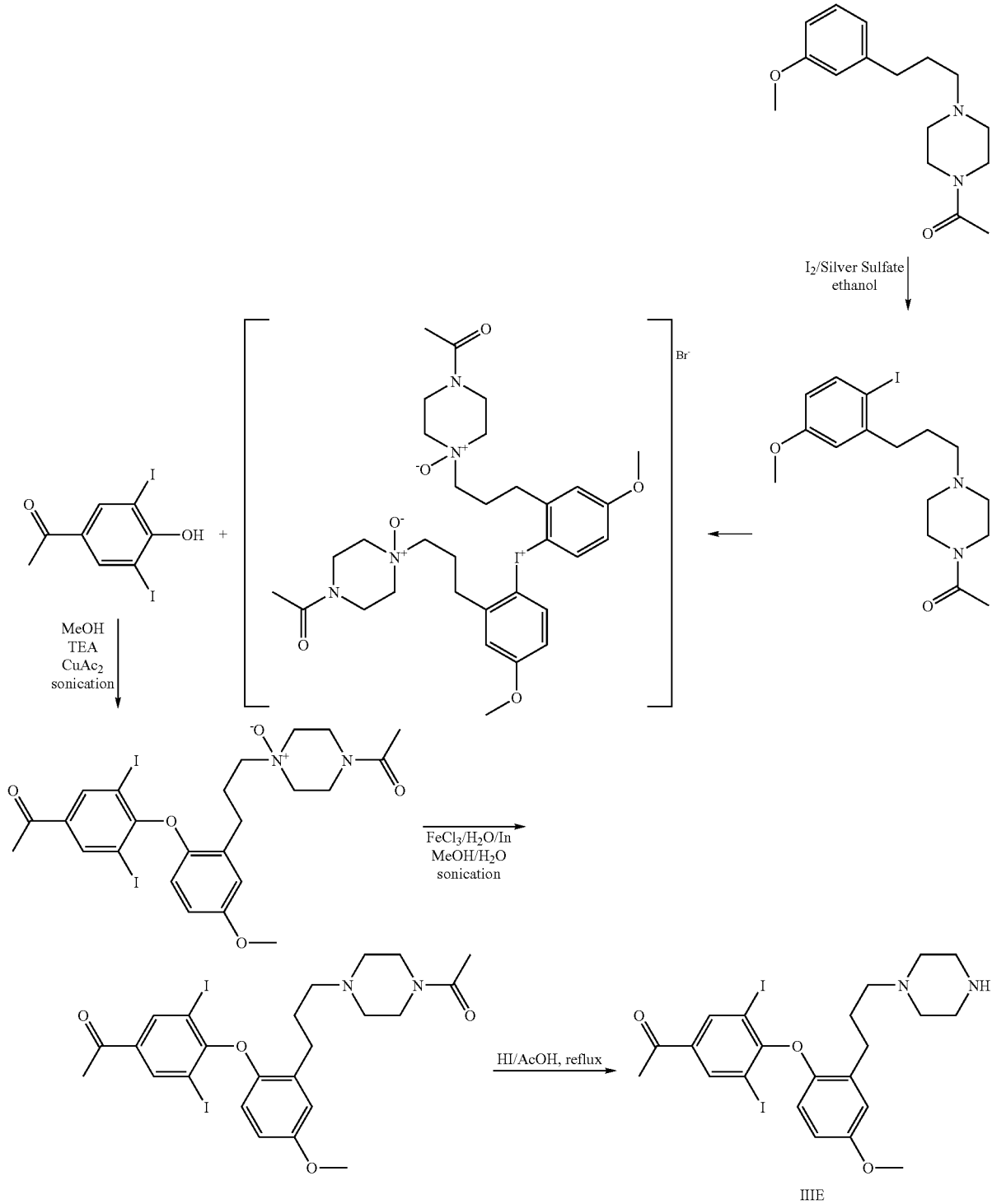

IIIE

Techniques for the Measurement of Tubulin Inhibiting Activity of Tubulin Inhibitors In some embodiments, a tubulin inhibiting activity of the candidate tubulin inhibitor is evaluated to characterize the ability of a candidate tubulin inhibitor to bind to a tubulin protein or tubulin heterodimer, and/or characterize the ability of the candidate tubulin inhibitor to modify the activity of a tubulin protein or tubulin heterodimer. Preferably, the technique used for evaluation is an assay technique. Both in vitro and in vivo assays can be used in accordance with the methods of the invention depending on the identity of the tubulin protein or tubulin heterodimer being investigated. Appropriate activity or functional assays can be readily determined by the skilled artisan based on the disclosure herein. The candidate tubulin inhibitors described herein can be used in assays, including radiolabeled, antibody detection and fluorometric assays, for the isolation, identification, or structural or functional characterization of the tubulin protein or tubulin heterodimer.

The assay can be an enzyme inhibition assay or tubulin inhibition assay utilizing a full length or truncated tubulin protein or tubulin heterodimer. The tubulin protein or tubulin heterodimer can be contacted with the candidate tubulin inhibitor and a measurement of the binding affinity of the candidate tubulin inhibitor against a standard is determined. Such assays are known to one of ordinary skill in the art and are within the scope of the present invention. The assay for evaluating tubulin inhibiting activity of the candidate tubulin inhibitor can be a cell-based assay. The candidate tubulin inhibitor is contacted with a cell and a measurement of an inhibition of a standard marker produced in the cell is determined. Cells can be either isolated from an animal, including a transformed cultured cell, or can be in a living animal. Such assays are also known to one of ordinary skill in the art and are within the scope of the present invention.

The candidate tubulin inhibitors of the present invention can be identified using, for example, immunoassays such as enzyme linked immunoabsorbent assays (ELISA) and radioimmunoassays (RIA) or binding assays such as Biacore assays. Binding assays can employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Without limiting the scope of the present invention, some of the examples of the techniques for measurement of the bioactivity of the tubulin inhibitors, are provided below.

Fluorescence Microscopy

Some embodiments of the invention include fluorescence microscopy for measuring the tubulin inhibiting activity of the candidate tubulin inhibitors of the present invention. Fluorescence microscopy enables the molecular composition of the structures being observed to be identified through the use of fluorescently-labeled probes of high chemical specificity such as antibodies. It can be done by directly conjugating a fluorophore to a tubulin protein or tubulin heterodimer and introducing this back into a cell. Fluorescent analogue can behave like the native protein and can therefore serve to reveal the distribution and behavior of this tubulin protein or tubulin heterodimer in the cell. Along with NMR, infrared spectroscopy, circular dichroism and other techniques, protein intrinsic fluorescence decay and its associated observation of fluorescence anisotropy, collisional quenching and resonance energy transfer are techniques for tubulin detection. The naturally fluorescent proteins can be used as fluorescent probes. The jellyfish *Aequorea victoria* produces a naturally fluorescent protein known as green fluorescent protein (GFP). The fusion of these fluorescent probes to a target protein enables visualization by fluorescence microscopy and quantification by flow cytometry.

By way of example only, some of the probes are labels such as, fluorescein and its derivatives, carboxyfluoresceins, rhodamines and their derivatives, atto labels, fluorescent red and fluorescent orange: cy3/cy5 alternatives, lanthanide complexes with long lifetimes, long wavelength labels—up to 800 nm, DY cyanine labels, and phycobili proteins. By way of example only, some of the probes are conjugates such as, isothiocyanate conjugates, streptavidin conjugates, and biotin conjugates. By way of example only, some of the probes are enzyme substrates such as, fluorogenic and chromogenic substrates. By way of example only, some of the probes are fluorochromes such as, FITC (green fluorescence, excitation/emission=506/529 nm), rhodamine B (orange fluorescence, excitation/emission=560/584 nm), and Nile blue A (red fluorescence, excitation/emission=636/686 nm). Fluorescent nanoparticles can be used for various types of immunoassays. Fluorescent nanoparticles are based on different materials, such as, polyacrylonitrile, and polystyrene etc. Fluorescent molecular rotors are sensors of microenvironmental restriction that become fluorescent when their rotation is constrained. Few examples of molecular constraint include increased dye (aggregation), binding to antibodies, or being trapped in the polymerization of actin. IEF (isoelectric focusing) is an analytical tool for the separation of ampholytes, mainly proteins. An advantage for IEF-gel electrophoresis with fluorescent IEF-marker is the possibility to directly observe the formation of gradient. Fluorescent IEF-marker can also be detected by UV-absorption at 280 nm (20° C.).

A peptide library can be synthesized on solid supports and, by using coloring receptors, subsequent dyed solid supports can be selected one by one. If receptors cannot indicate any color, their binding antibodies can be dyed. The method can not only be used on protein receptors, but also on screening binding ligands of synthesized artificial receptors and screening new metal binding ligands as well. Automated methods for HTS and FACS (fluorescence activated cell sorter) can also be used.

Immunoassays

Some embodiments of the invention include immunoassay for measuring the tubulin inhibiting activity of the candidate tubulin inhibitors of the present invention. In immunoblotting like the western blot of electrophoretically-separated proteins a single protein can be identified by its antibody. An immunoassay can be a competitive binding immunoassay where analyte competes with a labeled antigen for a limited pool of antibody molecules (e.g. radioimmunoassay, EMIT). An immunoassay can be non-competitive where an antibody is present in excess and is labeled. As analyte antigen complex is increased, the amount of labeled antibody-antigen complex can also increase (e.g. ELISA). Antibodies can be polyclonal if produced by antigen injection into an experimental animal, or monoclonal if produced by cell fusion and cell culture techniques. In an immunoassay, the antibody can serve as a specific reagent for the analyte antigen.

Without limiting the scope and content of the present invention, some of the types of immunoassays are, but not limited to, RIAs (radioimmunoassay), enzyme immunoassays like ELISA (enzyme-linked immunosorbent assay), EMIT (enzyme multiplied immunoassay technique), microparticle enzyme immunoassay (MEIA), LIA (luminescent immunoassay), and FIA (fluorescent immunoassay). The antibodies—either used as primary or secondary ones—can be labeled with radioisotopes (e.g. 125I), fluorescent dyes (e.g. FITC) or enzymes (e.g. HRP or AP) which can catalyze fluorogenic or luminogenic reactions.

Biotin, or vitamin H is a co-enzyme which inherits a specific affinity towards avidin and streptavidin. This interaction makes biotinylated peptides a useful tool in various biotechnology assays for quality and quantity testing. To improve biotin/streptavidin recognition by minimizing steric hindrances, it can be necessary to enlarge the distance between biotin and the peptide itself. This can be achieved by coupling a spacer molecule (e.g., 6-aminohexanoic acid) between biotin and the peptide.

The biotin quantitation assay for biotinylated proteins provides a sensitive fluorometric assay for accurately determining the number of biotin labels on a protein. Biotinylated peptides are widely used in a variety of biomedical screening systems requiring immobilization of at least one of the interaction partners onto streptavidin coated beads, membranes, glass slides or microtiter plates. The assay is based on the displacement of a ligand tagged with a quencher dye from the biotin binding sites of a reagent. To expose any biotin groups in a multiply-labeled protein that are sterically restricted and inaccessible to the reagent, the protein can be treated with protease for digesting the protein.

EMIT is a competitive binding immunoassay that avoids the usual separation step. A type of immunoassay in which the protein is labeled with an enzyme, and the enzyme-protein-antibody complex is enzymatically inactive, allowing quantitation of unlabelled protein. Some embodiments of the invention include ELISA to analyze tubulin proteins or tubulin heterodimers. ELISA is based on selective antibodies attached to solid supports combined with enzyme reactions to produce systems capable of detecting low levels of proteins. It is also known as enzyme immunoassay or EIA. The protein is detected by antibodies that have been made against it, that is, for which it is the antigen. Monoclonal antibodies are often used.

The test can require the antibodies to be fixed to a solid surface, such as the inner surface of a test tube, and a preparation of the same antibodies coupled to an enzyme. The enzyme can be one (e.g., β-galactosidase) that produces a colored product from a colorless substrate. The test, for example, can be performed by filling the tube with the antigen solution (e.g., protein) to be assayed. Any antigen molecule present can bind to the immobilized antibody molecules. The antibody-enzyme conjugate can be added to the reaction mixture. The antibody part of the conjugate binds to any antigen molecules that were bound previously, creating an antibody-antigen-antibody "sandwich". After washing away any unbound conjugate, the substrate solution can be added. After a set interval, the reaction is stopped (e.g., by adding 1 N NaOH) and the concentration of colored product formed is measured in a spectrophotometer. The intensity of color is proportional to the concentration of bound antigen.

ELISA can also be adapted to measure the concentration of antibodies, in which case, the wells are coated with the appropriate antigen. The solution (e.g., serum) containing antibody can be added. After it has had time to bind to the immobilized antigen, an enzyme-conjugated anti-immunoglobulin can be added, consisting of an antibody specific for the antibodies being tested for. After washing away unreacted reagent, the substrate can be added. The intensity of the color produced is proportional to the amount of enzyme-labeled antibodies bound (and thus to the concentration of the antibodies being assayed).

Some embodiments of the invention include radioimmunoassays for measuring the tubulin inhibiting activity of the candidate tubulin inhibitors of the present invention. Radioactive isotopes can be used to study in vivo metabolism, distribution, and binding of small amount of compounds. Radioactive isotopes of $^1H$, $^{12}C$, $^{31}P$, $^{32}S$, and $^{127}I$ in body are used such as $^3H$, $^{14}C$, $^{32}P$, $^{35}S$, and $^{125}I$. In receptor fixation method in 96 well plates, receptors can be fixed in each well by using antibody or chemical methods and radioactive labeled ligands can be added to each well to induce binding. Unbound ligands can be washed out and then the standard can be determined by quantitative analysis of radioactivity of bound ligands or that of washed-out ligands. Then, addition of screening target compounds can induce competitive binding reaction with receptors. If the compounds show higher affinity to receptors than standard radioactive ligands, most of radioactive ligands would not bind to receptors and can be left in solution. Therefore, by analyzing quantity of bound radioactive ligands (or washed-out ligands), testing compounds' affinity to receptors can be indicated.

The filter membrane method can be needed when receptors cannot be fixed to 96 well plates or when ligand binding needs to be done in solution phase. In other words, after ligand-receptor binding reaction in solution, if the reaction solution is filtered through nitrocellulose filter paper, small molecules including ligands can go through it and only protein receptors can be left on the paper. Only ligands that strongly bound to receptors can stay on the filter paper and the relative affinity of added compounds can be identified by quantitative analysis of the standard radioactive ligands.

Some embodiments of the invention include fluorescence immunoassays for measuring the tubulin inhibiting activity of the candidate tubulin inhibitors of the present invention. Fluorescence based immunological methods are based upon the competitive binding of labeled ligands versus unlabeled ones on highly specific receptor sites. The fluorescence technique can be used for immunoassays based on changes in fluorescence lifetime with changing analyte concentration. This technique can work with short lifetime dyes like fluorescein isothiocyanate (FITC) (the donor) whose fluorescence can be quenched by energy transfer to eosin (the acceptor). A number of photoluminescent compounds can be used, such as cyanines, oxazines, thiazines, porphyrins, phthalocyanines, fluorescent infrared-emitting polynuclear aromatic hydrocarbons, phycobiliproteins, squaraines and organo-metallic complexes, hydrocarbons and azo dyes.

Fluorescence-based immunological methods can be, for example, heterogeneous or homogenous. Heterogeneous immunoassays comprise physical separation of bound from free labeled analyte. The analyte or antibody can be attached to a solid surface. Homogenous immunoassays comprise no physical separation. Double-antibody fluorophore-labeled antigen participates in an equilibrium reaction with antibodies directed against both the antigen and the fluorophore. Labeled and unlabeled antigen can compete for a limited number of anti-antigen antibodies.

Some of the fluorescence immunoassay methods include simple fluorescence labeling method, fluorescence resonance energy transfer (FRET), time resolved fluorescence (TRF), and scanning probe microscopy (SPM). The simple fluorescence labeling method can be used for receptor-ligand binding, enzymatic activity by using pertinent fluorescence, and as a fluorescent indicator of various in vivo physiological changes such as pH, ion concentration, and electric pressure.

Method of Treatment with Tubulin Inhibitors

The present invention relates to a pharmaceutical composition, medicament, drug, or other composition of the candidate tubulin inhibitors comprising compounds of formulae I-III where III includes IIIA-E, for treatment of diseases. Preferably, the diseases are tubulin-mediated diseases. The candidate tubulin inhibitors of the present invention can have therapeutic benefit in the treatment of various diseases including cancer and metabolic diseases, and as an adjunct therapy with chemotherapeutic agents/radiation in therapy for cancer.

The methods of the present invention also comprise administering one or more the candidate tubulin inhibitors in combination with other therapies. The condition being treated will determine the type of therapy that will be co-administered with the candidate tubulin inhibitors. For example, for treating cancer, the compound of some embodiments of the invention can be used in combination with antibody (polyclonal or monoclonal) therapy, chemotherapy, radiation therapy, bone marrow transplantation, side-effect-limiting therapy, nucleotide therapy, gene therapy, or a combination thereof.

In addition, the candidate tubulin inhibitors can be used to treat a variety of diseases including metabolic diseases. Such diseases, include, but are not limited to, gout.

In another aspect of the invention, the candidate tubulin inhibitors can be utilized to treat cancer, and to radiosensitize and/or chemosensitize cancer cells. The candidate tubulin inhibitors of the present invention can be "anticancer agents," which term also encompasses "anti-tumor cell growth agents," "pro-differentiating reagents," "anti-angiogenic agents," "pro-angiogenic agents," "anti-mitotic agents," "anti-proliferative agents," "pro-apoptotic agents," "anti-vascular agents," and "pro-necrotic agents." Radiosensitizers are known to increase the sensitivity of cancerous cells to the toxic effects of electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BrDU), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, photofrin, benzoporphyrin derivatives, NPe6, tin etioporphyrin SnET2, pheoborbide-α, bacteriochlorophyll-α, naphthalocyanines, phthalocyanines, zinc phthalocyanine, and therapeutically effective analogs and derivatives of the same.

Chemosensitizers are also known to increase the sensitivity of cancerous cells to the toxic effects of chemotherapeutic compounds. Exemplary chemotherapeutic agents that can be used in conjunction with candidate tubulin inhibitors include, but are not limited to, adriamycin, camptothecin, dacarbazine, carboplatin, cisplatin, daunorubicin, docetaxel, doxorubicin, interferon (alpha, beta, gamma), interleukin 2, innotecan, paclitaxel, streptozotocin, temozolomide, topotecan, and therapeutically effective analogs and derivatives of the same. In addition, other therapeutic agents which can be used in conjunction with candidate tubulin inhibitors include, but are not limited to, 5-fluorouracil, leucovorin, 5'-amino-5'-deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and L-BSO.

The methods of treatment as disclosed herein can be via oral administration, transmucosal administration, buccal administration, nasal administration, inhalation, parental administration, intravenous, subcutaneous, intramuscular, sublingual, transdermal administration, and rectal administration.

Pharmaceutical compositions of the candidate tubulin inhibitors of the present invention, include compositions wherein the active ingredient is contained in a therapeutically or prophylactically effective amount, i.e., in an amount effective to achieve therapeutic or prophylactic benefit. The actual amount effective for a particular application will depend, inter alia, on the condition being treated and the route of administration. Determination of an effective amount is well within the capabilities of those skilled in the art. The pharmaceutical compositions comprise the candidate tubulin inhibitor, one or more pharmaceutically acceptable carriers, diluents or excipients, and optionally additional therapeutic agents. The compositions can be formulated for sustained or delayed release.

A preferred therapeutic composition of the present invention also includes an excipient, an adjuvant and/or carrier. Suitable excipients include compounds that the subject to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration. In one embodiment of the present invention, a therapeutic composition can include a carrier. Carriers include compounds that increase the half-life of a therapeutic composition in the treated subject. Suitable carriers include, but are not limited to, polymeric controlled release vehicles, biodegradable implants, liposomes, bacteria, viruses, other cells, oils, esters, and glycols.

The oral form in which the therapeutic agent is administered can include powder, tablet, capsule, solution, or emulsion. The effective amount can be administered in a single dose or in a series of doses separated by appropriate time intervals, such as hours. Pharmaceutical compositions can be formulated in conventional manner using one or more physiologically acceptable carriers comprising excipients and auxiliaries which facilitate processing of the active compounds into preparations which can be used pharmaceutically. Proper formulation is dependent upon the route of administration chosen. Suitable techniques for preparing pharmaceutical compositions of the therapeutic agents of the present invention are well known in the art.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular candidate tubulin inhibitor, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

Some of the examples of diseases treatable by candidate tubulin inhibitors of the present invention are disclosed herein but they are not in any way limiting to the scope of the present invention.

Examples of Various Diseases

Various diseases that can be treated by the candidate tubulin inhibitors of the present invention include, but are not limited to, cancer types including adrenal cortical cancer, anal cancer, aplastic anemia, bile duct cancer, bladder cancer, bone cancer, bone metastasis, adult CNS brain tumors, children CNS brain tumors, breast cancer, castleman disease, cervical cancer, childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, Hodgkin's disease, Kaposi' sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, nonmelanoma skin cancer, stomach cancer, testicular cancer, thymus cancer, thyroid cancer, uterine sarcoma, vaginal cancer, vulvar cancer, Waldenstrom's macroglobulinemia, chronic lymphocyte leukemia, and reactive lymphoid hyperplasia.

The diseases include cancer angiogenesis, new or established vascularization of tumors, and tumor cell proliferation and metastasis. Certain of the compounds described herein are also useful in the promotion of angiogenesis, thus one embodiment of the present invention is to treat diseases requiring growth of new blood vessels. Such diseases include, but are not limited to, myocardial hypertrophy, angina, and high blood pressure. The invention in an embodiment also provides methods to treat other diseases, such as, metabolic diseases like gout.

Examples of Cancer

The cancer include but are not limited to, adrenal cortical cancer, anal cancer, aplastic anemia, bile duct cancer, bladder cancer, bone cancer, bone metastasis, Adult CNS brain tumors, Children CNS brain tumors, breast cancer, blood cancer, Castleman Disease, cervical cancer, Childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, Hodgkin's disease, Kaposi'sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, nonmelanoma skin cancer, stomach cancer, testicular cancer, thymus cancer, thyroid cancer, uterine sarcoma, vaginal cancer, vulvar cancer, and Waldenstrom's macroglobulinemia.

Carcinoma of the thyroid gland is the most common malignancy of the endocrine system. Carcinoma of the thyroid gland include differentiated tumors (papillary or follicular) and poorly differentiated tumors (medullary or anaplastic). Carcinomas of the vagina include squamous cell carcinoma, adenocarcinoma, melanoma and sarcoma. Testicular cancer is broadly divided into seminoma and nonseminoma types.

Thymomas are epithelial tumors of the thymus, which may or may not be extensively infiltrated by non-neoplastic lymphocytes. The term thymoma is customarily used to describe neoplasms that show no overt atypia of the epithelial component. A thymic epithelial tumor that exhibits clear-cut cytologic atypia and histologic features no longer specific to the thymus is known as a thymic carcinoma (also known as type C thymoma).

The methods provided by the invention can comprise the administration of the tubulin inhibitor s in combination with other therapies. The choice of therapy that can be co-administered with the compositions of the invention can depend, in part, on the condition being treated. For example, for treating acute myeloid leukemia, a tubulin inhibitor can be used in combination with radiation therapy, monoclonal antibody therapy, chemotherapy, bone marrow transplantation, gene therapy, immunotherapy, or a combination thereof.

Her-2 Related Cancer

Her-2 disease is a type of breast cancer. Characterized by aggressive growth and a poor prognosis, it can be caused by the presence of excessive numbers of a gene called HER2 (human epidermal growth factor receptor-2) in tumor cells. Therapies that can used in combination with the tubulin inhibitor s as disclosed herein include, but are no limited to Her-2 antibodies such as herceptin, anti-hormones (e.g., selective oestrogen receptor modulator (SERM) tamoxifen), chemotherapy and radiotherapy, aromatase inhibitors (e.g. anastrazole, letrozole and exemestane) and anti-oestrogens (e.g., fulvestrant (Faslodex)).

Blood Cancer

Lymphoma

B-Cell Lymphomas

Non-Hodgkin's Lymphomas caused by malignant (cancerous) B-Cell lymphocytes represent a large subset (about 85% in the US) of the known types of lymphoma (the other 2 subsets being T-Cell lymphomas and lymphomas where the cell type is the Natural Killer Cell or unknown). Cells undergo many changes in their life cycle dependent on complex signaling processes between cells and interaction with foreign substances in the body. Apparently various types of lymphoma or leukemia can occur in the B-Cell life cycle.

Breast Cancer

A lobular carcinoma in situ and a ductal carcinoma in situ are breast cancers that develop in the lobules and ducts, respectively, but may not have spread to the fatty tissue surrounding the breast or to other areas of the body. An infiltrating (or invasive) lobular and a ductal carcinoma are cancers that have developed in the lobules and ducts, respectively, and have spread to either the breast's fatty tissue and/or other parts of the body. Other cancers of the breast that can benefit from treatment provided by the methods of the present invention are medullary carcinomas, colloid carcinomas, tubular carcinomas, and inflammatory breast cancer.

In some embodiments, the invention provides for treatment of so-called "triple negative" breast cancer. There are several subclasses of breast cancer identified by classic biomarkers such as estrogen receptor (ER) and/or progesterone receptor (PR) positive tumors, HER2-amplified tumors, and ER/PR/HER2-negative tumors. These three subtypes have been reproducibly identified by gene expression profiling in multiple breast cancer and exhibit basal-like subtype expression profiles and poor prognosis. Triple negative breast cancer is characterized by ER/PR/HER2-negative tumors.

Ovarian Cancer

The ovarian cancer includes but is not limited to, epithelial ovarian tumors, adenocarcinoma in the ovary and an adenocarcinoma that has migrated from the ovary into the abdominal cavity. Treatments for ovarian cancer that can be used in combination with the tubulin inhibitors of the present invention include but are not limited to, surgery, immunotherapy, chemotherapy, hormone therapy, radiation therapy, or a combination thereof. Some possible surgical procedures include debulking, and a unilateral or bilateral oophorectomy and/or a unilateral or bilateral salpigectomy.

Anti-cancer drugs that can be used in the combination therapy include cyclophosphamide, etoposide, altretamine, and ifosfamide. Hormone therapy with the drug tamoxifen can be used to shrink ovarian tumors. Radiation therapy can be external beam radiation therapy and/or brachytherapy.

Cervical Cancer

The cervical cancer includes, but is not limited to, an adenocarcinoma in the cervix epithelial. Two main types of this cancer exist: squamous cell carcinoma and adenocarcinomas. Some cervical cancers have characteristics of both of these and are called adenosquamous carcinomas or mixed carcinomas.

Prostate Cancer

The prostate cancer includes, but is not limited to, an adenocarcinoma or an adenocarcinoma that has migrated to the bone. Prostate cancer develops in the prostate organ in men, which surrounds the first part of the urethra.

Pancreatic Cancer

The pancreatic cancer includes, but is not limited to, an epitheloid carcinoma in the pancreatic duct tissue and an adenocarcinoma in a pancreatic duct. Treatments that can be used in combination with the tubulin inhibitor s of the present invention include but are not limited to, surgery, immunotherapy, radiation therapy, and chemotherapy. Possible surgical treatment options include a distal or total pancreatectomy and a pancreaticoduodenectomy (Whipple procedure). Radiation therapy can be an option for pancreatic cancer patients, such as external beam radiation where radiation is focused on the tumor by a machine outside the body. Another option is intraoperative electron beam radiation administered during an operation.

Bladder Cancer

The bladder cancer includes, but is not limited to, a transitional cell carcinoma in urinary bladder. Bladder cancers are urothelial carcinomas (transitional cell carcinomas) or tumors in the urothelial cells that line the bladder. The remaining cases of bladder cancer are squamous cell carcinomas, adenocarcinomas, and small cell cancers. Several subtypes of urothelial carcinomas exist depending on whether they are noninvasive or invasive and whether they are papillary, or flat. Noninvasive tumors are in the urothelium, the innermost layer of the bladder, while invasive tumors have spread from the urothelium to deeper layers of the bladder's main muscle wall. Invasive papillary urothelial carcinomas are slender finger-like projections that branch into the hollow center of the bladder and also grow outward into the bladder wall. Non-invasive papillary urothelial tumors grow towards the center of the bladder. While a non-invasive, flat urothelial tumor (also called a flat carcinoma in situ) is confined to the layer of cells closest to the inside hollow part of the bladder, an invasive flat urothelial carcinoma invades the deeper layer of the bladder, particularly the muscle layer.

The therapies that can be used in combination with the tubulin inhibitors of the present invention for the treatment of bladder cancer include surgery, radiation therapy, immunotherapy, chemotherapy, or a combination thereof. Some surgical options are a transurethral resection, a cystectomy, or a radical cystectomy. Radiation therapy for bladder cancer can include external beam radiation and brachytherapy.

Immunotherapy is another method that can be used to treat a bladder cancer patient. One method is *Bacillus* Calmete-Guerin (BCG) where a bacterium sometimes used in tuberculosis vaccination is given directly to the bladder through a catheter. The body mounts an immune response to the bacterium, thereby attacking and killing the cancer cells. Another method of immunotherapy is the administration of interferons, glycoproteins that modulate the immune response. Interferon alpha is often used to treat bladder cancer.

Anti-cancer drugs that can be used in combination to treat bladder cancer include thitepa, methotrexate, vinblastine, doxorubicin, cyclophosphamide, paclitaxel, carboplatin, cisplatin, ifosfamide, gemcitabine, or combinations thereof.

Acute Myeloid Leukemia

The acute myeloid leukemia (AML) includes acute promyleocytic leukemia in peripheral blood. AML begins in the bone marrow but can spread to other parts of the body including the lymph nodes, liver, spleen, central nervous system, and testes. AML can be characterized by immature bone marrow cells usually granulocytes or monocytes, which can continue to reproduce and accumulate.

AML can be treated by other therapies in combination with the tubulin inhibitors of the present invention. Such therapies include but are not limited to, immunotherapy, radiation therapy, chemotherapy, bone marrow or peripheral blood stem cell transplantation, or a combination thereof. Radiation therapy includes external beam radiation and can have side effects. Anti-cancer drugs that can be used in chemotherapy to treat AML include cytarabine, anthracycline, anthracenedione, idarubicin, daunorubicin, idarubicin, mitoxantrone, thioguanine, vincristine, prednisone, etoposide, or a combination thereof.

Monoclonal antibody therapy can be used to treat AML patients. Small molecules or radioactive chemicals can be attached to these antibodies before administration to a patient in order to provide a means of killing leukemia cells in the body. The monoclonal antibody, gemtuzurab ozogamicin, which binds CD33 on AML cells, can be used to treat AML patients unable to tolerate prior chemotherapy regimens. Bone marrow or peripheral blood stem cell transplantation can be used to treat AML patients. Some possible transplantation procedures are an allogenic or an autologous transplant.

Other types of leukemia's that can be treated by the methods provided by the invention include but not limited to, Acute Lymphocytic Leukemia, Chronic Lymphocytic Leukemia, Chronic Myeloid Leukemia, Hairy Cell Leukemia, Myelodysplasia, and Myeloproliferative Disorders.

Lung Cancer

The common type of lung cancer is non-small cell lung cancer (NSCLC), which is divided into squamous cell carcinomas, adenocarcinomas, and large cell undifferentiated carcinomas. Treatment options for lung cancer in combination with the tubulin inhibitors of the present invention include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy can be external beam radiation therapy or brachytherapy.

Some anti-cancer drugs that can be used in chemotherapy to treat lung cancer include cisplatin, carboplatin, paclitaxel, docetaxel, gemcitabine, vinorelbine, irinotecan, etoposde, vinblastine, gefitinib, ifosfamide, methotrexate, or a combination thereof. Photodynamic therapy (PDT) can be used to treat lung cancer patients.

Skin Cancer

There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma, the rarest form of skin cancer, is more likely to invade nearby tissues and spread to other parts of the body.

Different types of treatments that can be used in combination with the tubulin inhibitors of the present invention include but are not limited to, surgery, radiation therapy, chemotherapy and photodynamic therapy. Some possible surgical options for treatment of skin cancer are mohs micrographic surgery, simple excision, electrodesiccation and curettage, cryosurgery, laser surgery. Radiation therapy can be external beam radiation therapy or brachytherapy. Other types of treatments include biologic therapy or immunotherapy, chemoimmunotherapy, topical chemotherapy with fluorouracil and photodynamic therapy.

Eye Cancer, Retinoblastoma

Retinoblastoma is a malignant tumor of the retina. The tumor can be in one eye only or in both eyes. Treatment options that can be used in combination with the tubulin inhibitors of the present invention include enucleation (surgery to remove the eye), radiation therapy, cryotherapy, photocoagulation, immunotherapy, thermotherapy and chemotherapy. Radiation therapy can be external beam radiation therapy or brachytherapy.

Eye Cancer, Intraocular Melanoma

Intraocular melanoma is a disease in which cancer cells are found in the part of the eye called the uvea. The uvea includes the iris, the ciliary body, and the choroid. Intraocular melanoma occurs most often in people who are middle aged. Treatments that can be used in combination with the tubulin inhibitors of the present invention include surgery, immunotherapy, radiation therapy and laser therapy. Surgery is the most common treatment of intraocular melanoma. Some possible surgical options are iridectomy, iridotrabeculectomy, iridocyclectomy, choroidectomy, enucleation and orbital exenteration. Radiation therapy can be external beam radiation therapy or brachytherapy. Laser therapy can be an intensely powerful beam of light to destroy the tumor, thermotherapy or photocoagulation.

Endometrium Cancer

Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

Liver Cancer

Primary liver cancer can occur in both adults and children. Different types of treatments that can be used in combination with the tubulin inhibitors of the present invention include surgery, immunotherapy, radiation therapy, chemotherapy and percutaneous ethanol injection. The types of surgery that can be used are cryosurgery, partial hepatectomy, total hepatectomy and radiofrequency ablation. Radiation therapy can be external beam radiation therapy, brachytherapy, radiosensitizers or radiolabel antibodies. Other types of treatment include hyperthermia therapy and immunotherapy.

Kidney Cancer

Kidney cancer (also called renal cell cancer or renal adenocarcinoma) is a disease in which malignant cells are found in the lining of tubules in the kidney. Treatments that can be used in combination with the tubulin inhibitors of the present invention include surgery, radiation therapy, chemotherapy and immunotherapy. Some possible surgical options to treat kidney cancer are partial nephrectomy, simple nephrectomy and radical nephrectomy. Radiation therapy can be external beam radiation therapy or brachytherapy. Stem cell transplant can be used to treat kidney cancer.

Thyroid Cancer

Thyroid cancer is a disease in which cancer (malignant) cells are found in the tissues of the thyroid gland. The four main types of thyroid cancer are papillary, follicular, medullary and anaplastic. Thyroid cancer can be treated by surgery, immunotherapy, radiation therapy, hormone therapy and chemotherapy. Some possible surgical options that can be used in combination with the tubulin inhibitors of the present invention include but are not limited to, lobectomy, near-total thyroidectomy, total thyroidectomy and lymph node dissection. Radiation therapy can be external radiation therapy or can require intake of a liquid that contains radioactive iodine. Hormone therapy uses hormones to stop cancer cells from growing. In treating thyroid cancer, hormones can be used to stop the body from making other hormones that might make cancer cells grow.

AIDS-Related Lymphoma

AIDS-related lymphoma is a disease in which malignant cells form in the lymph system of patients who have acquired immunodeficiency syndrome (AIDS). AIDS is caused by the human immunodeficiency virus (HIV), which attacks and weakens the body's immune system. The immune system is then unable to fight infection and diseases that invade the body. People with HIV disease have an increased risk of developing infections, lymphoma, and other types of cancer. Lymphomas are cancers that affect the white blood cells of the lymph system. Lymphomas are divided into two general types: Hodgkin's lymphoma and non-Hodgkin's lymphoma. Both Hodgkin's lymphoma and non-Hodgkin's lymphoma can occur in AIDS patients, but non-Hodgkin's lymphoma is more common. When a person with AIDS has non-Hodgkin's lymphoma, it is called an AIDS-related lymphoma. Non-Hodgkin's lymphomas can be indolent (slow-growing) or aggressive (fast-growing). AIDS-related lymphoma is usually aggressive. The three main types of AIDS-related lymphoma are diffuse large B-cell lymphoma, B-cell immunoblastic lymphoma and small non-cleaved cell lymphoma.

Highly-active antiretroviral therapy (HAART) is used to slow progression of HIV. Medicine to prevent and treat infections, which can be serious, is also used. AIDS-related lymphomas can be treated by chemotherapy, immunotherapy, radiation therapy and high-dose chemotherapy with stem cell transplant. Radiation therapy can be external beam radiation therapy or brachytherapy. AIDS-related lymphomas can be treated by monoclonal antibody therapy.

Kaposi's Sarcoma

Kaposi's sarcoma is a disease in which cancer cells are found in the tissues under the skin or mucous membranes that line the mouth, nose, and anus. Kaposi's sarcoma can occur in people who are taking immunosuppressants. Kaposi's sarcoma in patients who have Acquired Immunodeficiency Syndrome (AIDS) is called epidemic Kaposi's sarcoma. Kaposi's sarcoma can be treated with surgery, chemotherapy, radiation therapy and immunotherapy. External radiation therapy is a common treatment of Kaposi's sarcoma. Treatments that can be used in combination with the tubulin inhibitors of the present invention include but are not limited to, local excision, electrodeiccation and curettage, and cryotherapy.

Viral-Induced Cancers

The virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer.

Virus-Induced Hepatocellular Carcinoma

HBV and HCV and hepatocellular carcinoma or liver cancer can appear to act via chronic replication in the liver by causing cell death and subsequent regeneration. Treatments that can be used in combination with the tubulin inhibitors of the present invention include but are not limited to, include surgery, immunotherapy, radiation therapy, chemotherapy and percutaneous ethanol injection. The types of surgery that can be used are cryosurgery, partial hepatectomy, total hepatectomy and radiofrequency ablation. Radiation therapy can be external beam radiation therapy, brachytherapy, radiosensitizers or radiolabel antibodies. Other types of treatment include hyperthermia therapy and immunotherapy.

Viral-Induced Adult T Cell Leukemia/Lymphoma

Adult T cell leukemia is a cancer of the blood and bone marrow. The treatments for adult T cell leukemia/lymphoma that can be used in combination with the tubulin inhibitors of the present invention include but are not limited to, radiation therapy, immunotherapy, and chemotherapy. Radiation therapy can be external beam radiation therapy or brachytherapy. Other methods of treating adult T cell leukemia/lymphoma include immunotherapy and high-dose chemotherapy with stem cell transplantation.

Viral-Induced Cervical Cancer

Infection of the cervix with human papillomavirus (HPV) is a cause of cervical cancer. The treatments for cervical cancers that can be used in combination with the tubulin inhibitors of the present invention include but are not limited to, surgery, immunotherapy, radiation therapy and chemotherapy. The types of surgery that can be used are conization, total hysterectomy, bilateral salpingo-oophorectomy, radical hysterectomy, pelvic exenteration, cryosurgery, laser surgery and loop electrosurgical excision procedure. Radiation therapy can be external beam radiation therapy or brachytherapy.

CNS Cancers

Brain and spinal cord tumors are abnormal growths of tissue found inside the skull or the bony spinal column, which are the primary components of the central nervous system (CNS). Benign tumors are non-cancerous, and malignant tumors are cancerous. Tumors that originate in the brain or spinal cord are called primary tumors. Primary tumors can result from specific genetic disease (e.g., neurofibromatosis, tuberous sclerosis) or from exposure to radiation or cancer-causing chemicals.

The primary brain tumor in adults comes from cells in the brain called astrocytes that make up the blood-brain barrier and contribute to the nutrition of the central nervous system. These tumors are called gliomas (astrocytoma, anaplastic astrocytoma, or glioblastoma multiforme). Some of the tumors are, but not limited to, Oligodendroglioma, Ependymoma, Meningioma, Lymphoma, Schwannoma, and Medulloblastoma.

Neuroepithelial Tumors of the CNS

Astrocytic tumors, such as astrocytoma; anaplastic (malignant) astrocytoma, such as hemispheric, diencephalic, optic, brain stem, cerebellar; glioblastoma multiforme; pilocytic astrocytoma, such as hemispheric, diencephalic, optic, brain stem, cerebellar; subependymal giant cell astrocytoma; and pleomorphic xanthoastrocytoma. Oligodendroglial tumors, such as oligodendroglioma; and anaplastic (malignant) oligodendroglioma. Ependymal cell tumors, such as ependymoma; anaplastic ependymoma; myxopapillary ependymoma; and subependymoma. Mixed gliomas, such as mixed oligoastrocytoma; anaplastic (malignant) oligoastrocytoma; and others (e.g. ependymo-astrocytomas). Neuroepithelial tumors of uncertain origin, such as polar spongioblastoma; astroblastoma; and gliomatosis cerebri. Tumors of the choroid plexus, such as choroid plexus papilloma; and choroid plexus carcinoma (anaplastic choroid plexus papilloma). Neuronal and mixed neuronal-glial tumors, such as gangliocytoma; dysplastic gangliocytoma of cerebellum (Lhermitte-Duclos); ganglioglioma; anaplastic (malignant) ganglioglioma; desmoplastic infantile ganglioglioma, such as desmoplastic infantile astrocytoma; central neurocytoma; dysembryoplastic neuroepithelial tumor; olfactory neuroblastoma (esthesioneuroblastoma. Pineal Parenchyma Tumors, such as pineocytoma; pineoblastoma; and mixed pineocytoma/pineoblastoma. Tumors with neuroblastic or glioblastic elements (embryonal tumors), such as medulloepithelioma; primitive neuroectodermal tumors with multipotent differentiation, such as medulloblastoma; cerebral primitive neuroectodermal tumor; neuroblastoma; retinoblastoma; and ependymoblastoma.

Other CNS Neoplasms

Tumors of the sellar region, such as pituitary adenoma; pituitary carcinoma; and craniopharyngioma. Hematopoietic tumors, such as primary malignant lymphomas; plasmacytoma; and granulocytic sarcoma. Germ Cell Tumors, such as germinoma; embryonal carcinoma; yolk sac tumor (endodermal sinus tumor); choriocarcinoma; teratoma; and mixed germ cell tumors. Tumors of the Meninges, such as meningioma; atypical meningioma; and anaplastic (malignant) meningioma. Non-menigothelial tumors of the meninges, such as Benign Mesenchymal; Malignant Mesenchymal; Primary Melanocytic Lesions; Hemopoietic Neoplasms; and Tumors of Uncertain Histogenesis, such as hemangioblastoma (capillary hemangioblastoma). Tumors of Cranial and Spinal Nerves, such as schwannoma (neurinoma, neurilemoma); neurofibroma; malignant peripheral nerve sheath tumor (malignant schwannoma), such as epithelioid, divergent mesenchymal or epithelial differentiation, and melanotic. Local Extensions from Regional Tumors; such as paraganglioma (chemodectoma); chordoma; chodroma; chondrosarcoma; and carcinoma. Metastatic tumours, Unclassified Tumors and Cysts and Tumor-like Lesions, such as Rathke cleft cyst; Epidermoid; dermoid; colloid cyst of the third ventricle; enterogenous cyst; neuroglial cyst; granular cell tumor (choristoma, pituicytoma); hypothalamic neuronal hamartoma; nasal glial herterotopia; and plasma cell granuloma.

Chemotherapeutics available are, but not limited to, alkylating agents such as, Cyclophosphamide, Ifosfamide, Melphalan, Chlorambucil, BCNU, CCNU, Decarbazine, Procarbazine, Busulfan, and Thiotepa; antimetabolites such as, Methotraxate, 5-Fluorouracil, Cytarabine, Gemcitabine (Gemzar®), 6-mercaptopurine, 6-thioguanine, Fludarabine, and Cladribine; anthracyclins such as, daunorubicin. Doxorubicin, Idarubicin, Epirubicin and Mitoxantrone; antibiotics such as, Bleomycin; camptothecins such as, irinotecan and topotecan; taxanes such as, paclitaxel and docetaxel; and platinums such as, Cisplatin, carboplatin, and Oxaliplatin.

PNS Cancers

The peripheral nervous system consists of the nerves that branch out from the brain and spinal cord. These nerves form the communication network between the CNS and the body parts. The peripheral nervous system is further subdivided into the somatic nervous system and the autonomic nervous system. The somatic nervous system consists of nerves that go to the skin and muscles and is involved in conscious activities. The autonomic nervous system consists of nerves that connect the CNS to the visceral organs such as the heart, stomach, and intestines. It mediates unconscious activities.

Acoustic neuromas are benign fibrous growths that arise from the balance nerve, also called the eighth cranial nerve or vestibulocochlear nerve. The malignant peripheral nerve sheath tumor (MPNST) is the malignant counterpart to benign soft tissue tumors such as neurofibromas and schwannomas. It is most common in the deep soft tissue, usually in close proximity of a nerve trunk. The most common sites include the sciatic nerve, brachial plexus, and sarcal plexus.

The MPNST can be classified into three major categories with epithelioid, mesenchymal or glandular characteristics. Some of the MPNST include but not limited to; subcutaneous malignant epithelioid schwannoma with cartilaginous differentiation, glandular malignant schwannoma, malignant peripheral nerve sheath tumor with perineurial differentiation, cutaneous epithelioid malignant nerve sheath tumor with rhabdoid features, superficial epithelioid MPNST, triton Tumor (MPNST with rhabdomyoblastic differentiation), schwannoma with rhabdomyoblastic differentiation. Rare MPNST cases contain multiple sarcomatous tissue types, especially osteosarcoma, chondrosarcoma and angiosarcoma. These have sometimes been indistinguishable from the malignant mesenchymoma of soft tissue.

Other types of PNS cancers include but not limited to, malignant fibrous cytoma, malignant fibrous histiocytoma, malignant meningioma, malignant mesothelioma, and malignant mixed Müllerian tumor.

Oral Cavity and Oropharyngeal Cancer

Cancers of the oral cavity include but are not limited to, hypopharyngeal cancer, laryngeal cancer, nasopharyngeal cancer, and oropharyngeal cancer.

Stomach Cancer

There are three main types of stomach cancers: lymphomas, gastric stromal tumors, and carcinoid tumors. Lymphomas are cancers of the immune system tissue that are sometimes found in the wall of the stomach. Gastric stromal tumors develop from the tissue of the stomach wall. Carcinoid tumors are tumors of hormone-producing cells of the stomach.

Testicular Cancer

Testicular cancer is cancer that typically develops in one or both testicles in young men. Cancers of the testicle develop in certain cells known as germ cells. The two types of germ cell tumors (GCTs) that occur in men are seminomas (60%) and non-seminomas (40%). Tumors can also arise in the supportive and hormone-producing tissues, or stroma, of the testicles. Such tumors are known as gonadal stromal tumors. The two types are Leydig cell tumors and Sertoli cell tumors.

Secondary testicular tumors are those that start in another organ and then spread to the testicle. Lymphoma is a secondary testicular cancer.

Thymus Cancer

The thymus is a small organ located in the upper/front portion of your chest, extending from the base of the throat to the front of the heart. The thymus contains two main types of cells, thymic epithelial cells and lymphocytes. Thymic epithelial cells can give origin to thymomas and thymic carcinomas. Lymphocytes, whether in the thymus or in the lymph nodes, can become malignant and develop into cancers called Hodgkin disease and non-Hodgkin lymphomas. The thymus cancer includes Kulchitsky cells, or neuroendocrine cells, which normally release certain hormones. These cells can give rise to cancers, called carcinoids or carcinoid tumors.

Treatments that can be used in combination with the tubulin inhibitors of the present invention include but are not limited to, surgery, immunotherapy, chemotherapy, radiation therapy, combination of chemotherapy and radiation therapy or biological therapy. Anticancer drugs that have been used in the treatment of thymomas and thymic carcinomas are doxorubicin (Adriamycin), cisplatin, ifosfamide, and corticosteroids (prednisone).

EXAMPLES

Synthetic Examples

Synthetic Example 1

Synthesis of 1-(4-(3-amino-4-methoxyphenoxy)-3,5-diiodophenyl)ethanone (Formula IIIB)

The synthesis of 1-(4-(3-amino-4-methoxyphenoxy)-3,5-diiodophenyl)ethanone, represented by formula IIIB, was carried out as follows:

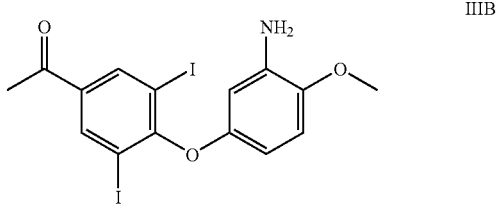

The compound of formula IIIB was synthesized from 1-(3,5-diiodo-4-(4-methoxyphenoxy)phenyl)ethanone (DIPE) according to the following procedure: The synthesis of DIPE has been previously described, e.g. in U.S. Pat. Nos. 5,922,775, 6,303,629, 5,908,861 and 6,326,402.

Nitration of DIPE to Form 1-(3,5-diiodo-4-(4-methoxy-3-nitrophenoxy)phenyl)ethanone Nitration of DIPE was performed with a mixture of 1.4 equiv. 69% nitric acid and 2.2 equiv. 96% sulfuric acid at Ti<5° C. in methylene chloride. The reaction was complete after 30 min. According to TLC a single product was formed, indicating that mono-nitration took place. The product isolated by extractive workup was obtained in 95% yield with a purity of 99.9 area %. As the nitro-reduced product was eventually identified as the compound of formula IIIB, it is inferred that the product of this reaction is 1-(3,5-diiodo-4-(4-methoxy-3-nitrophenoxy)phenyl)ethanone (3-nitro intermediate).

Reduction of Nitro Group to Form the Compound of Formula IIIB

The reduction of the nitro group was carried out with 5.5 equiv. of anhydrous tin(II)chloride in ethanol, 37% HCl solution at Ti<10° C.; afterwards the solution was allowed to warm to room temperature and was stirred at Ti=30-35° C. for 7 hours. The product was isolated as its hydrochloride salt, which was transformed into the free base upon basification with 1N NaOH solution. An impurity at RRT=1.08 was present in 1.9 area %. This impurity was determined to be the nitroso impurity. The crude product was re-crystallized three times from ethyl acetate. The nitroso impurity was thereby reduced to 0.4 area % and the product of formula IIIB was obtained in 99.4 area % purity as a white solid. The structure of formula IIIB and that of the 3-nitro intermediate were determined by NMR studies ($^1$H-, $^{13}$C-, HSQC-, HMBC-, NOESY- and COSY-experiments).

Synthetic Example 2

Synthesis of 1-(4-(3-hydroxy-4-methoxyphenoxy)-3,5-diiodophenyl)ethanone (Formula IIIA)

The synthesis of 1-(4-(3-hydroxy-4-methoxyphenoxy)-3,5-diiodophenyl)ethanone, represented by formula IIIA, was carried out as follows:

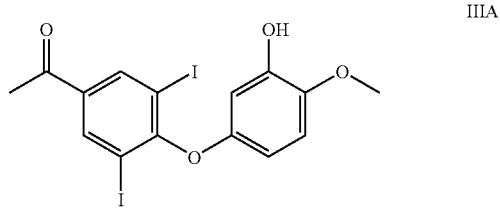

IIIA

Diazonium Salt Formation

A diazonium salt:

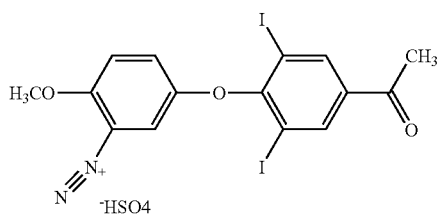

was formed by adding an aqueous solution of NaNO$_2$ (2.0 equiv.; c=1.4 g/mL) at Ti=0-5° C. to a suspension of the compound of formula IIIB, as obtained in synthetic example 1. The reaction was followed by HPLC. The diazonium salt is eluted at RRT of 0.78. Diazonium salt formation was complete within 5 hours. The conversion was 91% and the purity of the diazonium salt was 87.9 area %. Excess nitrous acid was destroyed by addition of urea; and the reaction mixture was tested with starch iodine paper.

Conversion of the Diazonium Salt to the Compound of Formula IIIA

The diazonium salt was added to 6N H$_2$SO$_4$ (30.6 equiv.) and the reaction mixture stirred at Ti=100° C. for 24 hours. The diazonium salt of the compound of formula IIIB was surprisingly stable. Silica gel chromatography (methylene chloride as mobile phase) followed by normal and reverse phase chromatography resulted in 3.9 mg of compound of formula IIIA with a purity of 74.2 area % to 80.9 area %.

Example 1

Effect on Tubulin Polymerization

In the following experiments the candidate tubulin inhibitors, separately or in combination, at 1 to 5 mM concentrations inhibit the GTP-dependent polymerization of MTP as determined by an optical test. This inhibition is critically dependent on the concentration of GTP. The quantitative correlation between the concentrations of candidate tubulin inhibitors and GTP, under conditions of a linear rate of MTP polymerization, follows Michaelis-Menten kinetics and the inhibition portrays a "mixed" type, where km for GTP and Vmax are altered simultaneously. Candidate tubulin inhibitors inhibit MTP polymerization parallel to their anti-tumorigenic action in vivo. The MTP site is one of the early cellular response sites of the candidate tubulin inhibitors.

Exposure of human mammary cancer cells (MDA-MB-231) to 1 mM of a candidate tubulin inhibitor induces abnormal spindle structures within 18 hours of drug treatment, thus a putative candidate tubulin inhibitor-microtubule-protein (MTP) interaction appears to be a component of early cellular responses to the drug. Abnormal spindle structures could be the result of candidate tubulin inhibitor-MTP interaction or reactions of a candidate tubulin inhibitor with components of the microtubule organizing center or with as yet undefined systems sequentially or in concert. Since time-dependent quantitative analysis of the MTP system in situ is unsuitable for initial velocity measurement we adapted the in vitro assembly system of neurotubules as a model for a quantitative analysis of the interaction of a candidate tubulin inhibitor with MTP. As demonstrated by Gaskin, et al., 1974, "Turbidimetric studies of the in vitro assembly and disassembly of porcine neurotubules", J. Mol. Biol. 89:737-758; and Kirschner, et al., 1974, "Microtubules from mammalian brain: some properties of their depolymerization products and a proposed mechanism of assembly and disassembly", Proc. Natl. Acad. Sci. U.S.A. 71:1159-1163; this system is suitable for kinetic assay of MTP assembly in vitro. The time course of MTP assembly consists of initiation and propagation and termination steps, Gaskin, et al., 1974, "Turbidimetric studies of the in vitro assembly and disassembly of porcine neurotubules", J. Mol. Biol. 89:737-758. The rate of propagation under defined conditions is sufficiently linear to permit kinetic analysis that can be evaluated with respect candidate tubulin inhibitor and GTP concentrations. As we show here the inhibition of MTP assembly by candidate tubulin inhibitors occurs in the same range of drug concentration as required to inhibit tumorigenesis in vivo, or to inhibit cell replication or induce eventual cell death; Mendeleyev, et al., 1997. "Structural specificity and tumoricidal action of methyl-3,5-diiodo-4-(4'-methoxyphenoxy)benzoate (DIME)" Int. J. Oncol., 10:689-695. Therefore the a candidate tubulin inhibitor-MTP interaction is most probably a component of the apparently pleiotropic cellular mechanism of action of DIME.

Isolation of Microtubule Proteins (MTP)

Preparation of MTP and an optical test for polymerization is adopted from published methods, Gaskin, et al., 1974, "Turbidimetric studies of the in vitro assembly and disassembly of porcine neurotubules", J. Mol. Biol. 89:737-758; Tiwari, et al., 1993, "A pH and temperature-dependent cycling method that doubles the yield of microtubule protein", Anal. Biochem. 215:96-103. Bovine or rabbit brain is homogenized in an equal volume of ice cold buffer containing 100 mM Pipes/K+ (pH 7.4), 4 mM EGTA. 1 mM $MgCl_2$, 0.5 mM DTT and 0.1 mM PMSF, and centrifuged at 39,000 g for 1 hour at 4° C. To the supernatant, DMSO (8% final concentration) and GTP (1 mM final concentration) are added, followed by incubation at 37° C. for 30 minutes. Microtubules are pelleted at 100,000 g at 37° C. for 30 minutes. The pellets are incubated on ice for 15 minutes, followed by resuspension in ice cold PEM buffer (100 mM Pipes/K+ (pH 6.9), 1 mM EGTA, 1 mM $MgCl_2$). This warm polymerization and cold depolymerization cycle is repeated once more and the cold, resuspended monomeric MTP (8-10 mg/ml protein) is used for the optical test for polymerization kinetics. Both rabbit or bovine brain yields identical MTP preparations.

The polymerization reaction is started by the addition of 100 ml of MTP solution (equivalent to 0.8-1.0 mg protein) and initial linear rates of increase in absorbance at 350 nm follows and is recorded at 37° C. in a Perkin-Elmer 552 double beam spectrophotometer, equipped with a thermostatically controlled cuvette holder.

Inhibition of MTP polymerization can have highly complex cellular consequences. In cytokinesis, this inhibition can interfere with traction forces of tubulin and prevent the formation of a cleavage furrow which is essential for cell division, Burton, et al., 1997, "Traction forces of cytokinesis measured with optically modified elastic substrate", Nature 385:450-454. The inhibition of MTP polymerization by candidate tubulin inhibitors should be correlated with the biochemical sites of this drug.

On the basis of these experiments, it can be seen that thyroxine type analogues, such as the candidate tubulin inhibitors, are capable of blocking mitosis in cancer cells.

Example 2

Anti-Tumor Efficacy of Antitubulin Inhibitors

In Vitro Cytotoxicity Screen Against Human Tumor Cell Lines.

Human tumor cell lines are exposed continuously to varying concentrations of test agents (i.e., candidate tubulin inhibitors) and the viability of the cells are measured at set time points (1, 3, and 7 days) using the alamar Blue™ assay. When alamar Blue™ dye is added to culture medium, the dye is reduced by cellular mitochondrial enzymes yielding a soluble product with substantially enhanced fluorescence. This fluorescence is measured with a fluorimeter, whereby the signal is directly proportional to cell number.

Various tumor cell lines of human origin representing a wide diversity of cancer phenotypes and genotypes are exposed in vitro to the candidate tubulin inhibitors to evaluate the drugs' effective range. Tumor lines that are screened include MDA-MB-231 (breast), MCF-7 (breast), MDA-MB-468 (breast), Siha (squamous cell carcinoma), A549 (non-small cell lung), HL-60 (leukemia), and Ovcar-3 (ovarian). The test agents are prepared in serial dilutions from 10 mM stock solutions in DMSO yielding a 66-fold dose range of 20 µM, 10 µM, 3 µM, 1 µM and 0.3 µM concentrations. In each case, cells are maintained at 37° C. in 5 percent $CO_2$ in air. All cell lines are incubated in Dulbecco's modified Eagle medium (DMEM) supplemented with 10% heat-inactivated fetal bovine serum and graded doses of candidate tubulin inhibitors. 5-Fluorouracil (5-FU) is included as a positive control in experiments with some the cell lines. The experiments are conducted in 96-well tissue culture plates (Falcon) with an initial seeding density of 1000 cells per well in 250 µL aliquots. The next day, medium is replaced with 100 µL of drug dilutions in triplicate.

After a 7 day exposure to the various agents, the alamar Blue™ dye is diluted to 20% in DMEM, and 100 µL is added to each well. The cells are incubated for 8 hours until obvious color changes indicate sufficient amounts of reduced dye for quantitation. Relative cell number is evaluated by fluorimetry on a Millipore 2300 CytoFluor fluorescence measurement system. Measurements are taken directly from 96-well plates after excitation at 560 nm with concomitant emission at 590 nm. IC50 values are calculated vs. control (non-treated cells).

Example 3

In Vitro Metabolism of Candidate Tubulin Inhibitors in Human Leukemia Cells

In humans and laboratory animals, enzyme systems in the liver are capable of metabolizing a large number of chemicals to inactive forms, and some chemotherapeutic agents are inactive unless they are metabolized to active forms. To test for either of these possibilities, the candidate tubulin inhibitors are incubated with a microsomal enzyme fraction, referred to as S9.

Human leukemia (HL60) cells are used to evaluate drug metabolism. Exposure to the test article is performed in the presence and absence of S9, prepared from the liver of adult male rats given a single intraperitoneal injection of Arachlor 1254 (500 mg/kg). The S9 consists of the 9000×G supernatant of liver homogenized in 0.25 M sucrose-100 mM phosphate buffer (pH 7.4) (Molecular Toxicology, Inc.). Cofactors are 1 mM NADP and 5 mM sodium isocitrate. On the day of exposure, cultures of cells, with or without the metabolism mixture, are incubated for 4 hours in RPMI containing 5% FBS and graded doses of candidate tubulin inhibitors. The candidate agents are prepared in serial dilutions from 10 mM stock solutions in DMSO yielding a dose range 100 µM, 50 µM, 25 µM, 10 µM and 5 µM concentrations and a final DMSO concentration of 1%. In each case, cells are maintained at 37° C. in 5 percent $CO_2$ in air. The experiments are conducted in 6-well tissue culture plates (Falcon) with an initial seeding density of $2\times10^6$ cells per well in 2 ml aliquots. The test compounds are added immediately to the medium in duplicate cultures. Treatment solution is removed by a series of low-speed centrifugations to pellet the cells, followed by removal of the supernatant and resuspension of cells in fresh RPMI containing 10% FBS.

Example 4

In Vivo Efficacy of Candidate Tubulin Inhibitors Against Met-1 Mouse Mammary Tumors Mammary fat pads of Balb/c immunodeficient (nude) mice are implanted with 1 $mm^3$ of mammary tumor tissue. These mammary tumors originate from the met-1 mouse mammary tumor cell line and are been propagated by passaging in vivo. When palpable tumors appear, animals are subdivided into various treatment groups and treated daily with intraperitoneal injections of control vehicle, and candidate tubulin inhibitors (50 mg/kg). A group of untreated control animals are included in the study, because agents used in the vehicle for these test articles (DMSO/ethanol/Cremophor EL/PEG 400, 1:0.5:0.5:6) are themselves found to have cytotoxic activity. Twice weekly, the volumes of the tumors in each animal in each group are measured to gather information on tumor growth (volume) as a function of type of treatment, dose, and time.

Example 5

Anti-Angiogenic Properties

The Chick Chorioallantoic Membrane (CAM) Assay

Candidate tubulin inhibitors are tested in the CAM assay. The endpoint of the CAM assay is a quantitative determination of basement membrane biosynthesis by measuring the incorporation of $^{14}$C-proline into Type IV collagenous protein.

The CAM assay involves the development of live chick embryos in Petri dishes under special sterile conditions. Therefore, only limited numbers of embryos can be used for evaluation of compounds in a single experiment. Candidate tubulin inhibitors are tested in separate assays. A known angiogenesis inhibitor, 2-methoxyestradiol (2-ME), is used as the positive control, and human fibroblast growth factor (hFGF) is used to induce angiogenesis in the CAM.

Fertilized eggs are supplied by Melody Ranch, Aptos, Calif. L-[U-$^{14}$C] proline (specific activity, 290 mCi/mmol) is purchased from New England Nuclear, Boston, Mass. Collagenase and 2-ME were obtained from Sigma Chemical Co., St. Louis, Mo. Silicone ring cups are obtained by cutting silicone tubing (3 mm diameter) into small "O" rings 1 mm in thickness. These silicone ring cups can be reused many times if they are sterilized prior to each assay. Plastic Petri dishes (20×100 mm) are purchase from Baxter diagnostics, Inc., Hayward, Calif. hFGF-B is obtained from Clonetics Corporation, San Diego, Calif.

For testing, a minimum amount of acetone-methanol (1:1) is added to the test compounds for sterilization. The acetone-methanol mixture is then evaporated to dryness in a sterile hood. The compounds are dissolved in dimethyl sulfoxide (DMSO) first and subsequently diluted with saline containing methylcellulose. The final concentrations are 2% DMSO and 0.5% methylcellulose. All test solutions are added to each CAM in 20-ml aliquots.

The method of Folkman, et al. (Folkman, et al. (1974) Dev. Biol. 41:391-394) with some modifications, is used to cultivate chicken embryos as follows:

Fresh fertile eggs are incubated for three days in a standard egg incubator. On Day 3, eggs are cracked under sterile conditions and embryos are placed in 20×100 mm plastic Petri dishes and cultivated at 37° C. in an embryo incubator with a water reservoir on the bottom shelf. Air is continuously bubbled into the water reservoir by using a small pump so that the humidity in the incubator is kept constant. Observations are made daily to ensure that all embryos are healthy. Dead or unhealthy embryos are removed from the incubator immediately to avoid contamination. On Day 9, a sterile silicone ring cup is placed on each CAM and 0.5 mCi of $^{14}$C-proline with or without the test compound plus 2.5 ng of hFGF dissolved in saline containing 0.5% methylcellulose is delivered into each ring cup in a sterile hood. 2-ME id tested in parallel to serve as a reference compound. After addition of test materials, the embryos are returned to the incubator and cultivation continued. On Day 12, all embryos are transferred to a cold room at 4-10° C. The anti-angiogenic effect of each test compound is determined by using the collagenase assay to measure $^{14}$C-proline incorporation into collagenous protein.

Example 6

Collagenase Assay for Measurement of $^{14}$C-Proline Incorporation into Collagenous Protein Using the procedure outlined in Maragoudakis, et al., (1989) J. Pharm. Exp. Ther. 251:679-682, the embryos are placed on ice, and a piece of CAM 10 mm in diameter is cut off under each ring cup and placed in a separate tube. To each tube is added 1.0 ml of phosphate-buffered saline (PBS, pH 7.3) containing 0.11 mg cycloheximide and 0.17 mg dipyridyl. The tubes are placed in a boiling water bath for 10 min and then cooled to room temperature. The PBS in each tube is discarded after centrifugation at 3000×G for 10 min. The CAM residue is washed once with 3 ml of 15% TCA and then three times with 3 ml of 5% TCA. Centrifugation is carried out as described above between each washing. At this point all non-protein bound radioactivity was removed, and the CAM containing the newly synthesized $^{14}$C-collagenous protein is suspended in 0.9 ml of 0.1 N NaOH and 1.1 ml of HEPES buffer at pH 7.4. The pH of the sample is neutralized with 0.8 N HCl, using phenol red as indicator.

To digest the $^{14}$C-collagenous protein, 7.5 units of collagenase and 500 nmol of calcium chloride in 40 ml of HEPES buffer is added to the above samples, and mixtures are incubated at 37° C. for 4 h. The reaction is stopped by adding 1.0 ml of 20% TCA containing 5 mg of tannic acid into each tube. After vortex mixing, the samples are centrifuged at 3000×G for 10 min. An aliquot of the clear supernatant was taken for scintillation counting to quantitate the radiolabeled tripeptides corresponding to basement membrane collagen and other collagenous materials synthesized by the CAM from $^{14}$C-proline. The CAM pellets in each tube are solubilized in 0.5 ml of 1.0 N NaOH by boiling in a water bath for 5 min. An aliquot of the dissolved CAM is used for protein determination using the method provided by Pierce Chemical Co. The radioactivity per milligram of protein from the CAM treated with a test compound relative to that from the control CAM gives the percent of angiogenesis inhibition.

Example 7

Assays Used to Screen for Anti-Mitotic Properties

Microtubule Assembly Inhibition Assay

A cell-free assay for measuring inhibition of the microtubule assembly can be performed by first mixing tubulin and rhodamine-labeled tubulin at a ratio of 4:1 (Hyman, A., et al. (1990) Meth. Enzymol. 196, 478-485; Belmont, L. D., et al. (1996) Cell 84, 623-631). This tubulin solution is then added on ice to a buffer (BRB 80; 80 mM potassium salt of PIPES (pH 7.5), 5 mM MgCl$_2$, 1 mM EGTA) containing 1 mM GTP and 1 mM DTr to a 15 µM final concentration. Drugs at different concentrations (0.5 µl) are added to 50 µl samples of the buffered tubulin, and 10 µl of each solution is transferred to microfuge tubes. Each tube receives 0.4 µl of microtubule seeds (Belmont, L. D., supra). Tubes are incubated at 37° C. for 10 min before adding 100 µl of BRB 80 containing 1% glutaraldehyde. Each reaction mixture (2.5 µl) is transferred to a microscope slide for fluorescence microscopy.

Microtubules in intact cells are visualized by using a mouse anti-tubulin monoclonal antibody and a fluorescein-labeled donkey anti-mouse polyclonal antibody. Briefly, HeLa cells are plated in 2-well chamber slides (Nunc, Napierville, Ill.) at $1.5 \times 10^4$/ml and incubated in 5% $CO_2$ at 37° C. for 24 h before treatment with drugs for 1 h. After removing the medium, cellular microtubules are stabilized by using BRB 80 containing 4 mM EGTA and 0.5% Triton X-100. The cells are fixed for 3 min in methanol chilled at −20° C., washed with TBS buffer (0.15 M NaCl, 0.02 M Tris-HCl, pH 7.4), and permeabilized with TBS/0.5% Triton X-100. After several washes with TBS/0.1% Triton X-100, the cells are blocked with an antibody dilution buffer (TBS, 0.1% Triton X-100, 2% BSA, 0.1% sodium azide) for 10 min. The cells are stained in the dark with the primary antibody for 1.5 h, and then the secondary antibody is added in the antibody dilution buffer containing 1 μg/ml Hoechst 33342 and incubated in the dark for 45 min. The slides are mounted with n-propyl gallate (2% w/v in 30% 0.1 M Tris/glycerol, pH 9.0) and sealed under glass cover slips.

Example 8

Competitive Tubulin-Binding Assay

The competitive binding of a compound to the colchicine binding site of tubulin is performed by using a spin column method (Woods, J. A., et al. (1995) British J. Cancer 71, 705-711). $^{14}$C-labeled candidate tubulin inhibitor (20 μM, 10 nCi) is mixed with tubulin and colchicine at different concentrations and incubated at room temperature for 1.5 h in a buffer containing 0.1 M MES (pH 6.8), 1 mM EGTA, 1 mM EDTA, and 1 mM $MgCl_2$. Each reaction mixture is loaded onto a column containing 1 ml of Sephadex G50 equilibrated with a buffer containing 40 mM MES (pH 7.5), 40 mM Tris, and 1 mM $MgSO_4$. The columns are centrifuged at 900×G for 3 min and the eluents are each mixed with 3 ml of CytoScint (ICN) for analysis by liquid scintillation counting.

Example 9

Use of the Candidate Tubulin Inhibitors as Sensitizers for Radiotherapy

In Vitro Radiosensitization Assay

Radiosensitization studies are performed on cancer cells grown in culture. The test compound is added to the cells prior to, during, or after irradiation. Radiation dosages are typically measured in units of Gy/min, with one Gy is equal to 100 rads, while one rad is the quantity of ionizing radiation that results in the absorption of 100 ergs of energy per gram of irradiated material. Sensitization enhancement ratios (SER) are determined at a 10% survival level. The C1.6 value (i.e., a concentration of test compound yielding an SER of 1.6) is determined by plotting SER values against test compound concentration.

HeLa S-3 cells are grown and maintained in modified Eagles's medium containing 10% fetal bovine serum in a humidity and $CO_2$-controlled incubator. Experimental studies are initiated on exponential cultures growing in 60 mm tissue culture dishes at treatment densities of $3-7 \times 10^5$ cells/dish. The doubling time of HeLa S-3 cultures is typically approximately 18 hours.

A compound of formula (I) is dissolved in distilled water just prior to use and diluted 1:100 through addition of the appropriate volume to cultured cells. For ultraviolet irradiation studies, compound is added only during the repair period following irradiation. For X-irradiation studies, drug is added to cultures 1 hour prior to irradiation and remains in contact with cells during irradiation.

For ultraviolet (non-ionizing) irradiation, all medium is removed from cultures and, with the lid removed, dishes are exposed to 1.4 J/M2 of UV254 nm light emitted from a G.E. germicidal lamp. Fresh media with or without test compound is then added to cultures during the subsequent repair period. In some cases, cells are harvested immediately in order to establish a T0 value for DNA strand breaks. X-irradiation (ionizing) of cultures is carried out in a TFI Bigshot X-ray unit at 3 mA, 50 keV, filtered with 1.5 mm Be and delivering 0.56 Gy/min to the cells (through the lid and 5 mls of media) as determined by a Victoreen ionization chamber calibrated in the 10 to 50 keV range. Following X-irradiation, cultures are harvested immediately for colony forming ability assays. D0 values are calculated from survival curves computer plotted by linear regression analysis.

The ability of cells to form colonies after irradiation is determined by standard methods. Cultures treated with test compound are irradiated and immediately trypsinized, counted and re-plated in 5 ml medium containing the appropriate number of cells (500 for untreated cultures and cultures exposed to 2.8 Gy X-rays; 2,000 for cultures exposed to 20 J/M2 UV; 5,000 for cultures exposed to 5.6 Gy X-rays and 10,000 for cultures exposed to 8.4 Gy X-rays). Cultures are grown for 10 days at which time colonies of 1.0-2.0 mm (50-200 cells) are evaluated by methanol fixation and staining. Untreated HeLa cells exhibit cloning efficiencies in the range of 34 to 46% using this protocol.

In Vivo Radiosensitization Assay

This example describes one method by which one of skill in the art can assay the effect of the compounds of the invention on radiotherapy of malignant tumors. The model system used in this study is well established for determining the effects of radiation on tumor tissue. See, e.g., Twentyman, et al. (1980) J. Nat'l. Cancer Inst. 64: 595-603; Brown, et al. (1980) J. Nat'l. Cancer Inst. 64: 603-611; Bernstein, et al. (1982) Radiation Res. 91: 624-637. The model uses RIF-1 tumor cells, which are well suited to studies of radiation response, including in vitro cell survival and in vivo tumor studies, in part because of its rapid growth rate, with a doubling time of 65 hours and a cell cycle time of 12 hours. The RIF-1 tumor is minimally immunogenic, and metastasizes only at a late stage of growth.

Tumors are produced by the subcutaneous inoculation into the lower backs of mice. This inoculation consists of a suspension of $2 \times 10^5$ RIF-1 cells from culture in 0.25 ml of alpha minimum essential media (MEM, Gibso) supplemented with 10% fetal bovine serum (Johns Scientific). Male C3H/He mice (Harlan Sprague Dawley Inc., Indianapolis, Ind.) that are 5 to 7 weeks old at the time of inoculation are suitable for these experiments. Animals are anaesthetized for the inoculation.

The tumors are then allowed to grow to 1 cm in average diameter. Measurements are made using a caliper, talking the tumor length and width and calculating the average of these two. Tumor diameter measurements are taken every 2 to 3 days from the time the tumor cells were implanted.

Tumors are allowed to grow to approximately 1 cm average diameter without any intervention. Upon the tumors reaching this average diameter, the subject animals are randomized into one of three groups. One group receives no radiation and no test compound, a second group receives radiation and no test compound and a third group receives radiation and test compound.

For radiation treatment, each animal receives a general anesthetic. Animals immobilized and placed in the radiotherapy apparatus for the same period of time. The radiation exposure consists of a single dose of 3000 cGy of 150 KeV X-irradiation (mean time 10 minutes, 40 seconds). Preferably, the radiotherapy equipment (Protea ionization chamber) is calibrated before and after each session to ensure absolute uniform dosing. The radiotherapy is administered with a cone over the tumor and lower back of the animal, which in every case assures a uniform maximal delivery dose to the tumor while minimizing dose delivery to the sensitive structures of the abdomen and upper pelvis.

Those animals randomized to the test compound-treated group receive an intravenous dose of a candidate tubulin inhibitor. The day the subject animal is treated is designated "Day Zero". At frequent intervals, usually every other day, the tumors are measured in the same fashion as previously described, and an average of two diameters calculated. These data are plotted as a function of time. The end-point of the study occurs when the tumor reaches double the original treatment diameter, or approximately 2 cm. Animals are euthanized in a $CO_2$ chamber and the tumors removed surgically post-mortem. Representative tumors are sectioned, paraffin embedded and slides are stained using H&E stain and examined to confirm the histological presence of RIP-1 fibrosarcoma. Animals are sacrificed and tumors harvested before the tumor reaches twice the original diameter in the following situations: premature death of animal following treatment; ulceration of the tumor; or infection or inflammation of the injection site.

Following the termination of the experiment, growth curves for each subject tumor are completed and a line of best fit assigned for purposes of interpolation between data points. The average diameter (AD) of each tumor is then determined for each day of the study from the lane of best fit.

Example 10

Use of Candidate Tubulin Inhibitors as Sensitizers for Chemotherapy

Assays for determining appropriate dosages of the compounds of the invention for use as sensitizers for chemotherapy and immunotherapy are similar to those described for radiotherapy. To examine the "pre-incubation effect" of the compounds of the invention, cancer cells are exposed to a fixed concentration of a candidate tubulin inhibitor test compound for 2 hours, followed by exposure to varying concentrations of a chemotherapeutic or immunotherapeutic agent for 1 hour at 37° C., and then assayed for colony formation. In evaluating the effect of "pre-incubation time" on chemosensitization, cancer cells are exposed to fixed concentrations of the test compound for 0 to 4 hours at 37° C., followed by exposure to a chemotherapeutic agent under aerobic conditions for 1 hour at 37° C., and then assayed for colony formation. Test compound dose-dependent potentiation also is examined by exposing cancer cells to various test compound concentrations for 2 hours at 37° C., and then to a fixed dose of each chemotherapeutic agent for 1 hour at 37° C. under aerobic conditions. Experiments using a simultaneous addition of the sensitizer and chemotherapeutic agent for 1 hour at 37° C. under aerobic conditions can also be performed.

Example 11

Chemoprevention

The efficacy of the claimed compounds as a chemopreventive agent can be demonstrated using in vitro and in vivo models of 5AzadC-induced carcinogenesis. A suitable model system uses pre-malignant murine fibroblasts (cell lines 4C8 and PR4) that express a transcriptionally activated c-Ha-ras protooncogene. These non-tumorigenic cells, which are highly susceptible to malignant conversion by pharmacological doses of 5AzadC, are subclones of mouse NIH 3T3 fibroblasts, PR4N and 4C8-A10 (designated here PR4 and 4C8) and have been previously described (see, e.g., Wilson, et al. (1986) Anal. Biochem., 152: 275-284; Dugaiczyk (1983) Biochem. 22:1605-1613). Both cell lines are phenotypic revertants isolated from LTR/c-Ha-ras1-transformed 3T3 cells after long-term treatment with murine interferon alpha/beta. Cultures are maintained in Dulbecco's modified Eagle's medium (DM supplemented with 10% heat inactivated fetal calf serum (Gibco) and antibiotics. The sodium salts of phenylacetic and phenylbutyric acids (Elan Pharmaceutical Corporation) are dissolved in distilled water. 5AzadC (Sigma St. Louis, Mo.) is dissolved in phosphate buffered saline (PBS) and stored in aliquots at −20° C. until use. Exposure of 5AzadC to direct light is avoided at all times to prevent drug hydrolysis.

For in vitro tests, cells are plated at $1-2\times10^5$ cells in 100 mm dishes and the test compound added to the growth medium at 20 and 48 hrs later. The cells are subsequently subcultured and observed for phenotypic alterations. Whereas untreated 4C8 and PR4 form contact-inhibited monolayers composed of epithelial-like cells, transient exposure of these cultures to 0.1 µM 5AzadC during logarithmic phase of growth results in rapid and massive neoplastic transformation. Within one week of 5AzadC treatment, the great majority of the cell population becomes retractile and spindly in shape and form multilayered cultures with increased saturation densities, which is indicative of loss of contact inhibition of growth. Treatment of the cells with the test compound reduces or prevents these phenotypic changes. The test compound can be administered prior to treatment of the cells with 5AzadC, simultaneously with 5 AzadC treatment, or after 5AzadC treatment.

For in vivo tests of the ability of the test compounds to prevent malignancy, 6-9 week-old female athymic nude mice are inoculated subcutaneously (s.c.) with $0.5\times10^6$ cells. Twenty four hours later 400 µg of freshly prepared 5AzadC in 200 µl PBS is administered intraperitoneally (i.p.) into each animal (approximately 20 mg/kg). The test compound is also administered to the animal. The number, size, and weight of tumors is recorded after 3-4 weeks. For histological examination, tumors are excised, fixed in Bouin's solution (picric acid: 37% formaldehyde: glacial acetic acid, 15:5:1 vol/vol), and stained with H&E. A single i.p. injection of mice with 5AzadC (20 mg/kg) typically results in tumor development at the site of 4C8 cell inoculation in controls. However, animals protected by a compound of the invention either fail to develop tumors or form slow-growing lesions at the site of 4C8 inoculation.

An additional test of the ability of the compounds of the invention to prevent malignant growth involves inhibition of cell growth on matrigel, which is a reconstituted basement membrane (Collaborative Research). This assay models the ability of cells to degrade and cross tissue barriers. Cells are exposed for 48 hrs in plastic tissue culture dishes with 5AzadC alone or in combination with the test compound. Treatment with the test compound is continued for an additional 1-2 weeks, after which cells are re-plated onto 16 mm dishes that were previously coated with 250 µl of matrigel (10 mg/ml). The test compound is either added to the dishes or omitted in order to determine whether the effect is reversible. In the absence of test compound, net-like formation characteristic of invasive cells typically occurs within 12 hours, and invasion into the matrigel is evident after 6-9 days.

Example 12

Assay for Measuring the Ability of Candidate Tubulin Compounds to Reduce the Levels of Tumor Necrosis Factor (TNF-Alpha)

This example provides an assay that can be used to screen compounds of Formula I for their ability to reduce the expression of cytokines (e.g., TNF-alpha) in a mammal.

Cell Line

The murine macrophage PU5-1.8 cell line is purchased from the American Type Culture Collection (ATCC, Rockville, Md.). Cells are grown in DMEM medium supplemented with 100 mM sodium pyruvate, 0.1 mM nonessential amino acids, 2 mM glutamine and 5% fetal bovine serum (Life Technologies, Staten Island, N.Y.). Cells are maintained in a humidified atmosphere of 5% $CO_2$-95% air at 37° C. Cells are passaged twice weekly by firmly tapping the side of the flask to dislodge the adherent cells. Both non-adherent and adherent cells are passaged. Exponentially growing cells are seeded at $5 \times 10^5$/mL, 4 mL per 60-mm dish 24 h prior to the experiment. Test compounds are delivered in 1 mL volumes of the medium added to each dish at the start of the experiment. All dishes are incubated at 37° C. in 5% $CO_2$-95% air for 3 h.

Reagents.

The Tumor Necrosis Factor (TNF-alpha) cDNA is obtained from the ATCC (Rockville, Md.). [alpha-$^{32}$P]-dCTP (250 µCi) and nylon membranes (Hybond N) are obtained from Amersham (Arlington Heights, Ill.). Colchicine (used as a control) is purchased from the Sigma Chemical Company (St. Louis, Mo.). Lipopolysaccharide (LPS) from *Escherichia coli* is purchased from DIFCO Laboratories (Detroit, Mich.). All plastic supplies are purchased from VWR Scientific products (San Francisco, Calif.).

Northern Blotting

Total RNA is isolated by the guanidinium-cesium chloride method as described before (N. S. Waleh, et al., 1994, Cancer Res., 54:838-843). Five to 10 µg of total RNA is electrophoresed in 1% agarose gels containing 6% formaldehyde. Following electrophoresis, gels are stained with ethidium bromide to visualize the positions of 28S and 18S RNA. The RNA is then transferred to nylon membranes (Amersham Hybond N) by capillary blotting and fixed to the filter by exposure to UV light. The blots are probed with $^{32}$P-labeled cDNA sequences of human TNF-alpha obtained from the American Type Culture Collection (ATCC). The TNF-alpha cDNA is a 1.1 kb PstI fragment of plasmid pE4 in *E. coli* MM294 (ATCC 39894). Hybridizations is carried out at 42° C. in 50% formamide, 5×SSC, 5× Denhardt's solution, 0.1% SDS, and 0.3 mg/mL salmon sperm DNA. Filters are washed by 1×SSC, 0.1% SDS, twice at room temperature for 15 min and once at 55° C. in 0.1×SSC, 0.1% SDS for 1 hr. Filters are exposed to X-ray film at −70° C. using an intensifying screen (Coronex Hi-Plus).

Hybridized bands are quantified by analyzing the images obtained by using a video densitometer (Applied Imaging Corporation, Santa Clara, Calif.). Film densities are calibrated using an optical-density wedge.

Treatment of PU5-1.8 murine macrophages with LPS (100 ng/mL) for 3 h results in a significant increase (>7 fold) in the level of TNF-alpha mRNA as determined by Northern blot analysis. Treatment of cells with colchicine at 10 µM concentration has no effect on TNF-alpha mRNA expression. However, addition of colchicine at 10 µM to the LPS treated cultures resulted in substantial reduction of TNF-alpha mRNA accumulation. The inhibition levels were 68% for colchicine.

To establish a concentration-effect relationship, macrophages are exposed to various concentrations of candidate tubulin inhibitors in the presence of the stimulus LPS for 3 h. The amounts of TNF-alpha mRNA declines with increasing concentrations of the candidate tubulin inhibitors. Thus, the above assay can be used to show that candidate tubulin inhibitors have the ability to reduce the level of TNF-alpha produced by a cell.

Example 13

Cell Cycle Analysis with Flow Cytometry

The bromodeoxyuridine (BrdU) method for the analysis of the cell cycle can be used for the study of cell kinetics. Bromodeoxyuridine is an analogue of the DNA base thymidine and can compete with that base for uptake during the synthesis of DNA. So those cells that have been actively synthesizing DNA during the time that BrdU is present can be positive for it. It can be detected by a monoclonal antibody and by simultaneously staining for DNA content with propidium iodide. The percentage of cells in G0/G1, S and G2/M can be determined. By altering the time that BrdU is present cell cycle times can also be assessed. The protocol used in this analysis is as follows. Cells are treated with 10 µM BrdU for an appropriate time (30 mins). After harvesting and washing cells, the cells are fixed in ice-cold 70% ethanol while vortexing. Samples can stay in ethanol for up to 7 days. Sample is spun at 2000 rpm, 5 min. Sample is washed twice in PBS. Cells are treated with 2M hydrochloric acid for 20 min. at room temperature with frequent mixing. Acid is spun off (2000 rpm, 5 min.) and washed twice in PBS and once in PBS-T (PBS+0.5% Tween+0.05% w/v BSA). A 50 µl anti-BrdU antibody (Sera Lab) is added, and left for 15 min. at room temperature. It is then washed twice in PBS-T. A 50 µl FITC-conjugated goat-anti-rabbit immunoglobulins (DAKO) is added to it, and left for 15 min. at room temperature. It is then washed once in PBS-T. A 100 µl Ribonuclease, and 400 µl propidium iodide (Stock is 50 µg/ml) is then added. Analyses is done by flow cytometry (Fabbri F. et al. 2006, BMC Cell Biology, 7:6).

It is to be understood that the above descriptions are intended to be illustrative and not restrictive. Many embodiments will be apparent to those of skill in the art upon reading the above descriptions. The scope of the invention should, therefore, be determined not with reference to the above descriptions, but should instead be determined with reference to the appended claims, along with the full scope of equivalents to which such claims are entitled. The disclosures of all articles and references, including patent applications and publications, are incorporated herein by reference for all purposes.

Example 14

Cell Cycle Analysis

HCT116 and Hela cells were obtained from ATCC. For DNA content analysis, $2 \times 10^5$ cells were washed twice with PBS and fixed in 70% ethanol. Cells were treated with 100 units/mL RNase A for 20 minutes at 37° C., resuspended in cold PBS containing Alexa Fluor® 405 fluorescent stain (Invitrogen) according to the manufacturer's protocol. Cells were analyzed by flow cytometry.

For DNA replication analysis, 2×105 cells were incubated with 50 µmol/L bromodeoxyuridine (BrdUrd) for 30 minutes. Cells were fixed in 70% ethanol and BrdUrd incorporation was determined by flow cytometric analysis using an anti-BrdUrd-FITC antibody (Becton Dickinson, Franklin Lakes, N.J.) according to the manufacturer's protocol. To assess the degree of G2/M checkpoint, mitotic cells were detected by flow cytometry using the mitosis-specific antibody GF-7.

Figure 6:
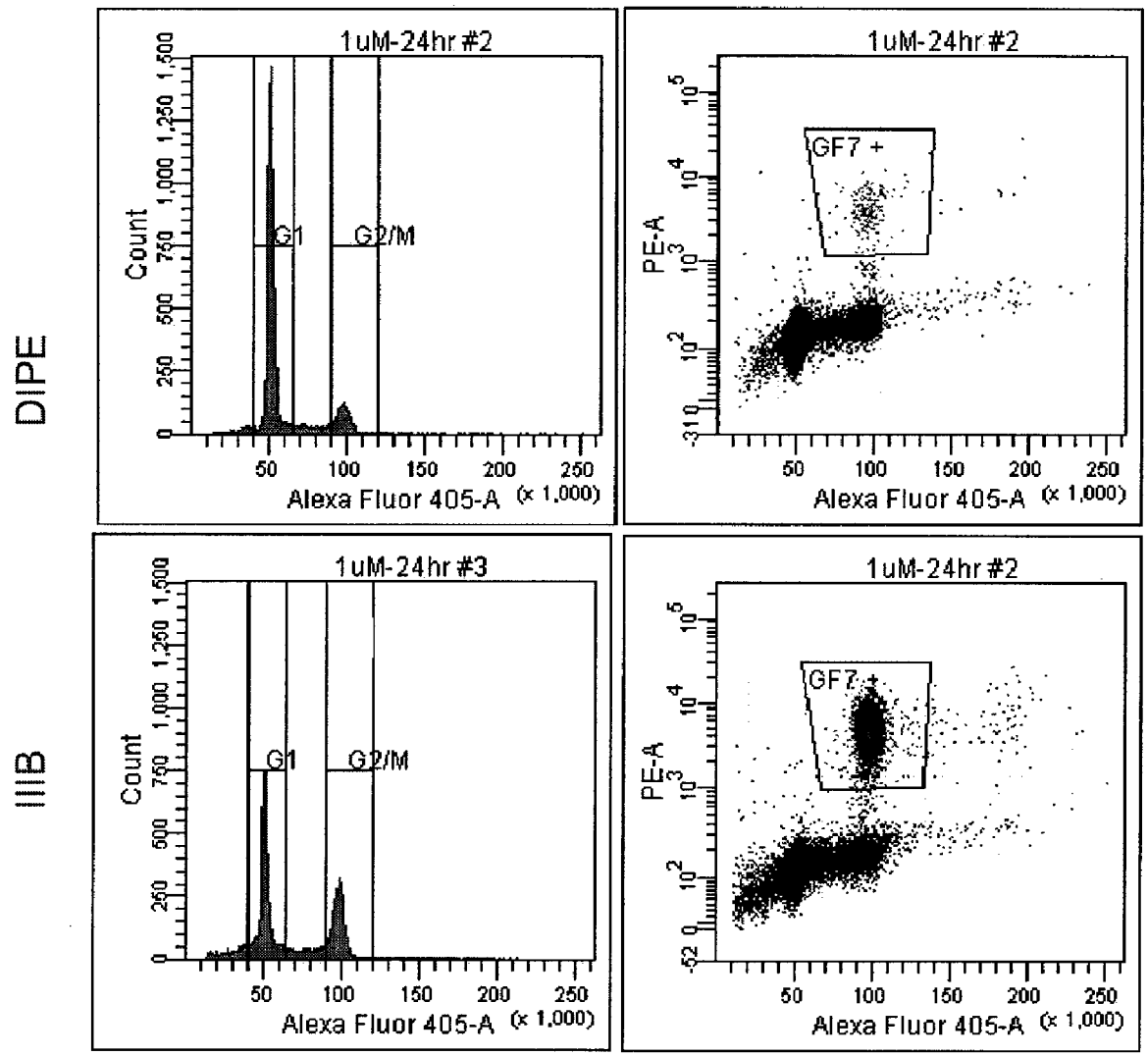
FIG. 6 illustrates the cell-cycle arrest caused by 1-(3,5-diiodo-4-(3-amino-4-methoxyphenoxy)phenylethanone, a PARP-1 inhibitor disclosed herein as Formula IIIB (1-(4-(3-amino-4-methoxyphenoxy)-3,5-diiodophenyl)ethanone), as compared to control, methyl 3,5-diiodo-4-(4-methoxyphenyloxy)benzyl ketone (1-[3,5-diiodo-4-(4'-methoxyphenoxy)-phenyl]-ethanone (DIPE)).

Fixed cells were incubated for 30 minutes with GF7-phycoerythrin (PE) antibody (BD Biosciences Pharmingen), washed with PBS and analyzed by flow cytometry. FIG. 6 compares the results obtained with DIPE and formula IIIB.

Example 15

Cell Cycle Analysis with Flow Cytometry

Programmed cell death (apoptosis) is an important homeostatic mechanism in the immune and other systems. The phenomenon of nuclear disintegration during apoptosis can be used as a marker to detect cells undergoing this process. While a variety of methods are available to detect apoptotic cells the TUNEL assay allows the rapid phenotypic identification of individual apoptotic cells using flow cytometry (FACS). Terminal transferase dUTP nick end labeling (TUNEL) is a common method for detecting DNA fragmentation that results from apoptosis. The assay based on the presence of nicks in the DNA that can be identified by terminal transferase, an enzyme that will catalyze the addition of dUTPs that are secondarily labeled with a marker. It may also label cells undergoing necrosis or cells that have suffered severe DNA damage.

Figure 7:
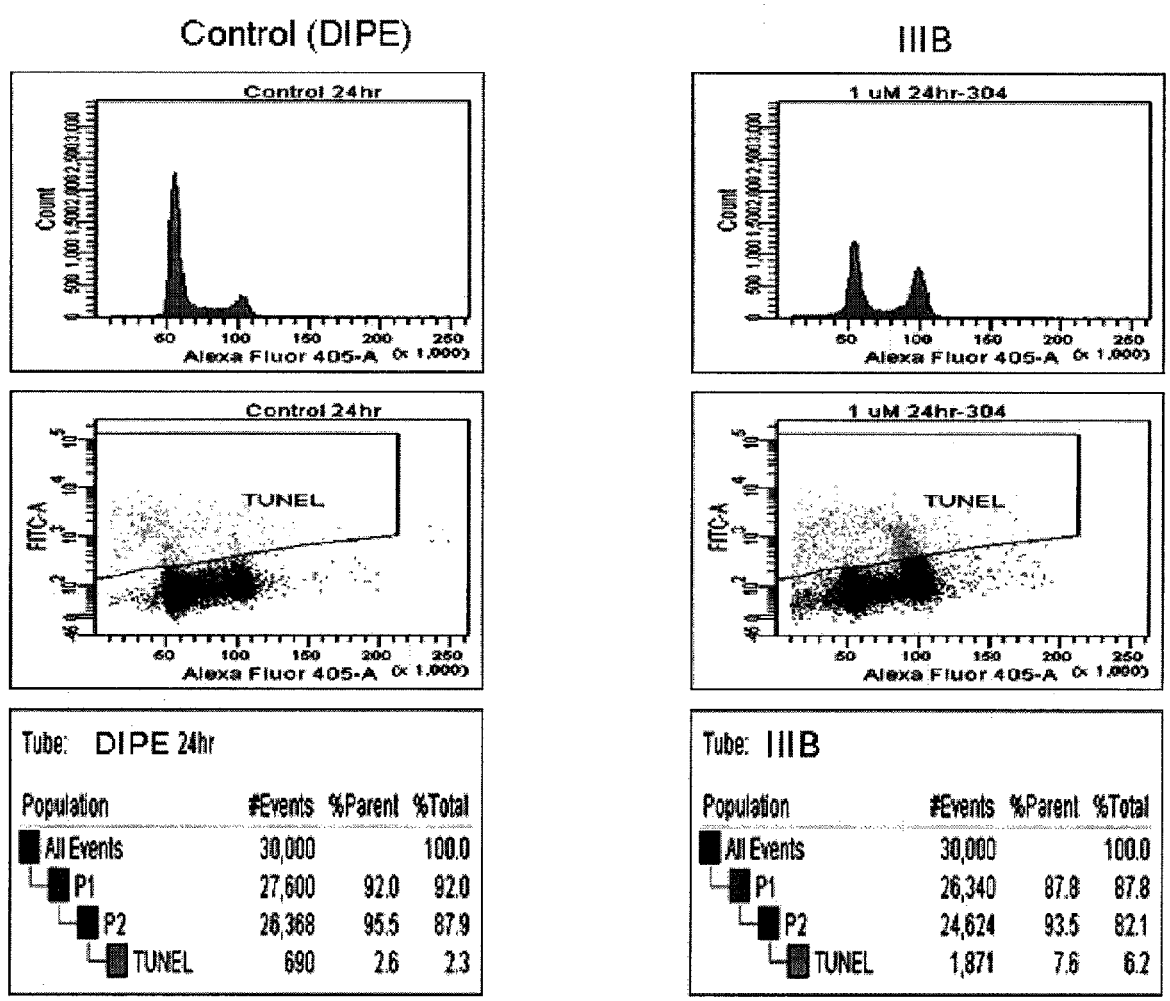
FIG. 7 illustrates the induction of apoptosis in HeLa cells induced by the compound of Formula IIIB (1-(4-(3-amino-4-methoxyphenoxy)-3,5-diiodophenyl)ethanone), as compared to control, methyl 3,5-diiodo-4-(4-methoxyphenyloxy) benzyl ketone (1-[3,5-diiodo-4-(4'-methoxyphenoxy)-phenyl]-ethanone (DIPE)).

Hela cells were obtained from ATCC. For DNA content analysis, 2×105 cells were washed twice with PBS and fixed in 70% ethanol. Cells were treated with 100 units/mL RNase A for 20 minutes at 37° C., resuspended in cold PBS containing Alexa Fluor® 405 fluorescent stain (Invitrogen) according to the manufacturer's protocol. Cells were analyzed by flow cytometry to characterize the cell cycle. To perform the TUNEL assay, cells were also fixed with 0.25% formaldehyde in the medium before the ethanol treatment and then stained with the Apo-Direct® kit (ebioscience, San Diego, Calif.). The results of this assay for DIPE (control) and formula IIIB are shown in FIG. 7.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of formula IIIA or its pharmaceutically acceptable salts or prodrugs:

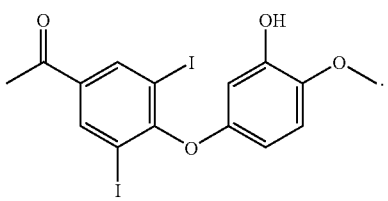

2. A compound of formula IIIB or its pharmaceutically acceptable salts or prodrugs:

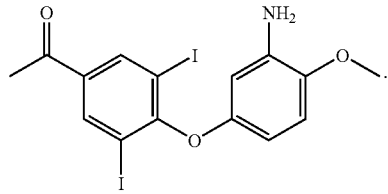

3. A compound of formula IIIC or its pharmaceutically acceptable salts or prodrugs:

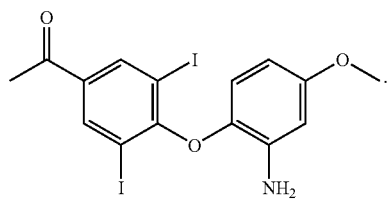

4. A compound of formula IIID or its pharmaceutically acceptable salts or prodrugs:

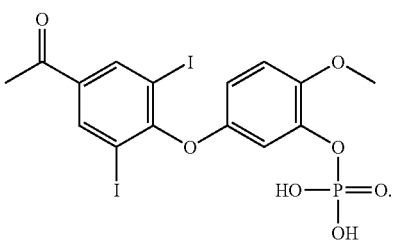

5. A formula IIIE or its pharmaceutically acceptable salts or prodrugs:

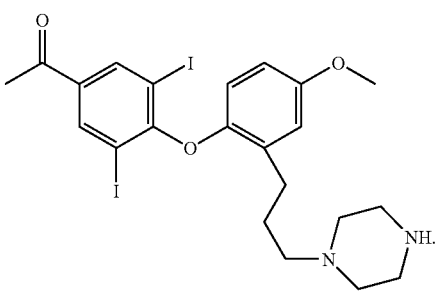

* * * * *

Disclaimer

7,538,252 B2 — Valeria S. Ossovskaya, San Francisco, CA (US); John Burnier, Pacifica, CA (US); Barry Sherman, Hillsborough, CA (US); Max Totrov, San Diego, CA (US), DRUG DESIGN FOR TUBULIN INHIBITORS, COMPOSITION, AND METHODS OF TREATMENT THEREOF. Patented date May 26, 2009. Disclaimer filed December 19, 2013 by the Assignee, BiPar Sciences, Inc.

Hereby enter this disclaimer to the entire term of said patent.

*(Official Gazette, April 1, 2014)*